(12) United States Patent
van der Donk et al.

(10) Patent No.: US 9,326,523 B2
(45) Date of Patent: May 3, 2016

(54) CLASS I AND II LANTIBIOTICS FROM GEOBACILLUS THERMODENITRIFICANS

(71) Applicant: The Board of Trustees of the University of Illinois, Champaign, IL (US)

(72) Inventors: Wilfred A. van der Donk, Champaign, IL (US); Neha Garg, Urbana, IL (US); Yuki Goto, Tokyo (JP); Weixin Tang, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/377,310

(22) PCT Filed: Feb. 7, 2013

(86) PCT No.: PCT/US2013/025161
§ 371 (c)(1),
(2) Date: Aug. 7, 2014

(87) PCT Pub. No.: WO2013/119821
PCT Pub. Date: Aug. 15, 2013

(65) Prior Publication Data
US 2015/0050256 A1     Feb. 19, 2015

Related U.S. Application Data

(60) Provisional application No. 61/595,790, filed on Feb. 7, 2012.

(51) Int. Cl.
| | | |
|---|---|---|
| *A61K 38/00* | (2006.01) | |
| *A61K 38/16* | (2006.01) | |
| *A01N 63/02* | (2006.01) | |
| *C07K 14/195* | (2006.01) | |
| *A01N 43/90* | (2006.01) | |
| *A23L 3/3463* | (2006.01) | |

(52) U.S. Cl.
CPC ............... *A01N 63/02* (2013.01); *A01N 43/90* (2013.01); *A23L 3/34635* (2013.01); *A61K 38/00* (2013.01); *A61K 38/164* (2013.01); *C07K 14/195* (2013.01)

(58) Field of Classification Search
None
See application file for complete search history.

(56) References Cited

U.S. PATENT DOCUMENTS

| | | |
|---|---|---|
| 2005/0164339 A1 | 7/2005 | van der Donk et al. |
| 2010/0041613 A1 | 2/2010 | Coleman et al. |
| 2011/0150917 A1 | 6/2011 | Hancock et al. |

OTHER PUBLICATIONS

Feng et al., "Genome and proteome of long-chaing alkane degrading Geobacillus thermodenitrificans NG80-2 isolated from a deep-subsurface oil reservoir", PNAS, 104(13):5602-5607 (2007).
Marsh et al., "In silico analysis highlights the frequency and diversity of type 2 lantibiotic gene clusters in genome sequenced bacteria", BMC Genomics, 11:679 (2010).
Zeigler, "Application of a a recN sequence similarity analysis to the identification of species within the bacterial genus *Geobacillus*", International Journal of Systematic and Evolutionary Microbiology, 55:1171-1179 (2005).
Engelke et al., "Biosynthesis of the Lantibiotic Nisin: Genomic Organization and Membrane Localization of the NisB Protein", Applied and Environmental Microbiology, 58(11):3730-3743 (1992).
Shi et al., "Production of Lantipeptides in *Escherichia coli*", J. Am. Chem. Soc., 133:2338-2341 (2011).
Begley et al., "Identification of a Novel Two-Peptide Lantibiotic, Lichenicidin, following Rational Genome Mining for LanM Proteins", Applied and Environmental Microbiology, 75(17):5451-5460 (2009).
Nes et al., "Novel lantibiotics and their pre-peptides", Antonie van Leeuwenhoek, 68:89-97 (1996).
Garg et al., "Lantbiotics from Geobacillus thermodenitrificans", PNAS, 109(14):5241-5246 (2012).
UniProt_A4IJZ5, dated May 1, 2007.
UniProt_B4BSJ7, dated Sep. 23, 2008.
Havarstein et al., "A family of bacteriocin ABC transporters carry out proteolytic processing of their substrates concomitant with export", Molecular Microbiology, 16(2):229-240 (1995).
International Search Report for corresponding PCT application No. PCT/US13/25161, dated May 21, 2013.

*Primary Examiner* — Lianko Garyu
(74) *Attorney, Agent, or Firm* — McDonnell Boehnen Hulbert & Berghoff LLP

(57) ABSTRACT

The disclosure provides lantibiotics geobacillin I and geobacillin II from *Geobacillus thermodenitrificans*, compositions comprising the lantibiotics, and methods of use of the lantibiotics. Further disclosed are the sequences of lantibiotics geobacillin I and geobacillin I, and alternative structures of geobacillin I and geobacillin II comprising amino acid substitutions. Antimicrobial compositions comprising one or more isolated geobacillins and a pharmaceutically acceptable carrier, and methods of reducing reproduction of bacteria comprising administering to a subject a therapeutically effective amount of the antimicrobial composition are also provided.

21 Claims, 35 Drawing Sheets

(2S,6R)-Lanthionine (Lan)

(2S,3S,6R)-3-MethylLanthionine (MeLan)

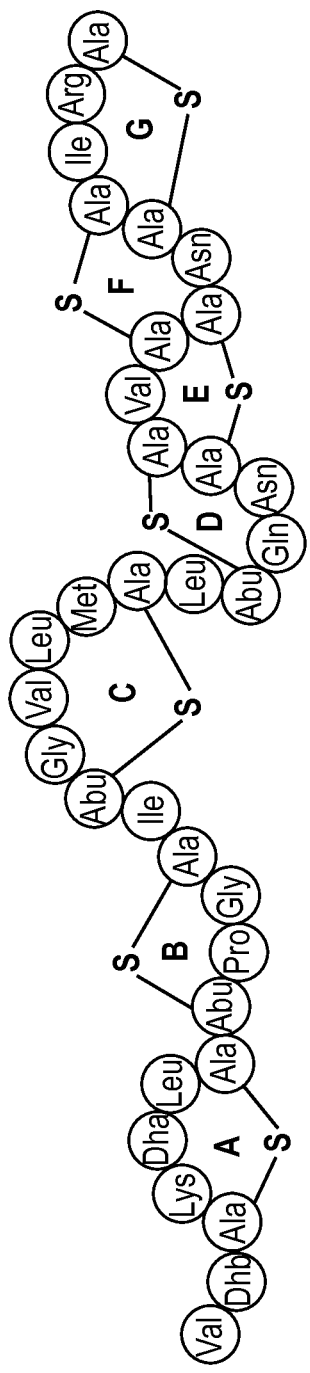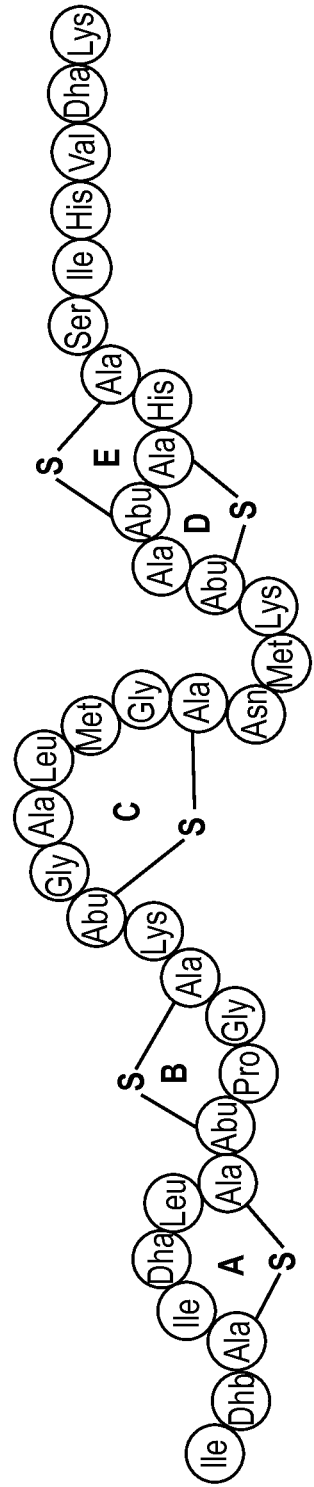
FIG. 4C
FIG. 4D (2S,6R)-Lanthionine (Lan)

(2S,3S,6R)-3-MethylLanthionine (MeLan)

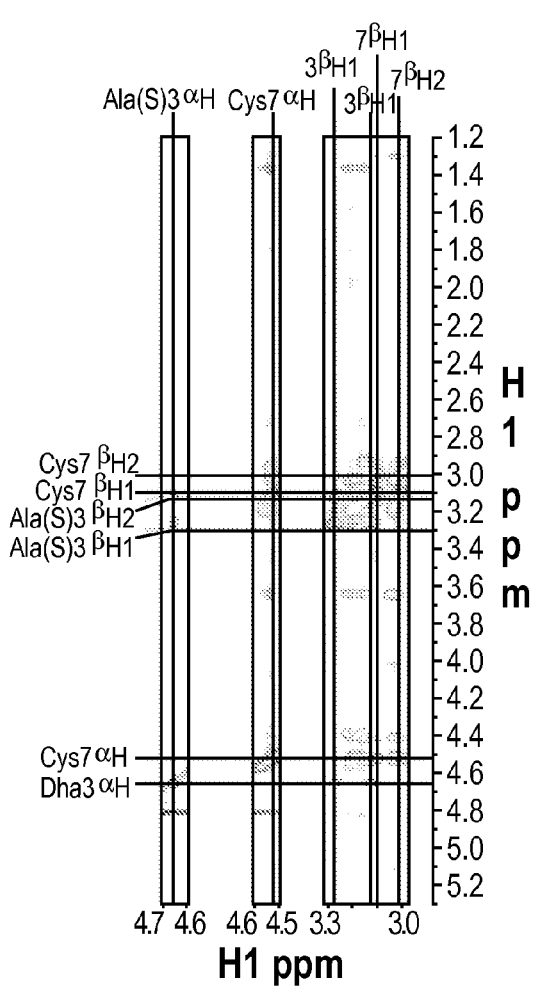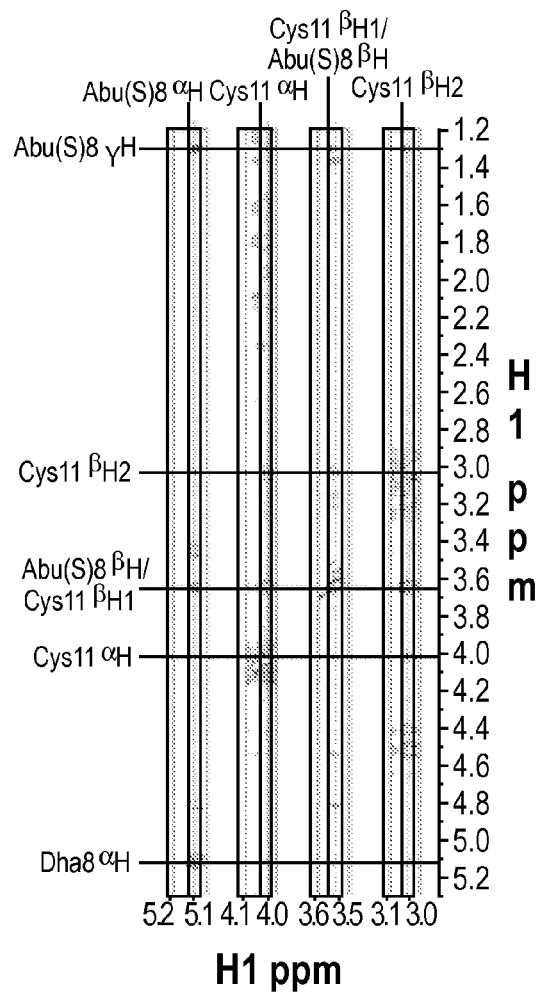

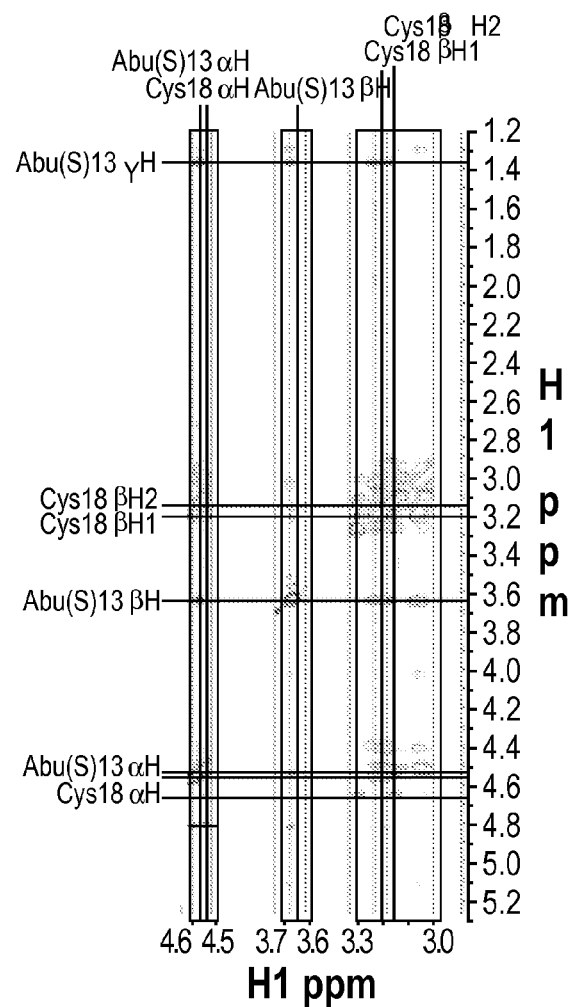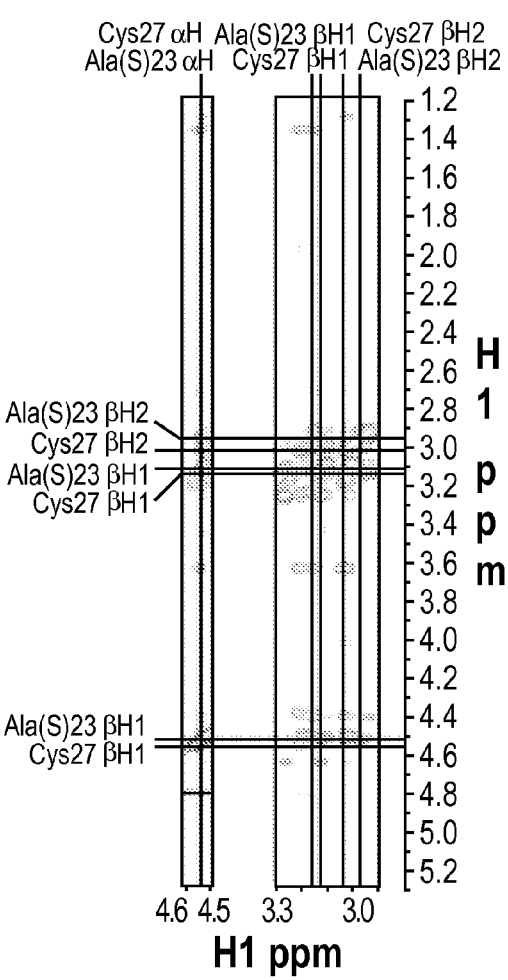
FIG. 11E
FIG. 11F

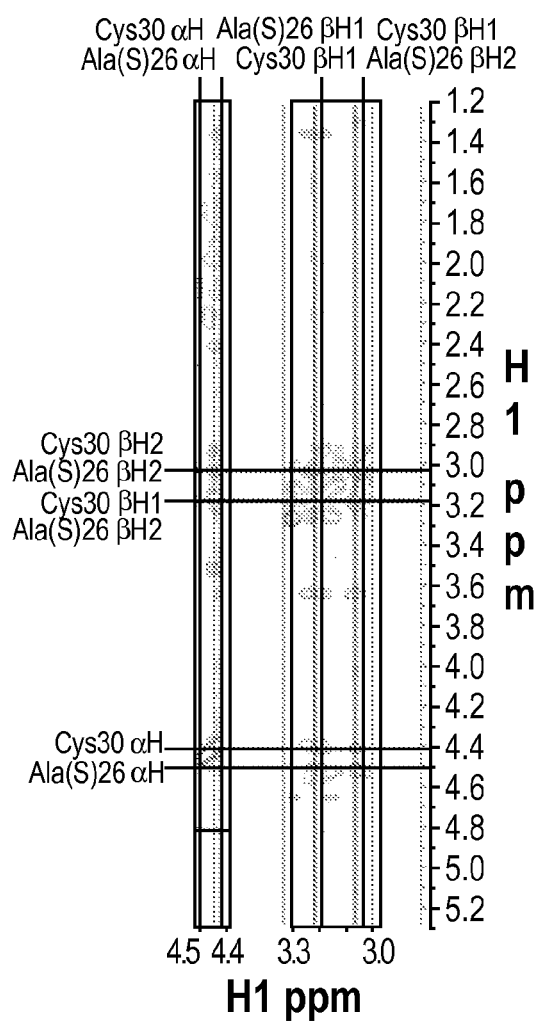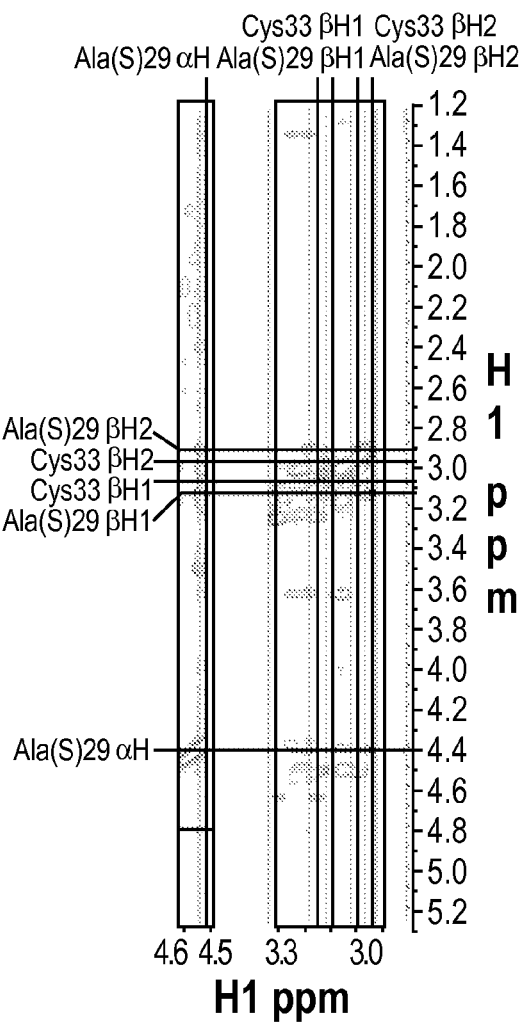

Geobacillin II

SEQ ID NO:45

SEQ ID NO:46

SEQ ID NO:47

SEQ ID NO:48

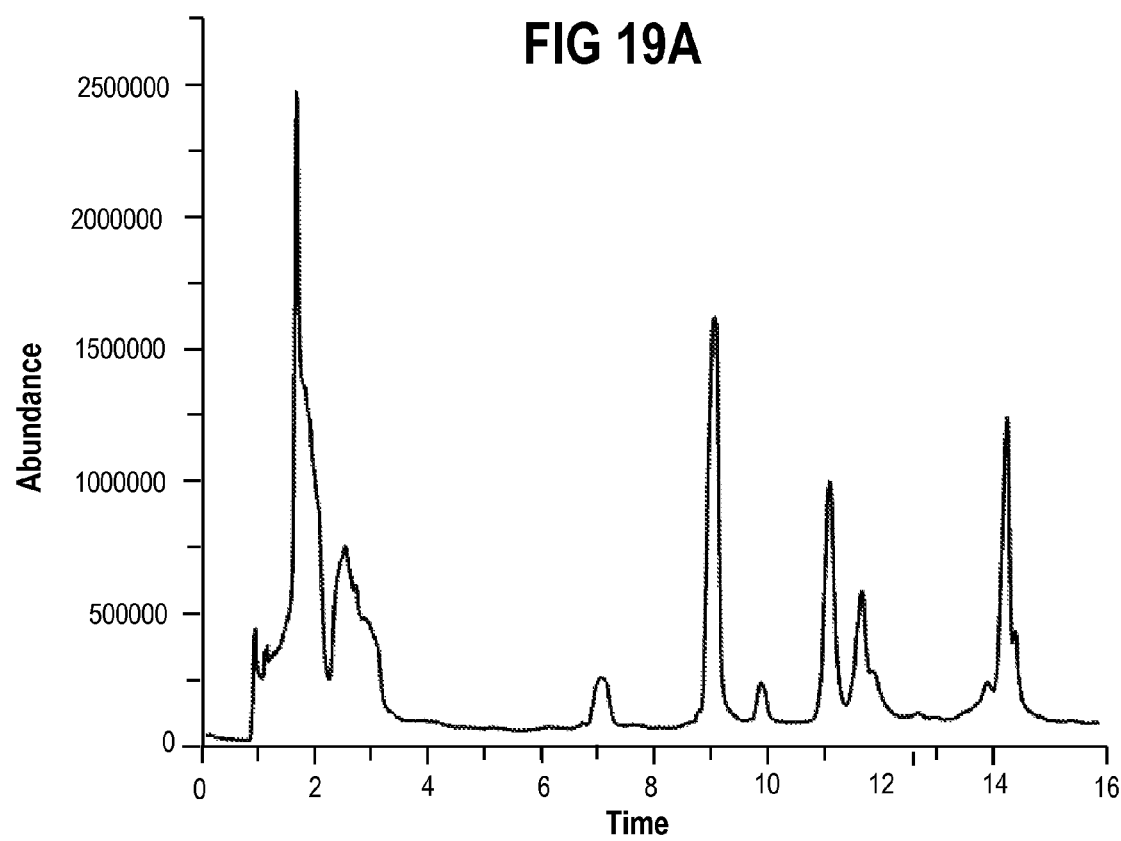

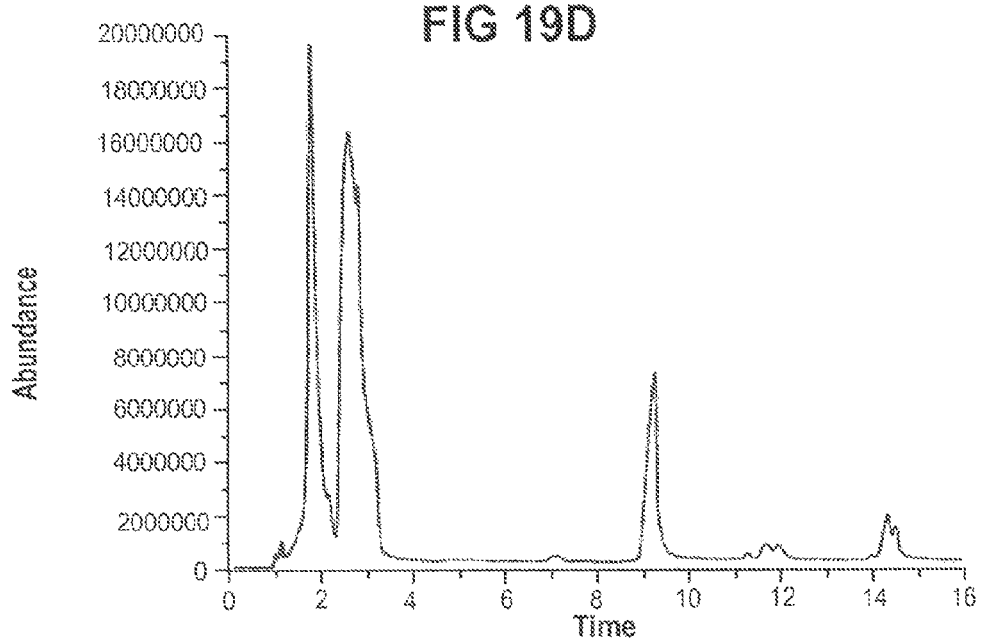
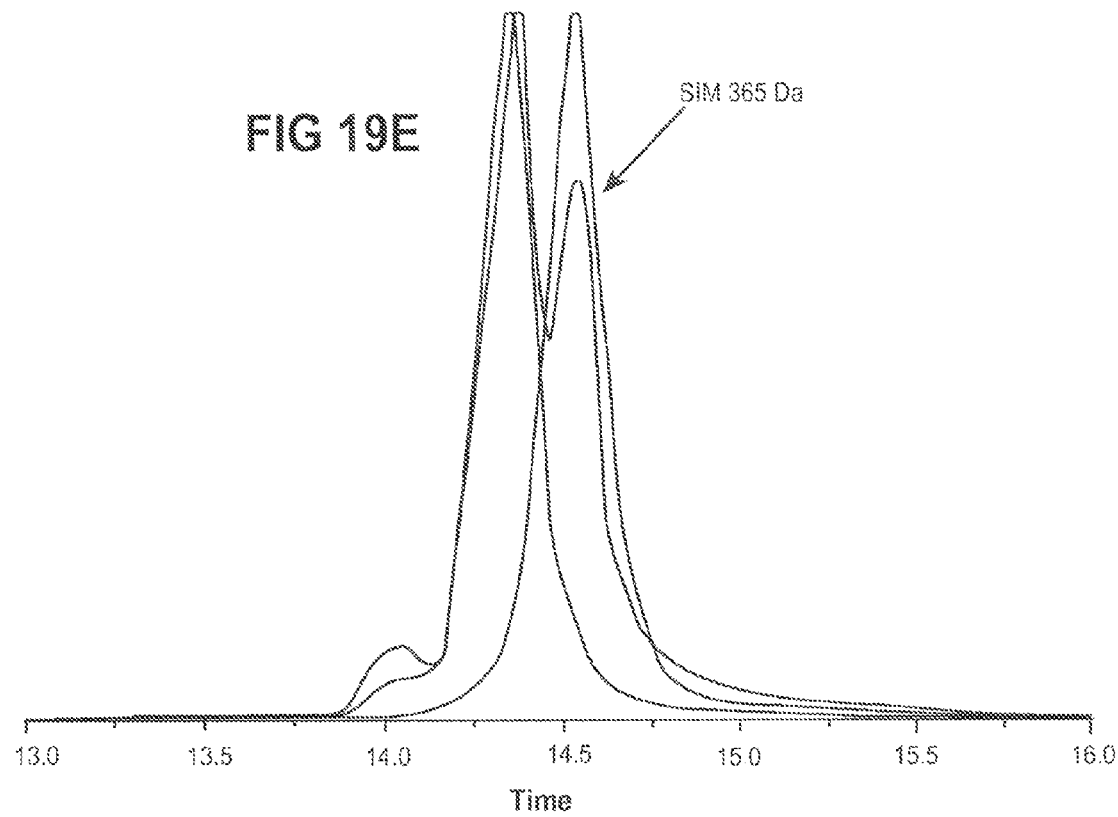

CLASS I AND II LANTIBIOTICS FROM GEOBACILLUS THERMODENITRIFICANS

PRIORITY

This application claims the benefit of U.S. provisional application Ser. No. 61/595,790, filed on Feb. 7, 2012, which is incorporated herein by reference in its entirety.

GOVERNMENT INTEREST

This invention was made with United States government support under contract number RO1 58822 awarded by the National Institutes of Health. The United States government has certain rights in the invention.

BACKGROUND OF THE INVENTION

Lantibiotics are ribosomally synthesized and posttranslationally modified polycyclic peptides containing thioether bridges (1). The crosslinks are made in a two-step process of first dehydration of Ser and Thr residues to the corresponding dehydro amino acids dehydroalanine (Dha) and dehydrobutyrine (Dhb), and subsequent conjugate addition of the thiol of Cys to the dehydro amino acids. The N-terminus of the precursor peptide is termed the leader peptide and is removed in the final step of maturation whereas the C-terminus is designated the core peptide and is converted into the lantibiotic (2). For class I lantibiotics, dehydration and cyclization are carried out by two different enzymes, generically called LanB and LanC, whereas for class II lantibiotics, both reactions are performed by a bifunctional enzyme (LanM). The class I lantibiotic nisin, the most extensively studied member of the lantibiotic family, was first approved for use as a food preservative to combat food-borne pathogens in 1969 and is currently used in over 50 countries (3). Despite this widespread use, very little resistance against nisin has been reported, possible owing to its mode of action. Nisin binds to the pyrophosphate group of lipid II, thereby preventing its use as an essential intermediate in bacterial cell wall biosynthesis (4-6). In addition, the lipid II-nisin complex forms long-lived pores resulting in depolarization of the membrane (7, 8). In comparison to other modes of action, it may be more challenging for a target organism to change the structure of an advanced intermediate such as lipid II that is biosynthesized in 10 steps (9, 10), than to acquire other resistance mechanisms such as efflux pumps and enzyme mutations. These latter mechanisms will not affect nisin as it acts on the outside of the bacterial cell and has a small molecule as target.

In addition to its use as a food preservative, the Center for Veterinary Medicine of the U.S. Food and Drug Administration recently ruled positively on application of nisin for intramammary treatment of subclinical mastitis in dairy cattle. After approval of the pending New Animal Drug Application, a nisin-containing product would allow treatment of bovine mastitis with a zero milk discard time and zero meat withdrawal period (i.e. milk and/or meat from treated cattle would not have to be discarded). One drawback that has been noted for nisin is its limited stability at pH 7 (11-15). Hence, more stable analogs may prove more effective.

SUMMARY OF THE INVENTION

In one embodiment of the invention, an isolated geobacillin is provided. The geobacillin can comprise the structure of:

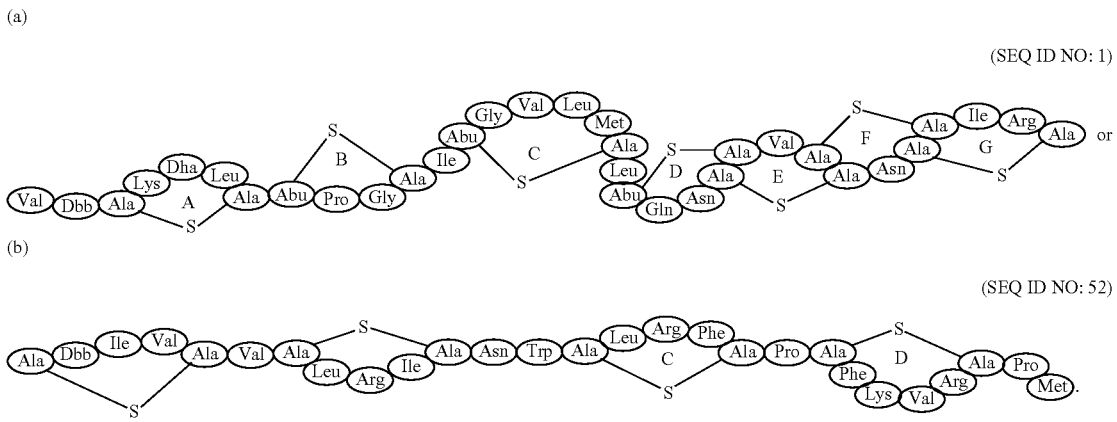

Another embodiment of the invention provides an antimicrobial composition comprising one or more isolated geobacillins of the invention and a pharmaceutically acceptable carrier, MOPS buffer, phosphate buffer, pharmaceutically acceptable diluent, other diluent, or excipient. The (a) structure above can have the following amino acid substitutions Dha5Phe, or Leu6Ile, or both Dha5Phe and Leu6Ile. The (b) structure can have one or more of the following amino acid substitutions: Ala1Abu, Dhb2Ala Ile3Arg. The composition can retain about 80% or more biological activity at temperatures between about 55° C. to about 80° C. The A ring of the (a) and (b) structures above can have LL (2R,6R) stereochemistry or can have a mixture of LL stereochemistry and DL-stereochemistry (2R,6R and 2S,6R).

The composition can further comprise at least one antifungal agent, one additional antimicrobial agent, or a membrane disrupting agent. The one additional antimicrobial agent can have Gram negative bacteriostatic or bacteriocidal activity and the membrane disrupting agent can render Gram negative bacteria susceptible to the one or more geobacillins. The one or more isolated geobacillins can be present in the composition at about 0.001, 0.01, 0.1, 1, 5, 10, 20, 30, 40, 50, 75, 100, or 150 mg/kg.

Yet another embodiment of the invention provides a method of reducing reproduction of bacteria or reducing numbers of bacteria present in or on in a subject, comprising administering to the subject a therapeutically effective amount of the antimicrobial composition. The subject can be a human. The isolated lantibiotic can be administered orally or topically, nasally, buccally, sublingually, transmucosally, rectally, transdermally, by inhalation, by injection or intrathecally. The injection can be intramuscular, intravenous, intrapulmonary, intramuscular, intradermal, intraperitoneal, intrathecal, or subcutaneous injection.

Still another embodiment of the invention provides a preservative comprising an effective amount of one or more geobacillins of the invention in a physiological solution at a pH of between 3 and 8.

Even another embodiment of the invention provides a food or beverage composition comprising an amount of one or more geobacillins of the invention sufficient to reduce the reproduction of bacteria or numbers of bacteria in the composition.

Another embodiment of the invention provides a method of reducing reproduction of bacteria or reducing numbers of bacteria present in or on a composition or object, comprising contacting the antimicrobial composition of the invention with the composition or object for a period effective to reduce reproduction of bacteria or reduce numbers of bacteria in or on the composition or object. The composition can be a food or beverage.

Yet another embodiment of the invention provides a method of reducing a biofilm or biofouling condition comprising contacting the antimicrobial composition of the invention with the biofilm or biofouling condition for a period effective to reduce reproduction of bacteria or reduce numbers of bacteria in or on the biofilm or biofouling condition.

Still another embodiment of the invention provides a kit comprising one or more geobacillins of the invention and one or more applicators.

Another embodiment of the invention provides a method for producing an isolated geobacillin. The method comprises inserting an enzyme cleavage site within about 10 nucleotides of the −1 position of a nucleic acid molecule encoding GeoA1 to make a mutated GeoA1 nucleic acid molecule. The mutated GeoA1 nucleic acid molecule and nucleic acid molecules that encode GeoB, GeoC GeoAII, and GeoM are inserted into one or more cloning vectors. Bacterial cells are then transformed with the one or more cloning vectors. The bacterial cells lysed and the cell lysate is collected. The cell lysate is treated with an enzyme that will cause cleavage at the enzyme cleavage site. The geobacillin is isolated from the cell lysate to produce an isolated geobacillin. The nucleic acid molecules encoding GeoA1 GeoB, GeoC GeoAII, and GeoM can be codon optimized for expression in the bacterial cells. The bacterial cells can be, for example, *Escherichia coli*.

Even another embodiment of the invention provides a geobacillin pre-peptide comprising (SEQ ID NO:62) or (SEQ ID NO:65) or a geobacillin comprising SEQ ID NO:44-52, 54-60.

Therefore, the invention provides an isolated lantibiotic from *Geobacillus thermodenitrificans* NG80-2 termed geobacillin I that is an analog of nisin with two additional crosslinks. The compound was produced heterologously in *Escherichia coli*, its ring topology was determined by NMR spectroscopy, and its activity against various bacteria was assessed. The compound was three-fold more active than nisin against *Streptococcus dysgalactiae*, one of the main contagious causative agents of clinical bovine mastitis (16). Geobacillin I also demonstrates increased stability compared to nisin A.

In addition to geobacillin I, of the invention also provides a second lantibiotic, geobacillin II, encoded on the genome of *Geobacillus thermodenitrificans* NG80-2. It was heterologously produced in *E. coli*, its ring topology was determined by tandem mass spectrometry, and its spectrum of activity was evaluated. Interestingly, geobacillin II, which has no obvious structural homologs among lantibiotics of known structure, was only active against bacilli.

BRIEF DESCRIPTION OF THE DRAWINGS

FIG. 4A-D show structure determination of geobacillin I. A) Illustration of the nOe correlations used to establish thioether connectivities. B) Representative NOESY data showing some of the correlations used for ring assignments (see also FIG. 11). C) Ring topology of geobacillin I (SEQ ID NO:1). D) Ring topology of nisin A (SEQ ID NO:2).

FIG. 11A-H show NOESY spectrum of geobacillin I in $D_2O$ (mixing time=0.40 s) for the assignment of ring topology. Panels A and B. Schematic representation of the correlations used to assign ring topology. The part of Lan derived from Ser is designated Ala(S). The part derived from Cys is designated Ala. Similarly, the part of MeLan derived from Thr is designated Abu(S), and the part derived from Cys is designated as Ala. In panels B-H, protons of thioether linked Ala (S)/Abu(S) and Cys residues are marked by their chemical shifts in slices of the NOESY spectrum that were excised to illustrate the resonances associated with each ring. (C) Diagnostic resonances used to determine ring A. (D) Diagnostic resonances used to determine ring B. (E) Diagnostic resonances used to determine ring C. (F) Diagnostic resonances used to determine ring E. (G) Diagnostic resonances used to determine ring F. (H) Diagnostic resonances used to determine ring G. Contrast levels were adjusted if necessary to clearly show the correlations.

FIG. 19A-E. Panel A shows a total ion gas chromatogram of derivatized amino acids obtained by acid hydrolysis of geobacillin I. Panel B shows GC/MS trace (SIM 379 Da, 365 Da) of derivatized (methyl)lanthionine obtained from geobacillin I overlayed with a GC/MS trace of a synthetic (2S,3S, 6R)-methyllanthionine standard and a (2S,6R)-lanthionine standard. Panel C shows GC/MS traces (SIM 379 Da, 365 Da) for derivatized (methyl)lanthionine obtained from hydrolyzed geobacillin I (largest peak at 365 Da, smallest peak at 379 Da) compared with derivatized (methyl)lanthionine obtained from nisin A (largest peak at 379 Da; smallest peak at 365 Da). Panels D+E show GC/MS analysis of geobacillin II. Panel D shows the total ion gas chromatogram of derivatized amino acids obtained by acid hydrolysis of geobacillin II. Derivatized lanthionine is observed but not derivatized methyllanthionine. Panel E shows GC/MS trace (SIM 365 Da) of derivatized lanthionine obtained from geobacillin II (two peaks) overlaid with a GC/MS trace of a synthetic DL-lanthionine standard (no peak at 365 Da) and LL-lanthionine (peak at 365 Da). The LL-lanthionine observed in GC/MS analysis of geobacillin II is due to Ring A having LL (2R,6R) stereochemistry. There was no signal corresponding to methyllanthionine (SIM 379 Da).

DETAILED DESCRIPTION OF THE INVENTION

Figure 1A:
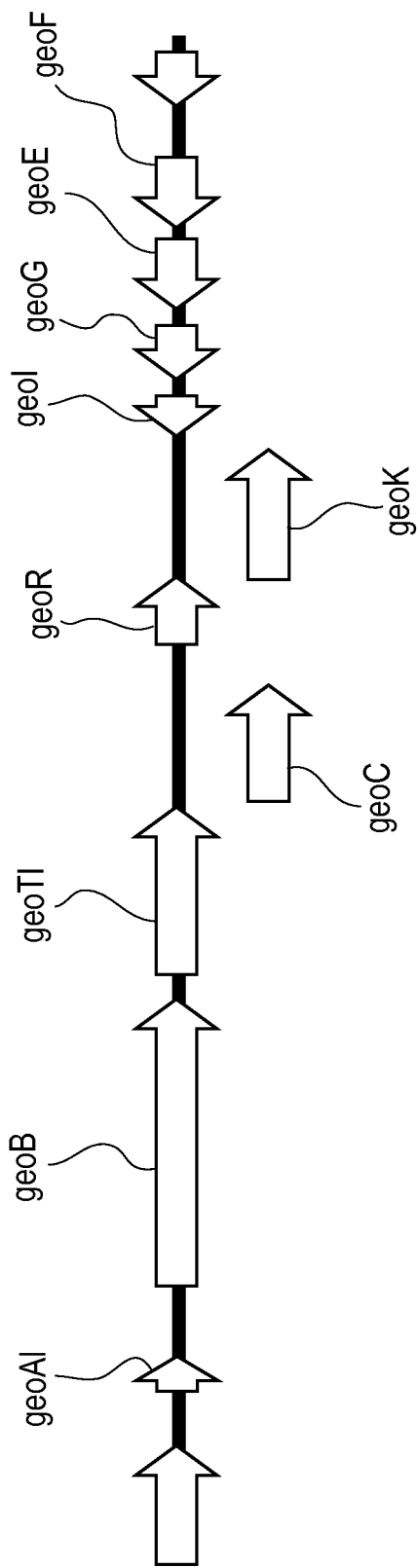
FIG. 1A-E show gene clusters and primary sequence alignment of precursor peptides of geobacillin I and geobacillin II from *G. thermodenitrificans* NG80-2. A,B) Gene clusters for the biosynthesis of geobacillin I and geobacillin II. See Feng et al. (2007) *Proc Natl Acad Sci USA*, 104: 5602-5607. The genes for the precursor peptide are geoAI, geoAII, modification enzymes are geoB, geoC, geoM, transporter/protease genes are geoTI, geoTII, regulatory proteins are geoR, geoK, and immunity proteins are geoI, geoG, geoE, geoF. C) Sequence alignment of the core peptides of selected known class I lantibiotics with that of GeoAI. Serines and threonines undergoing dehydration are at positions 2, 3, 5, 8, 13, 18, 21, 23, 24, 25, 27, 30, cysteines involved in ring formation are at positions 7, 11, 19, 25, 26, 28, 31, 34. The additional two cysteines not found in nisin are at positions 31, 34. D) Sequence alignment of the leader peptides of select class I lantibiotics with the leader peptide of geobacillin I. E) Sequence alignment of the precursor peptide GeoAII with type II lantibiotics that undergo a second proteolytic processing step after removal of the leader peptide at the double Gly cleavage site (indicated by a black arrow between positions −7 and −6). The second cleavage site for this group of lantibiotics is indicated between positions −1 and 1. The ring topology of these compounds, when known, is also shown at the top and the ring topology deduced in this study for geobacillin is shown at the bottom. The two possible Met residues that could be the start of the leader peptide are underlined.
Figure 1B:
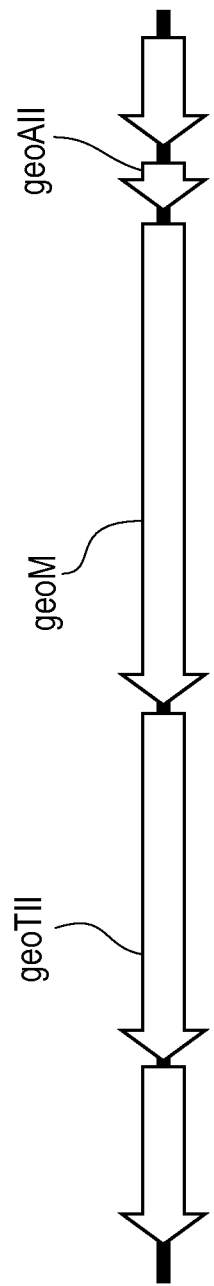

As used herein, the singular forms "a," "an," and "the" include plural referents unless the context clearly dictates otherwise.

The final structure of lantibiotics cannot be determined given the nucleic acid sequences of the gene clusters encoding the components necessary for a bacterium to produce lantibiotics. Even given substantially purified lantibiotics (which are difficult to obtain), it is arduous to determine the exact final structure of a lantibiotic. The literature is replete with examples of initially reported incorrect final structures of lantibiotics. See, e.g., Caetano et al., Chemistry & Biology, 18:90 (2011) (reporting the corrected structures for Bliα and Bliβ of the lantibiotic lichenicidin); Maffioli et al., J. Natural Prod. 72:605 (2009) (reporting the corrected structure for lantibiotic 97518).

Herein, we describe a nisin analog encoded on the genome of the thermophilic bacterium *Geobacillus thermodenitrificans* NG80-2. This analog termed geobacillin I was obtained by heterologous expression in *E. coli* and subsequent purification. Extensive NMR characterization demonstrated that geobacillin I contains seven thioether crosslinks, two more than the five crosslinks found in nisin and the most crosslinks found in any lantibiotic to date. The antimicrobial spectrum of geobacillin I was generally similar to that of nisin, with increased activity against *Streptococcus dysgalactiae*, one of the causative agents of bovine mastitis. In addition to geobacillin I, the genome of *G. thermodenitrificans* also contains a class II lantibiotic biosynthetic gene cluster. The corresponding compound was produced in *E. coli*, and has a ring topology different than that of any known lantibiotic as determined by tandem mass spectrometry. Interestingly, geobacillin II only demonstrated antimicrobial activity against *Bacillus* strains. Seven *Geobacillus* strains were screened for production of the geobacillins using whole cell MALDI-MS and five were shown to produce geobacillin I, but none produced geobacillin II.

Geobacillins

The geobacillins of the invention are polypeptides comprising post-translational modifications. Post-translational modifications are chemical modifications of a polypeptide after it has been translated. A polypeptide is a polymer of two or more amino acids covalently linked by amide bonds. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide, etc., has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure. A purified polypeptide does not include unpurified or semi-purified cell extracts or mixtures of polypeptides that are less than 70% pure.

The term "geobacillin" or "geobacillin polypeptide" can refer to one or more of one type of geobacillins (a set of geobacillins). "Geobacillins" can also refer to mixtures of two or more different types of geobacillins (a mixture of geobacillins). The terms "geobacillin" or "geobacillins" can each also mean "one or more geobacillins."

Geobacillin I is shown in FIG. 4C. Geobacillin I has 7 rings labeled A-G. Four of these rings are formed by lanthionine residues (Ala-S-Ala), including one in ring A ($Ala_3$-S-$Ala_7$), one in ring E ($Ala_{23}$-S-$Ala_{27}$), one in ring F ($Ala_{26}$-S-$Ala_{30}$), and one in ring G ($Ala_{29}$-S-$Ala_{33}$). Three of the rings are formed by methyl-lanthionine residues (Abu-S-Ala), including one in ring B ($Abu_8$-S-$Ala_{11}$), one in ring C ($Abu_{13}$-S-$Ala_{18}$), and one in ring D ($Abu_{20}$-S-$Ala_{24}$). In one embodiment of the invention, the Val at position 15 can be substituted with an Ile. The molecule is amenable to amino acid substitutions and variants with other amino acid substitutions are expected to result in biologically active molecules.

In one embodiment of the invention, geobacillin I has the following mutations; Dha5Phe, or Leu6Ile, or both Dha5Phe and Leu6Ile. Geobacillin I having mutations Dha5Phe and Leu6Ile is geobacillin I KFI, which has greater solubility and improved stability over wild-type geobacillin I.

The amino acid sequence of wild-type geobacillin I, prior to post-translational modification is MAKFDDFDLDI-WKKQDDVVQPKVTSKSLCTPGCITGVLM-CLTQNSCV SCNSCIRC (SEQ ID NO:3)(optionally an L is at position 4 or an I is at position 19, or an L is at position 4 and an I is at position 19; optionally an N is present at position 23). About 1, 2, 3, 4, 5, 6, 7, 8, 9, 10, 11, 12, 13, 14, 15, 20, 25, 30 or more (or any range of amino acids between about 1 and 30 amino acids) can be added to the wild-type or mutant geobacillin. Additionally, about 30, 25, 20, 15, 14, 13, 12, 11, 10, 9, 8, 7, 6, 5, 4, 3, 2, 1, or less (or any range of between about 30 and 1 amino acids) amino acids can be added to the wild-type or mutant geobacillin. For example, in one embodiment of the invention a geobacillin has the following amino acid sequence: GSSHHHHHHSQDPMAKFDDFDLDIV-VKKQDDWQPKVTSKSLCTPGCITGVLM-CLTQNSCVSCNSCIRC (SEQ ID NO:4), which is the same as SEQ ID NO:3, but has additional amino acids from the use of a vector to produce the geobacillin. The sequence of geobacillin I after the leader is cleaved and prior to other post-translational modification is VTSKSLCTPGCITGVLM-CLTQNSCVSCNSCIRC (SEQ ID NO:62). The leader sequence of geobacillin I is MAKFDDFDLDIWKKQD-DWQPK (SEQ ID NO:63), optionally an L is at position 4 or an I is at position 19, or an L is at position 4 and an I is at position 19; optionally an N is present at position 23).

Figure 13A:
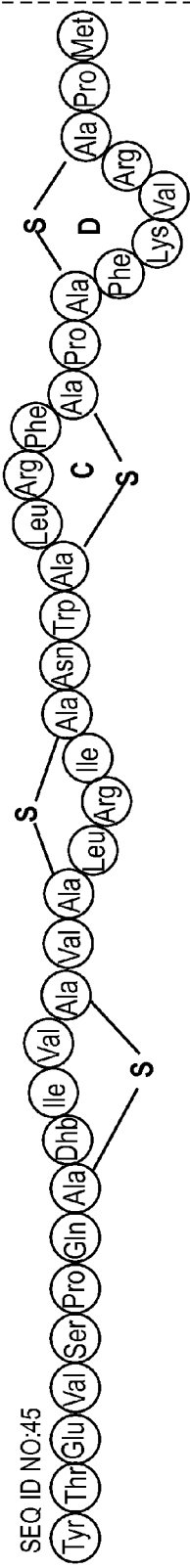
FIG. 13A-B shows alternative structures for geobacillin II.
Figure 13A:
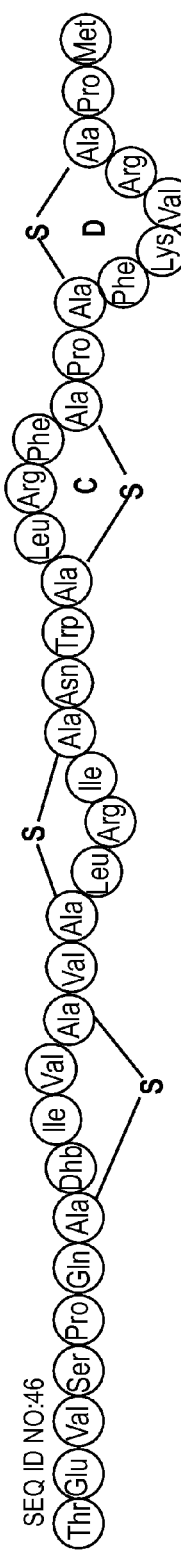
Figure 13A:
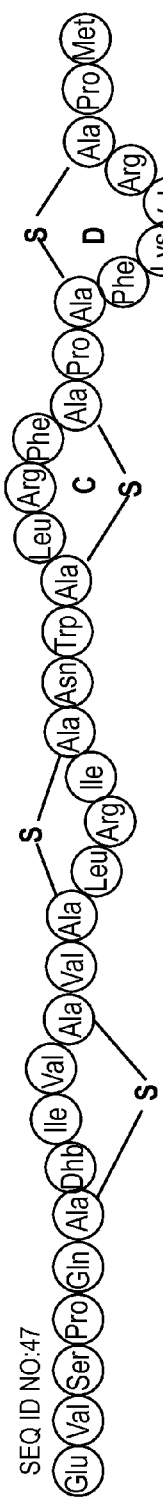
Figure 13A:
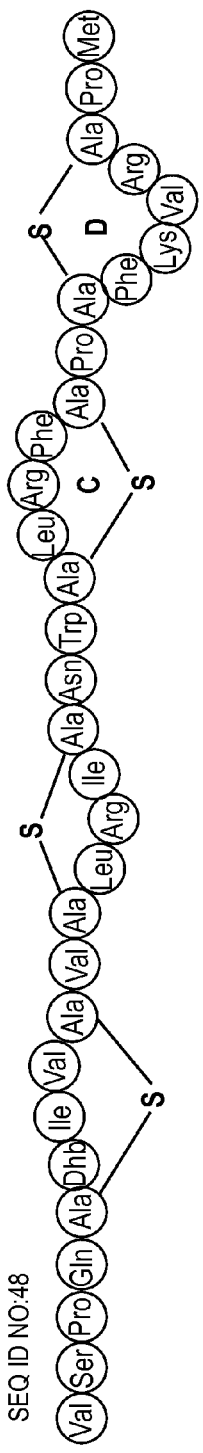
Figure 13A:
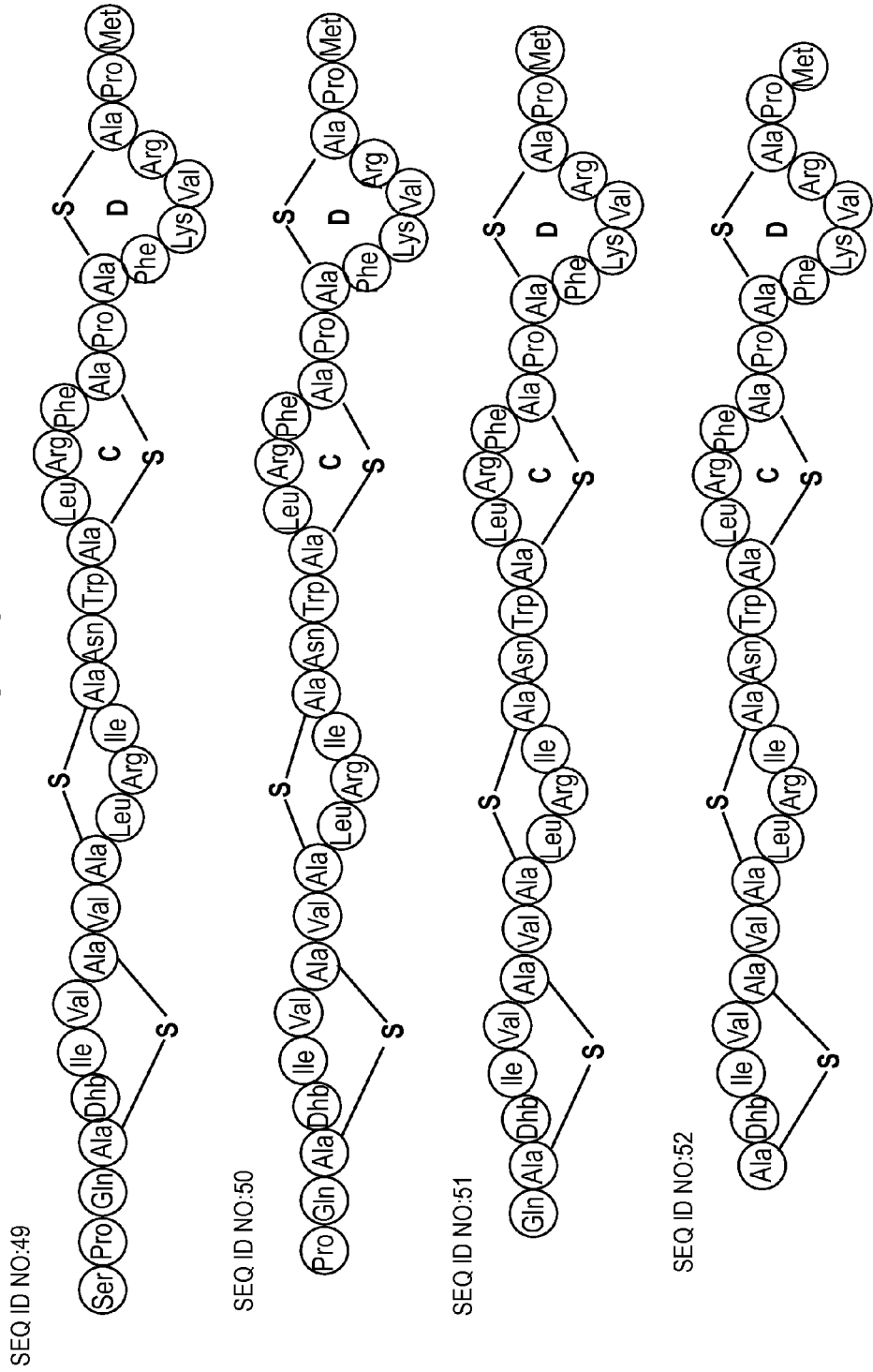
Figure 13B:
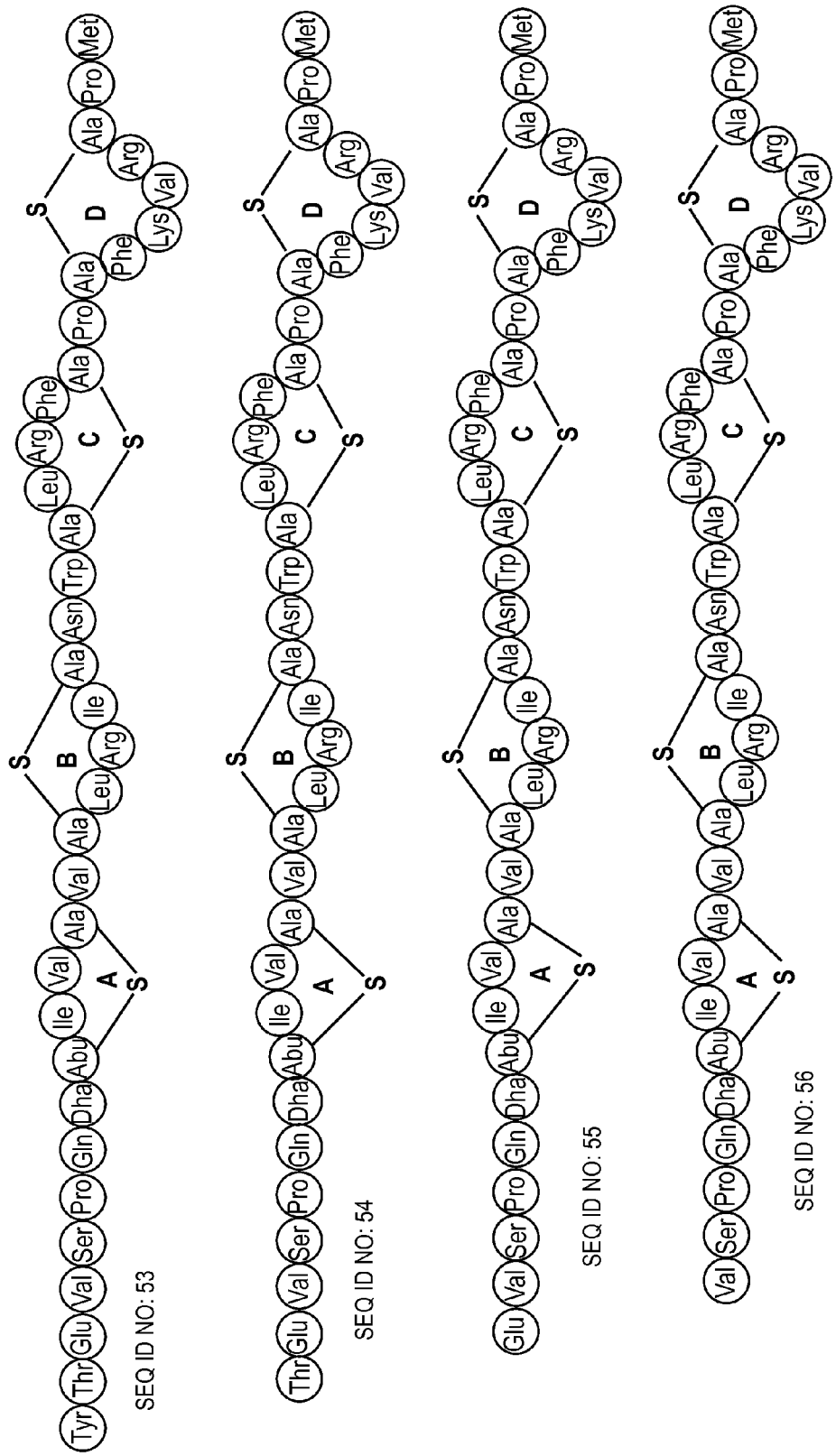
Figure 13B:
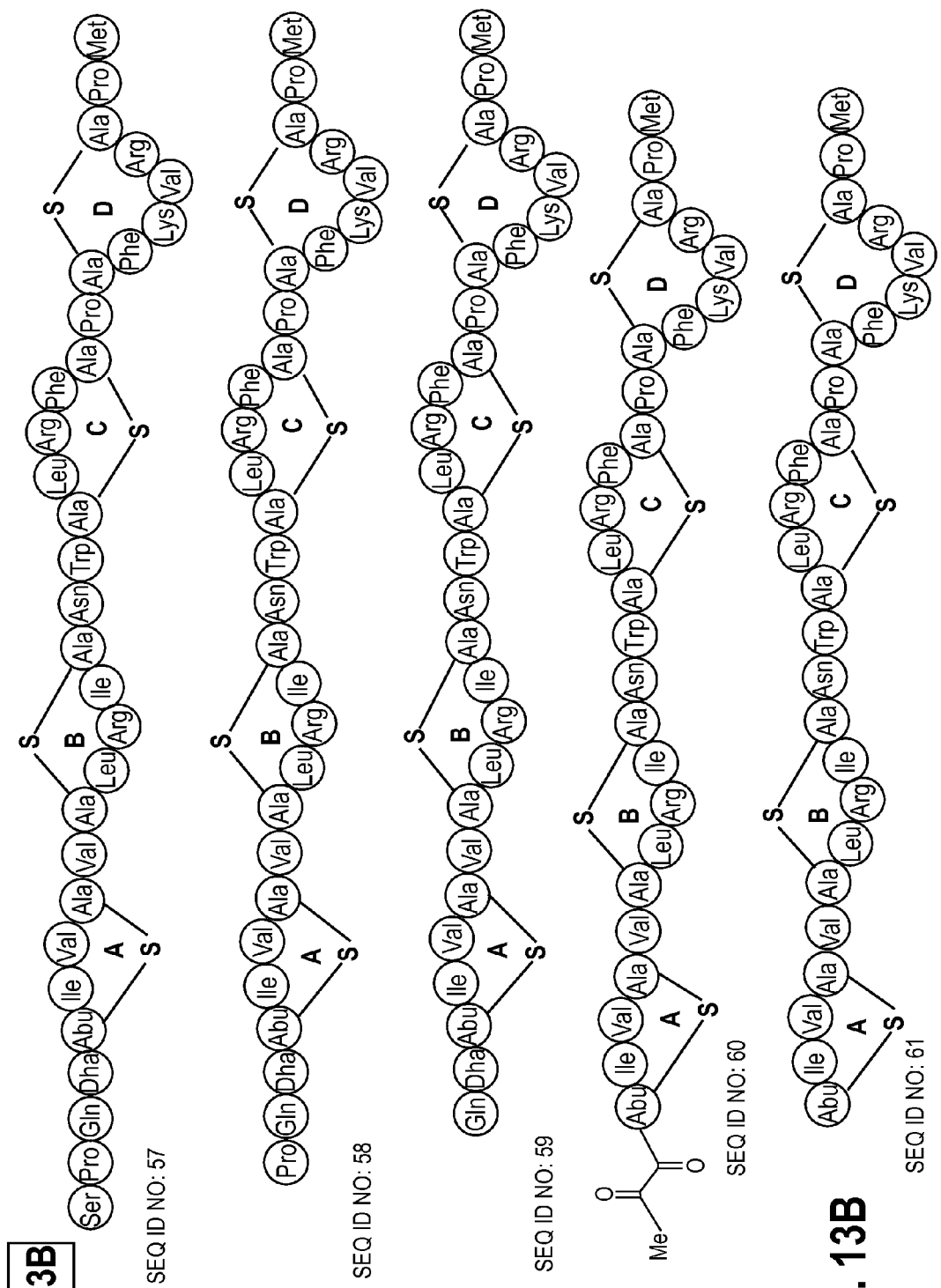
Figure 14:
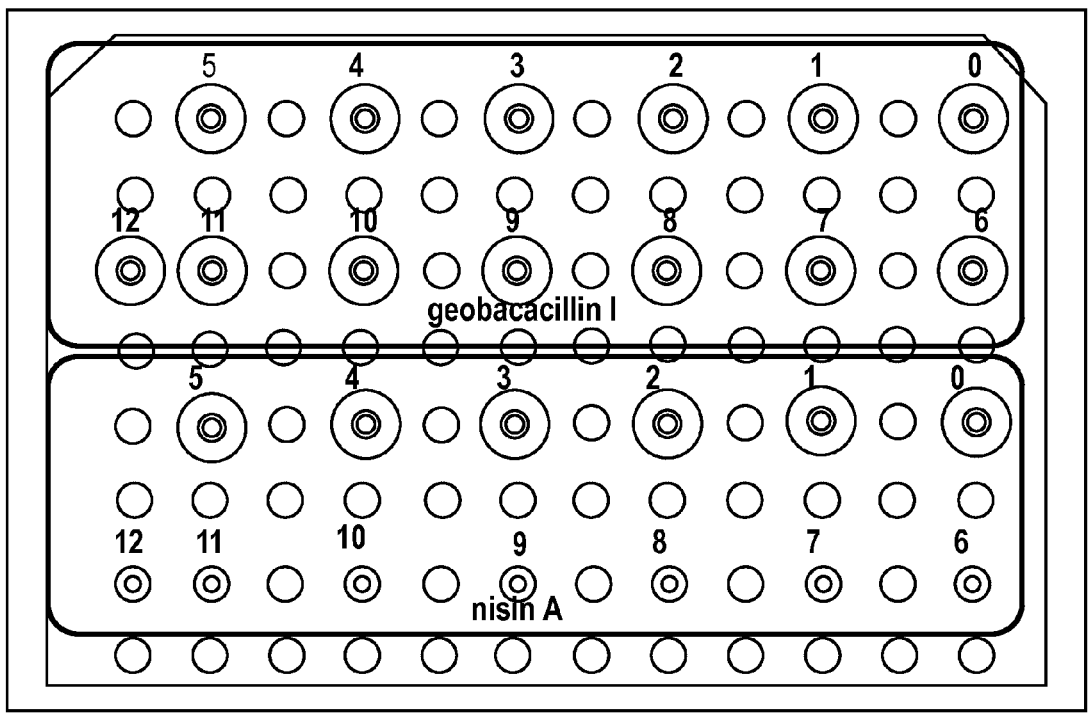
FIG. 14 shows an agar diffusion growth inhibition assay with $B.$ $subtilis$ 6633 to determine the relative stabilities of geobacillin I and nisin A at pH 7.0 and 60° C.
Figure 15:
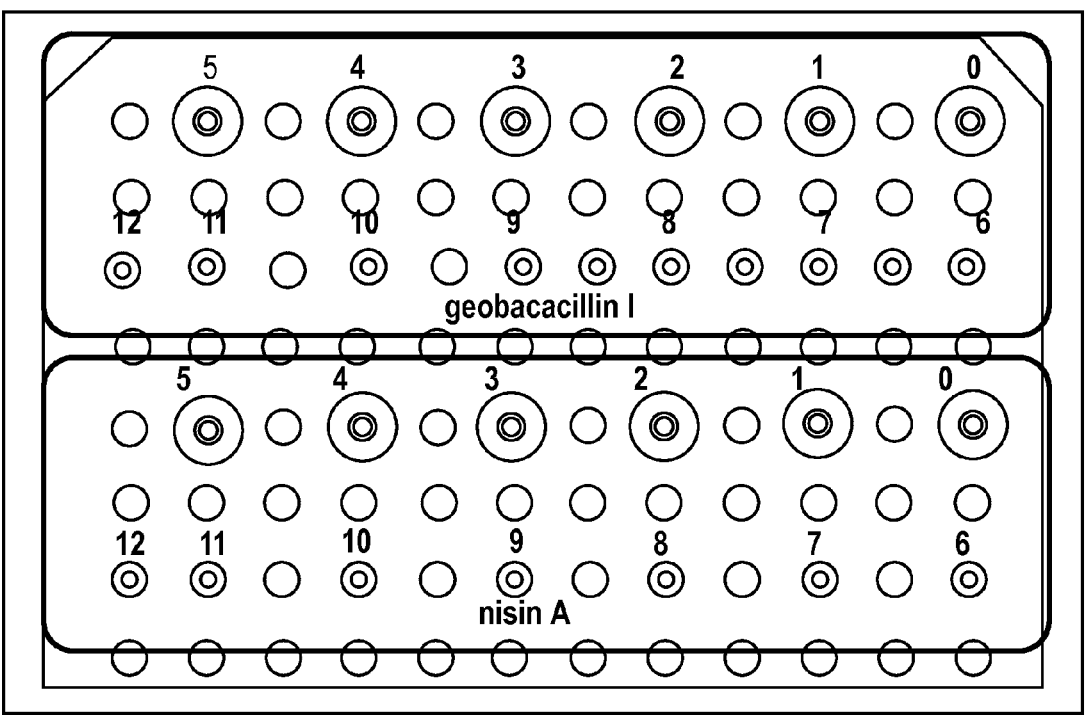
FIG. 15 shows an agar diffusion growth inhibition assay with $B.$ $subtilis$ 6633 to determine the relative stabilities of geobacillin I and nisin A at pH 8.0 and 60° C.
Figure 16:
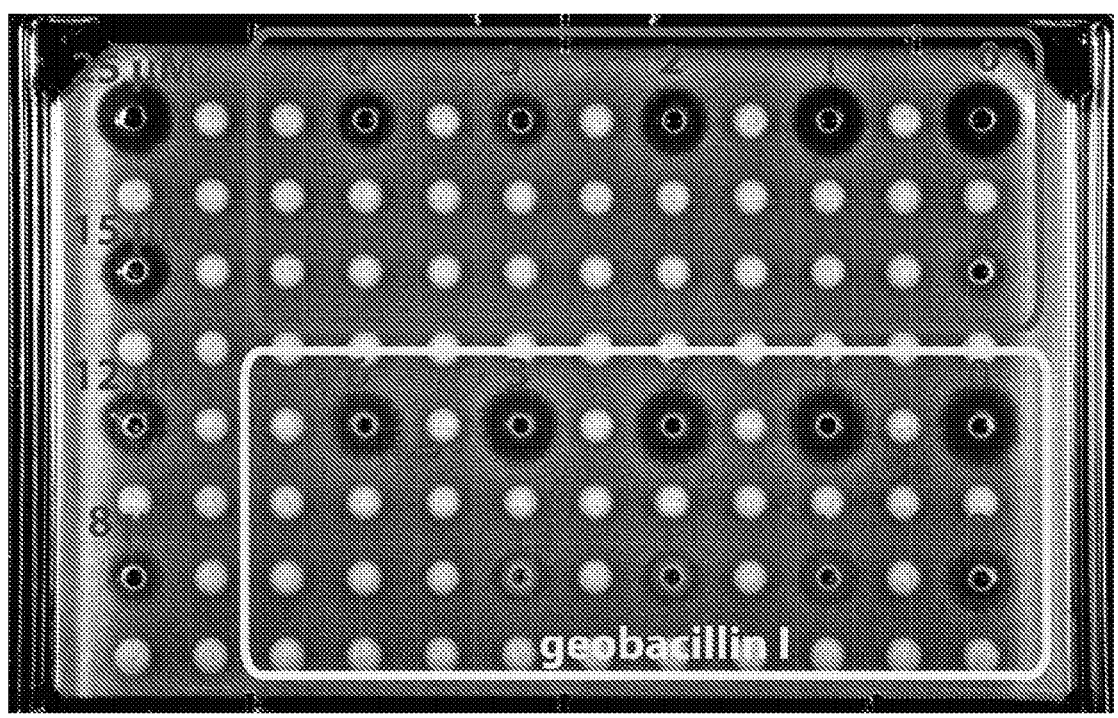
FIG. 16 shows an agar diffusion growth inhibition assay with $B.$ $subtilis$ 6633 to determine the relative stabilities of geobacillin I and nisin A at pH 7.0 and 37° C.
Figure 17:
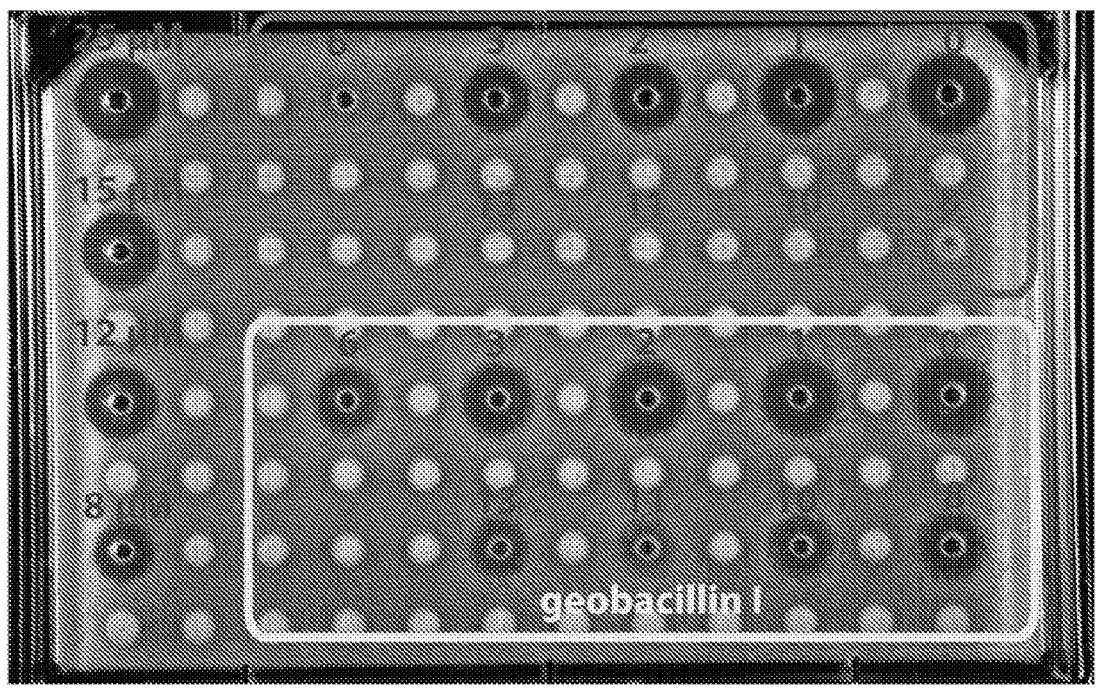
FIG. 17 shows agar diffusion growth inhibition assay with $B.$ $subtilis$ 6633 to determine the relative stabilities of geobacillin I and nisin A at pH 8.0 and 37° C.

Geobacillin II is shown in FIG. 13B (SEQ ID NO:53). Geobacillin II has 4 rings labeled A-D. All of these rings are formed by lanthionine residues (Ala-S-Ala), including one in ring A ($Ala_1$-S-$Ala_5$) ring B ($Ala_7$-S-$Ala_{11}$), one in ring C ($Ala_{14}$-S-$Ala_{18}$), and one in ring D ($Ala_{20}$-S-$Ala_{25}$). The molecule is amenable to amino acid substitutions and variants with amino acid substitutions are expected to result in biologically active molecules.

In one embodiment of the invention, geobacillin II has one, two or all three of the following mutations; Ala1Abu, Dhb2Ala, Ile3Arg. Geobacillin II having mutations Ala1Abu, Dhb2Ala, and Ile3Arg is geobacillin II S1T, which potentially has greater solubility and improved stability over wild-type geobacillin II.

The amino acid sequence of wild-type geobacillin II, prior to post-translational modification is MKGGIQMEKQEQT-FVSKISEEELKKLAGGYTEVSPQS-TIVCVSLRICNWSLRFCPSFKVRCPM (SEQ ID NO:5). Optionally, the Q at position 36 is a K. 1, 2, 3, 4, 5, 6, 7, 8, 9, 10, 11, 12, 13, 14, 15, 20, 25, 30 or more (or any range of amino acids between about 1 and 30 amino acids) can be added to the wild-type or mutant geobacillin. Additionally, about 30, 25, 20, 15, 14, 13, 12, 11, 10, 9, 8, 7, 6, 5, 4, 3, 2, 1, or less (or any range of between about 30 and 1 amino acids) amino acids can be added to the wild-type or mutant geobacillin. For example, in one embodiment of the invention a geobacillin has the following amino acid sequence: GSSHH-HHHHSQDPMKGGIQMEKQEQTFVSKI-SEEELKKLAGGYTEVSPQSTIVCVSL-RICNWSLRFCPSFKVRCPM (SEQ ID NO:64), which is the same as SEQ ID NO:5, but has additional amino acids from the use of a vector to produce the geobacillin. Optionally, the Q at position 49 is a K. The sequence of geobacillin II after the leader is cleaved and prior to other post-translational modification is STIVCVSLRICNWSLRFCPSFKVRCPM (SEQ ID NO:65). The leader sequence of geobacillin II is MKGGIQMEKQEQTFVSKISEEELKKLAGGYTEVSPQ (SEQ ID NO:6). Optionally, the Q at position 36 is a K.

Variant geobacillin polypeptides have one or more conservative amino acid variations or other minor modifications and retain biological activity, i.e., are biologically functional equivalents. A biologically active equivalent has substantially equivalent function when compared to the corresponding wild-type geobacillin at 37° C. In one embodiment of the invention a geobacillin has about 1, 2, 3, 4, or 5 or less conservative amino acid substitutions. A variant geobacillin or geobacillin exposed to varying conditions (e.g., different buffers, temperature, different additives, etc.) can have 80, 85, 90, 95% or more biological activity of a wild-type geobacillin at 37° C., in phosphate buffer.

Variant geobacillins are part or the invention and are at least about 80%, or about 81, 82, 83, 84, 85, 86, 87, 88, 89, 90, 91, 92, 93, 94, 95, 96, 97, 98, or 99% identical to any of the geobacillin sequences disclosed herein. For example, a variant geobacillin can have about 1, 2, 3, 4, 5, 6, 7, 8, 9, 10 or more amino acid changes. In one embodiment of the invention a polypeptide has about 1, 2, 3, 4, 5, 6, 7, 8, 9, 10 or less conservative amino acid substitutions.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variant geobacillins can generally be identified by modifying one of the geobacillin sequences of the invention, and evaluating the properties of the modified geobacillin to determine if it is a biological equivalent. A variant is a biological equivalent if it reacts substantially the same as a geobacillin of the invention in an assay such as a zone of inhibition assay or a minimum inhibitory concentration assay, e.g. has 1 to 10 or more fold more activity than the original geobacillin.

A conservative substitution is one in which an amino acid is substituted for another amino acid that has similar properties, such that one skilled in the art of peptide chemistry would expect the secondary structure and general nature of the polypeptide to be substantially unchanged. In general, the following groups of amino acids represent conservative changes: (1) ala, pro, gly, glu, asp, gln, asn, ser, thr, dha, abu, dhb; (2) cys, ser, tyr, thr; (3) val, ile, leu, met, ala, phe, dha, dhb, abu, dhb, gly; (4) lys, arg, his; and (5) phe, tyr, trp, his.

A geobacillin polypeptide can be covalently or non-covalently linked to an amino acid sequence to which the geobacillin is not normally associated with in nature, i.e., a heterologous amino acid sequence. A heterologous amino acid sequence can be from a non-*Geobacillus thermodenitrificans* organism, a synthetic sequence, or a *Geobacillus thermodenitrificans* sequence not usually located at the carboxy or amino terminus of a geobacillin of the invention. Additionally, a geobacillin can be covalently or non-covalently linked to compounds or molecules other than amino acids such as indicator reagents. A geobacillin can be covalently or non-covalently linked to an amino acid spacer, an amino acid linker, a signal sequence, a stop transfer sequence, TMR stop transfer sequence, a transmembrane domain, a protein purification ligand, or a combination thereof. A polypeptide can also be linked to a moiety that facilitates purification (e.g., affinity tags such as a six-histidine tag, trpE, glutathione-S-transferase, maltose binding protein, staphylococcal Protein A or com), or a moiety that facilitates polypeptide stability (e.g., polyethylene glycol; amino terminus protecting groups such as acetyl, propyl, succinyl, benzyl, benzyloxycarbonyl or t-butyloxycarbonyl; carboxyl terminus protecting groups such as amide, methylamide, and ethylamide). In one embodiment of the invention a protein purification ligand can be one or more amino acid residues at, for example, the amino terminus or carboxy terminus of a polypeptide of the invention. An amino acid spacer is a sequence of amino acids that are not associated with a polypeptide of the invention in nature. An amino acid spacer can comprise about 1, 5, 10, 20, 100, or 1,000 amino acids.

If desired, a geobacillin of the invention can be part of a fusion protein, which can contain heterologous amino acid sequences. Heterologous amino acid sequences can be present at the C or N terminus of a geobacillin of the invention to form a fusion protein. More than one geobacillin of the invention can be present in a fusion protein. Fragments of geobacillins of the invention can be present in a fusion protein of the invention. A fusion protein of the invention can comprise one or more geobacillins of the invention, fragments thereof, or combinations thereof.

Geobacillin polypeptides of the invention can be in a multimeric form. That is, a geobacillin polypeptide can comprise one or more copies of a geobacillin polypeptide of the invention or a combination thereof. A multimeric geobacillin polypeptide can be a multiple antigen peptide (MAP). See e.g., Tam, J. Immunol. Methods, 196:17-32 (1996).

Pharmaceutically acceptable salts, esters, amides, and prodrugs are carboxylate salts, amino acid addition salts, esters, amides, and prodrugs of the geobacillins are part of the present invention. These compounds are suitable for use with subjects and do not cause undue toxicity, irritation, or allergic response, are commensurate with a reasonable benefit/risk ratio, and are effective for their intended use. Salts are the substantially non-toxic, inorganic and organic acid addition salts of geobacillins of the invention. Salts include, for example, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like.

Pharmaceutically acceptable, non-toxic esters of geobacillins include, for example, $C_1$-$C_6$ alkyl esters wherein the alkyl group is a straight or branched chain. Other esters include $C_5$-$C_7$ cycloalkyl esters as well as arylalkyl esters such as, but not limited to benzyl $C_1$-$C_4$ alkyl esters.

Pharmaceutically acceptable, non-toxic amides of geobacillins include amides derived from ammonia, primary $C_1$-$C_6$ alkyl amines and secondary $C_1$-$C_6$ dialkyl amines wherein the alkyl groups are straight or branched chains. In the case of secondary amines, the amine may be in the form of a 5- or 6-membered heterocycle containing one nitrogen atom. Also included are amides derived from ammonia, $C_1$-$C_3$ alkyl primary amines, and $C_1$-$C_2$ dialkyl secondary amines.

A geobacillin of the invention can be produced recombinantly. A polynucleotide encoding a geobacillin of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. A geobacillin can also be chemically synthesized or purified from *Geobacillus thermodenitrificans* cell culture. See, e.g., U.S. 61/406,194, filed Oct. 25, 2010; Shi et al., J. Am. Chem. Soc. 133: 2338 (2011).

In one embodiment of the invention a geobacillin is produced by inserting a trypsin or other enzyme cleavage site within 10 nucleotides (upstream or downstream) of the −1 position of a nucleic acid molecule encoding GeoA1 to make a mutated GeoA1 nucleic acid molecule. The mutated GeoA1 nucleic acid molecule and nucleic acid molecules that encode GeoB, GeoC GeoAII, and GeoM placed into one or more cloning vectors. A culture of bacterial cells are transformed with the one or more cloning vectors. Once the transformed cells are expressing proteins from the cloning vectors, the transformed bacterial cells are lysed and the cell lysate is collected. The cell lysate is treated with trypsin or another enzyme that act on the cleavage site of GeoA1. The geobacillin is isolated from the cell lysate to produce an isolated geobacillin. The nucleic acid molecules encoding GeoA1 GeoB, GeoC GeoAII, and GeoM can be codon optimized for expression in the bacterial cells. The bacterial cells can be, for example *Escherichia coli*.

In one embodiment of the invention the A ring of a geobacillin (the first ring from the amino terminus) has LL (2R,6R) stereochemistry or has a mixture of LL stereochemistry and DL-stereochemistry (2R,6R and 2S,6R).

Compositions

The geobacillins of the invention can act as antimicrobials, disinfectants, antibiotics, antiseptics, preservatives, or decontaminating agents. An antimicrobial composition kills microbes or slows the reproduction of microbes such as bacteria. A disinfectant composition is applied to a non-living object to kill microbes or to slow the reproduction of microbes such as bacteria. An antibiotic kills microbes or slows the reproduction of microbes, such as bacteria, in the body of a subject or in cells or tissues. An antiseptic kills microbes or slows the reproduction of microbes, such as bacteria, on skin, tissue or organs. A preservative composition kills microbes or slows the reproduction of microbes in products such as paints, wood, foods, beverages, biological samples, cell or tissue cultures or pharmaceutical compositions to prevent decomposition by microbes such as bacteria. A decontaminating agent is a cleaning agent that can be used to kill microbes or to reduce the reproduction of microbes, such as bacteria, in or on a living organism, cells, tissues, or objects.

The geobacillins of the invention can be bacteriostatic, meaning that the geobacillins reduce or prevent the reproduction of bacteria. In one embodiment of the invention the bacteriostatic action of a geobacillin reduces reproduction of the bacteria by about 5, 10, 20, 30, 40, 50, 60, 70, 80, 90, or 100% (or any range between about 5% and 100%). The geobacillins of the invention can be bacteriocidal, meaning that the geobacillins kill bacteria. In one embodiment of the invention the geobacillins kill about 5, 10, 20, 30, 40, 50, 60, 70, 80, 90, or 100% (or any range between about 5% and 100%) of the bacteria they come in contact with. The difference between whether a geobacillin acts as bacteriostatic agent or a bacteriocidal agent can be the amount or concentration of geobacillin delivered to the subject, composition, or object. Geobacillins can reduce the numbers of bacteria present in a composition, subject, cells, or tissues. In one embodiment of the invention geobacillins reduce the number of bacteria by about 5, 10, 20, 30, 40, 50, 60, 70, 80, 90, or 100% (or any range between about 5% and 100%).

The isolated geobacillins of the invention can be present in antimicrobial compositions comprising one or more isolated geobacillins of the invention and one or more pharmaceutically acceptable carriers, diluents or excipients (solids or liquids). In one embodiment of the invention the geobacillin is present in an amount effective to substantially reduce bacterial reproduction of at least one type of Gram-positive bacteria by about 5, 10, 20, 30, 40, 50, 60, 70, 80, 90 or 100% (or any range between about 5 and 100%). In one embodiment of the invention the geobacillin is present in an amount effective to substantially reduce the numbers of at least one type of Gram-positive bacteria by about 5, 10, 20, 30, 40, 50, 60, 70, 80, 90 or 100% (or any range between about 5 and 100%). Gram-positive bacteria can be, for example, *Streptococcus*, such as *Streptococcus dysgalatiae* subsp *dysgalactiae*, *Enterococcus* such as *Enterococcus faecium* and vancomycin resistant *Enterococcus faecium, Staphylococcus*, such as *Staphylococcus aureus, Staphylococcus epidermidis* 15X, *Staphylococcus epidermidis*, and methicillin resistant *Staphylococcus aureus, Bacillus*, such as *Bacillus anthracis* Sterne 7702, *Bacillus subtilis*, and *Bacillus cereus* Z4222, *Clostridium* such as *Clostridium difficile*, and *Listeria* such as *Listeria monocytogenes*.

Furthermore, Gram negative bacteria can be susceptible to geobacillins of the invention where the outer membrane is disrupted with, for example, a chelating agent such as EDTA. The combination of geobacillins of the invention with a membrane disruption agent and/or other antibiotics or drugs that target Gram negative species can provide a composition effective against both Gram positive and Gram negative species. Therefore, the invention includes compositions comprising one or more geobacillins of the invention and at least one additional antimicrobial agent or membrane disrupting agent. The one additional antimicrobial agent can have Gram negative bacteriostatic or bacteriocidal activity. The membrane disrupting agent can render Gram negative bacteria susceptible to a geobacillin (i.e., the membrane disrupting agent in combination with one or more geobacillins of the invention are bacteriostatic or bacteriocidal to Gram negative bacteria). Gram negative bacteria include, for example, *Bordatella pertussis, Borrelia burgdorferi, Brucella abortus, Brucella canis, Brucella melitensis, Brucella suis, Campylo-*

*bacter jejuni, Escherichia coli, Francisella tularensis, Haemophilus influenza, Helicobacter pylori, Legionella pneumophila, Leptospira interrogans, Neisseria gonorrhoeae, Neisseria meningitides, Pseudomonas aeruginosa, Rickettsia rickettsii, Salmonella typhi, Salmonella typhimurium, Shigella sonnei, Treponema pallidum, Vibrio cholera,* and *Yersinia pestis*.

Gram variable and Gram indeterminate bacteria can also be susceptible to geobacillins of the invention. Chelating agents such as EDTA can be added to compositions of the invention to disrupt the outer membrane of these organisms. Gram variable and Gram indeterminate bacteria include, for example, *Chlamydia pneumoniae, Chlamydia trachomatis, Chlamydia psittaci, Mycobacterium leprae, Mycobacterium tuberculosis, Mycobacterium ulcerans*, and *Mycoplasma pneumoniae.*

In one embodiment of the invention, geobacillin II is present in the amount effective to substantially reduce the numbers of at least one type of *bacillus* sp. By about 5, 10, 20, 30, 40, 50, 60, 70, 80, 90 or 100% (or any range between about 5% and 100%). At least one type of *bacillus* sp. can be for example, *Bacillus subris, Bacillus cereus, Bacillus subtilis, Bacillus anthracis, Bacillus amyloliquefaciens, Bacillus thuringiensis, B. coagulans, B. licheniformis, B. brevis, B. stearothermophilus, B. weihenstephanensis* and, *B. halodurans.*

A geobacillin of the invention is retains 80%, 90%, 95% or more biological activity at, for example about 37° C., 45° C., 55° C., 65° C., 75° C., 80° C., 90° C., 100° C., or greater than 100. A geobacillin of the invention retains 80%, 90%, 95% or more biological activity at, for example, 37° C. to 100° C. or and any range between about 37° C. to 100° C., for example 37° C. to 80° C., 55° C. to 80° C., or 65° C. to 80° C. A geobacillin of the invention is stable and retains stability in phosphate buffer. Geobacillins retains even more stability in MOPS buffer, that is a buffer comprising about 0.01, 0.5, 0.75, 0.1, 0.25 M 3-(N-morpholino)propanesulfonic acid at a pH of about 6.5 to 7.9. In one embodiment of the invention a geobacillin is in a MOPS buffer comprising about 0.01, 0.5, 0.75, 0.1, or 0.25 M 3-(N-morpholino)propanesulfonic acid at a pH of about 6.5 to 7.9

A geobacillin of the invention can be combined with one or more pharmaceutically acceptable carriers, other carriers, diluents, adjuvants, excipients or encapsulating substances, which are suitable for administration to an animal, composition, or object. Exemplary pharmaceutically acceptable carriers, other carriers, diluents, adjuvants, excipients or encapsulating substances thereof include sugars, such as lactose, glucose, dextrose, and sucrose; starches, such as corn starch and potato starch; cellulose and its derivatives, such as sodium carboxymethyl cellulose, ethyl cellulose, hydropropylmethylcellulose, and methyl cellulose; polysaccharides such as latex functionalized SEPHAROSE® (crosslinked, beaded-form of agarose) and agarose; powdered tragacanth; glycerol; malt; gelatin; talc; solid lubricants, such as stearic acid and magnesium stearate; calcium sulfate; vegetable oils, such as peanut oil, cottonseed oil, sesame oil, olive oil, and corn oil; polyols such as propylene glycol, glycerine, sorbitol, mannitol, propylene glycol, and polyethylene glycol; proteins such as serum albumins, keyhole limpet hemocyanin, immunoglobulin molecules, thyroglobulin, ovalbumin, tetanus toxoid; alginic acid; emulsifiers, such as the TWEEN®s (polysorbate); polylactic acids; polyglycolic acids; polymeric amino acids such as polyglutamic acid, and polylysine; amino acid copolymers; peptoids; lipitoids; inactive avirulent virus particles or bacterial cells; liposomes; hydrogels; cyclodextrins; biodegradable nanocapsules; bioadhesives; wetting agents, such sodium lauryl sulfate; coloring agents; flavoring agents; tableting agents; stabilizers; antioxidants; preservatives; pyrogen-free water; isotonic saline; ethanol; ethyl oleate; pyrrolidone; Ringer's solution, dextrose solution, Hank's solution; sodium alginate; polyvinylpyrrolidone; gum tragacanth; gum acacia; and sterile water and aqueous buffers and solutions such as physiological phosphate-buffered saline.

Carriers, such as pharmaceutically acceptable carriers and diluents, for therapeutic use are well known in the art and are described in, for example, Remington's Pharmaceutical Sciences, Mack Publishing Co. (A. R. Gennaro ed. (1985)).

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates.

The geobacillin compositions can be in a form suitable for oral use, for example, as tablets, troches, lozenges, mouthwashes, dentifrices, buccal tablets, solutions, aqueous or oily suspensions, dispersible powders or granules, emulsions, hard or soft capsules, or syrups or elixirs. Such compositions can contain one or more agents, such as emulsifying agents, wetting agents, pH buffering agents, sweetening agents, flavoring agents, coloring agents and preserving agents. The geobacillin compositions can be a dry product for reconstitution with water or other suitable liquid before use.

Geobacillins of the invention can also be administered in the form of suppositories for rectal, vaginal, or urethral administration of the drug. These compositions can be prepared by mixing the geobacillin with a suitable non-irritating carrier that is solid at ordinary temperatures but liquid at the body temperature and will therefore melt in the rectum to release the drug. Such materials are cocoa butter and polyethylene glycols.

Geobacillins can also be topically administered in the form of, e.g., lotions, gels, or liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other dosage forms include, for example, injectable, sublingual, and nasal dosage forms. Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Formulations can contain between about 0.0001% and about 99.9999% by weight of one or more geobacillins of the invention and usually at least about 5, 10, 15, 20, 25, 30, 40, 50, 60, 70, 80, 90, or 100% (weight %) of one or more geobacillins of the present invention. Some embodiments contain from about 25% to about 50% or from 5% to 75% of a geobacillin of invention.

One or more geobacillins of the invention can be combined with one or more antimicrobials, antibiotics, bacteriocins, anti-viral, virucidal, or anti-fungal compounds or molecules to form a composition useful in the methods of the invention. Antibiotics include, for example, penicillins, cephalosporins, polymyxins, quinolones, sulfonamides, aminoglycosides, macrolides, tetracyclines, cyclic lipopeptides (e.g., daptomycin), glycylcyclines (e.g., tigecycline), and oxazolidinones (e.g., linezoid).

Bacteriocins include, for example, acidocin, actagardine, agrocin, alveicin, aureocin, carnocin, carnocyclin, colicin, curvaticin, divercin, duramycin, enterocin, enterolysin, epidermin, erwiniocin, gallidermin, glycinecin, halocin, haloduracin, lactococin, lacticin, leucoccin, macedocin, mersacidin, mesentericin, microbisporicin, mutacin, nisin, paenibacillin, planosporicin, pediocin, pentocin, plantaricin, reuterin, sakacin, salivaricin, subtilin, sulfolobicin, thuricin 17, trifolitoxin, variacin, vibriocin, warnericin, and warnerin. Antifungals include, for example, polyene antifungals (e.g., amphotericin B, natamycin, rimocidin, filipin, nystatin, candicin, hamycin), azole antifungals (e.g., imidazole, triazole, thiazole), imidazoles (e.g., miconazole, ketoconazole, clotrimazole, econazole, omoconazole, bifonazole, butoconazole, fenticonazole, isoconazole, oxiconazole, sertaconazole, sulconazole, tioconazole), triazoles (e.g., fluconazole, itraconazole, isavuconazole, ravuconazole, posaconazole, voriconazole, terconazole, albaconazole), thiazoles (e.g., abagungin), allylamines (e.g., terbinafine, naftifine, butenafine), echinocandins (e.g., anidulafungin, caspofungin, micafungin), polygodial, benzoic acid, ciclopiroxolamine, tolnaftate, undecylenic acid, flucytosine, and griseofulvin.

Antivirals and virucidal agents include, for example, abacavir, aciclovire, acyclovir, adefovir, amantadine, amprenavir, ampligen, arbidol, atazanavir, atripla, boceprevir, cidofovir, combivir, delavirdine, didanosine, docosanol, efavirenz, emtricitabine, enfuvirtide, entecavir, entry inhibitors, famciclovir, fomivirsen, fosamprenavir, foscarnet, fosfonet, ganciclovir, ibacitabine, imunovir, idoxuridine, imiquimod, indinavir, inosine, integrase inhibitor, interferon types i, ii, iii, interferon, lamivudine, lopinavir, loviride, maraviroc, moroxydine, methisazone, nelfinavir, nevirapine, nexavir, nucleoside analogues, oseltamivir, peginterferon alpha-2a, penciclovir, peramivir, pleconaril, podophyllotoxin, protease inhibitor, raltegravir, reverse transcriptase inhibitor, ribavirin, rimantadine, ritonavir, pyramidine, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

Use of Geobacillins of the Invention

Geobacillin compositions of the invention can be used to reduce the growth of bacteria, prevent the growth of bacteria, prevent the reproduction of bacteria, reduce the reproduction of bacteria, or to reduce or eliminate the numbers of bacteria present in or on an object, composition or subject. In one embodiment of the invention, the bacteria are at least one type of Gram positive bacteria, at least one type of Gram negative bacteria, at least one type of Gram variable or Gram indeterminate bacteria, or a combination of at least one type of Gram positive or at least one type of Gram negative bacteria or at least one type of Gram variable or Gram indeterminate bacteria. The geobacillin compositions of the invention can be administered to, added to, or contacted with a composition or subject.

Geobacillins of the invention can be used to treat, ameliorate, or prevent a disease, infection, or colonization. A disease is a pathological condition of a part, organ, or system of an organism resulting from infection and characterized by an identifiable group of signs and symptoms. An infection is invasion by and multiplication of pathogenic microorganisms, such as bacteria, in a bodily part or tissue, which may produce a subsequent tissue injury and progress to overt disease through a variety of cellular or toxic mechanisms. Colonization is the act or process of a microorganism, such as bacteria, establishing itself on or within a host or object. Colonization may produce a subsequent biofilm or biofouling condition as described below. Geobacillins of the invention can be used prophylactically to prevent disease, infection or colonization or to prevent the spread of a disease, infection or colonization to additional bodily parts or tissues, additional surfaces, or to different subjects. Geobacillins of the invention can also be used to reduce the number of pathogenic microorganisms on or in a subject or on a surface.

Examples of diseases, infections and colonizations that can be treated or prevented by the compositions and methods of the invention include, for example, septicemia, bacterial meningitis, cystic fibrosis, bovine mastitis, impetigo, bacterial vaginosis, bacterial pneumonia, urinary tract infections, bacterial gastroenteritis, erysipelas, cellulitis, anthrax, whooping cough, brucellosis, enteritis, opportunistic infections, community acquired respiratory infections, upper and lower respiratory infections, diphtheria, nosocomial infections, diarrhea, ulcer, bronchitis, listeriosis, tuberculosis, gonorrhea, pseudomonas infections, salmonellosis, shigellosis, staphylococcal infections, streptococcal infections, and necrotizing fasciitis.

Geobacillins of the invention can be administered to a mammal, such as a mouse, rabbit, guinea pig, macaque, baboon, chimpanzee, human, cow, sheep, pig, horse, dog, cat, or to a non-mammalian animal such as a chicken, duck, or fish. Geobacillins of the invention can also be administered to plants.

Administration of the geobacillins of the invention can be by any means known in the art, including injection (e.g., intramuscular, intravenous, intrapulmonary, intradermal, intraperitoneal, intrathecal, or subcutaneous injection), aerosol, intranasal, infusion pump, suppository (rectal, vaginal, urethral), mucosally, topically, buccally, orally, parenterally, infusion techniques, by inhalation or spray, sublingually, transdermally, as an ophthalmic solution, intraspinal application, or by other means, in dosage unit formulations containing conventional non-toxic pharmaceutically acceptable carriers, diluents, excipients, adjuvants, and vehicles. A combination of administration methods can also be used.

In therapeutic applications, the geobacillin compositions of the invention are administered to subjects to reduce the reproduction of bacteria or reduce the numbers of bacteria, or both. The particular dosages of geobacillin in a composition will depend on many factors including, but not limited to the species, age, gender, severity of infection, concurrent medication, general condition of the animal to which the composition is administered, and the mode of administration of the composition. An effective amount of the composition of the invention can be readily determined using only routine experimentation. A therapeutically effective amount means the administration of that amount to an individual, either in a single dose or as part of a series, which is effective for treatment, amelioration, or prevention of bacterial infection or colonization. A therapeutically effective amount is also an amount effective in alleviating or reducing the symptoms of an infection or in reducing the reproduction of bacteria in or on a subject or reducing the amount of bacteria in or on a subject.

The concentration of geobacillin in a composition can vary widely, and will be selected primarily based on activity of the geobacillin, body weight of the subject, overall health of the subject, etc. as described above, in accordance with the particular mode of administration selected and the subject's needs. Concentrations, however, will typically be selected to provide dosages ranging from about 0.001, 0.01, 0.1, 1, 5, 10, 20, 30, 40, 50, 75, 100, 150 mg/kg/day (or any range between about 0.001 and 150 mg/kg/day) and sometimes higher. Typical dosages range from about 0.1 mg/kg/day to about 5 mg/kg/day, from about 0.1 mg/kg/day to about 10 mg/kg/day, from about 0.1 mg/kg/day to about 20 mg/kg/day, and from about 0.1 mg/kg/day to about 50 mg/kg/day.

Geobacillins can be administered for a certain period of time (e.g., 1 day, 3 days, 1 week, 1 month, 2 months, 3 months, 6 months, 1 year or more) or can be administered in maintenance doses for long periods of time to prevent or reduce disease, infection, colonization, biofilms or biofouling conditions.

Geobacillins of the invention can be administered either to an animal that is not infected or colonized with bacteria or can be administered to bacterial infected or colonized animal.

One embodiment of the invention provides a method for decontaminating or reducing bacterial growth on or in an inanimate object comprising contacting the object with a geobacillin of the invention for a period effective to substantially inhibit bacterial growth of at least one type of bacteria. The contacting can be for 1, 15, 30, or 60 minutes, or 2, 3, 10, 12, 24, 36 or 48 hours (or any range between about 1 minute and 48 hours). An object can be, for example, a food preparation surface, food preparation equipment, industrial equipment, pipes, or a medical device such as catheter, scalpel, knife, scissors, spatula, expander, clip, tweezers, speculum, retractor, suture, surgical mesh, chisel, drill, level, rasp, saw, splint, caliper, clamp, forceps, hook, lancet, needle, cannula, curette, depressor, dilator, elevator, articulator, extractor, probe, staple, artificial joint, wound dressing, catheter, stent, tubing, bowl, tray, sponge, snare, spoon, syringe, pacemaker, screw, plate, pin, wire, guide wire, pacemaker lead, implant, sensor, glucose sensor, blood bypass tubing, i.v. bag, ventricular assist device components, and balloon.

Methods of the invention can also be used to ameliorate, reduce, remove, or prevent biofouling or biofilms. Biofouling is the undesirable accumulation of microorganisms, such as bacteria on structures exposed to solvent. Biofouling can occur, for example on the hulls of ships, in membrane systems, such as membrane bioreactors and reverse osmosis spiral wound membranes, water cooling systems of large industrial equipment and power stations, and oil pipelines carrying, e.g., used oils, cutting oils, soluble oils or hydraulic oils.

A biofilm can cause biofouling and is an aggregate of organisms wherein the organisms are adhered to each other, to a surface, or a combination thereof. A biofilm can comprise one or more species of bacteria, fungi, filamentous fungi, yeasts, algae, cyanobacteria, viruses, and protozoa and combinations thereof. Microorganisms present in a biofilm can be embedded within a self-produced matrix of extracellular polymeric substances. When a microorganism switches to a biofilm mode of growth, it can undergo a phenotypic shift in behavior wherein large suites of genes are differentially regulated. Nearly every species of microorganism can form biofilms. Biofilms can be found on or in living organisms or in or on non-living structures. Biofilms can be present on structures contained in naturally occurring bodies of water or man-made bodies of water, on the surface of water, surfaces exposed to moisture, interiors of pipes, cooling water systems, marine systems, boat hulls, on teeth, on plant surfaces, inside plants, on human and animal body surfaces, inside humans and animals, on contact lenses, on catheters, prosthetic cardiac valves, other prosthesis, intrauterine devices, and other structures/devices.

Biofilms can cause corrosion of metal surfaces, inhibit vessel speed, cause plant diseases, and can cause human and animal diseases. Biofilms are involved in human and animal infections, including, for example, urinary tract infections, catheter infections, middle-ear infections, dental plaque, gingivitis, dental decay and gum disease, endocarditis, infections in cystic fibrosis, chronic sinusitis, and infections of permanent indwelling devices such as joint prostheses and heart valves. Biofilms can also impair cutaneous wound healing and reduce topical antibacterial efficiency in healing or treating infected skin wounds.

Some microorganisms that can form biofilms, cause biofouling and/or cause disease in humans and animals include, for example, bacteria, fungi, yeast, algae, protozoa, and viruses as described above. Biofilms can be treated in living organisms as described above. Biofilms and biofouling conditions on non-living surfaces can be treated by applying the geobacillins of the invention onto the non-living surface or to the area surrounding the surface. Geobacillins can also be added to the water, oil, or other fluid surrounding and in contact with the non-living surface.

The invention provides methods of ameliorating or preventing a biofouling condition or a biofilm condition, caused by one or more microorganisms, such as bacteria. The methods comprise administering one or more geobacillins to the biofouling condition or biofilm condition, wherein the biofouling condition or biofilm condition is ameliorated.

One or more geobacillins can be administered to a surface that has a biofilm or biofouling condition or can be administered to a surface as a prophylactic measure. The geobacillins can be in a dried form (e.g., lyophilized or tablet form) or a liquid solution or suspension form. The dried or liquid forms can be swabbed, poured, sprayed, flushed through the surface (e.g., pipes or membranes) or otherwise applied to the surface. Geobacillins can be present in a composition with a carrier or diluent in an amount from about 0.001, 0.01, 0.1, 1, 5, 10, 20, 30, 40, 50, 75, 100, 150 mg/m$^2$ (or any range between about 0.001 and about 150 mg/m$^2$ and sometimes higher.

Where the biofilm is present or potentially present on an artificial surface within a human or animal (e.g., a catheter or medical device), the artificial surface can be contacted with the one or more geobacillins prior to insertion into the human or animal. Optionally, the geobacillins can be delivered to the surface after the artificial surface is inserted into the human or animal.

In one embodiment of the invention, a geobacillin can be used for decontaminating or reducing bacterial reproduction or bacterial numbers in a biological tissue or cell culture. The geobacillin can be present in a pharmaceutically acceptable carrier, diluent or excipient at the dosage rates as for pharmaceutical compositions described above. The geobacillin or geobacillin composition can be contacted with the tissue or cell culture for a period effective to substantially inhibit bacterial growth of at least one type of gram-positive bacteria. The geobacillin can be provided in an amount effective to maintain the physiological characteristics of the biological tissue or cells and/or in an amount effective to substantially maintain the viability of the biological tissue or cells.

One embodiment of the invention provides a method for preparing isograft organs, tissues or cells, autograft tissues or cells, allograft organs, tissues or cells, xenograft organs, tissues or cells, or other cells or tissue for transplantation. The method comprises contacting the organs, cells or tissues with a geobacillin composition of the invention for a period effective to inhibit or reduce bacterial growth or bacterial numbers of at least one type of Gram-positive bacteria. The cells, organs or tissues can be, for example, a heart valve, a blood vessel, pericardium or musculoskeletal tissue, ligaments such as anterior cruciate ligaments, knee joints, hip joints, ankle joints, meniscal tissue, skin, cornea, heart, lung, small bowel, intestine, liver, kidney, bone marrow, bone, and tendons.

The contacting step can be performed at a temperature from about 2° C. to about 42° C. for about 0.5, 1, 2, 3, 5, 10, 24, 36, or 48 hours. The geobacillin composition can further comprise a physiological solution further comprising one or more broad spectrum antimicrobials and/or one or more antifungal agents, such as, for example vancomycin, imipenem, amikacin, and amphotericin B.

Geobacillin compositions of the invention can also be used as a preservative for allograft and xenograft process solutions, and cell culture and tissue solutions. The solutions can comprise an effective amount of one or more geobacillins in a physiological solution at a pH of between 3 and 8.

One or more geobacillins can be added to foods or beverages as a preservative. Examples of foods include, processed cheese products, pasteurized dairy products, canned vegetables, high moisture, hot baked flour products, pasteurized liquid egg, natural cheese products. Geobacillin can also be used to control listeria in foods, to control spoilage by lactic acid bacteria in, e.g., beer, wine, alcohol production and low pH foods such as salad dressings. Geobacillins can be used as an adjunct in food processing technologies such as higher pressure sterilization and electroporation. Geobacillins can be present in a food or beverages in an amount from about 0.001, 0.01, 0.1, 1, 5, 10, 20, 30, 40, 50, 75, 100, 150, 250, 500 mg/kg or mg/l (or any range between about 0.001 and about 500 mg/kg or mg/L and sometimes higher.

Kits

Compositions of the invention can be present in a kit comprising a container of one or more geobacillins of the invention. The geobacillins can be lyophilized and in the form of a lyophilized powder or tablet or can be in a solution or suspension optionally with buffers, excipients, diluents, adjuvants, or pharmaceutically acceptable carriers. A kit can also comprise one or more applicators for the one or more geobacillins to a body part or tissue or surface. The applicator can be, for example, a swab, a syringe (with or without a needle), a dropper, a sprayer, a surgical dressing, wound packing, or a bandage. Optionally, the kit can comprise one or more buffers, diluents, adjuvants, therapeutically acceptable carriers, or pharmaceutically acceptable carriers for reconstituting, diluting, or preparing the one or more geobacillins.

All patents, patent applications, and other scientific or technical writings referred to anywhere herein are incorporated by reference herein in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above.

EXAMPLES

Example 1

Description of Two Gene Clusters from *Geobacillus thermodenitrificans* NG80-2

For all examples DNA polymerases, restriction endonucleases, and T4 DNA ligase were purchased from New England Biolabs. All oligonucleotides were purchased from Integrated DNA Technologies. Media components for bacterial cultures were purchased from Difco laboratories. Chemicals were purchased from Sigma Aldrich unless noted otherwise. Endoproteinase GluC (sequencing grade) was purchased from Roche Biosciences. Trypsin (modified, sequencing grade) was purchased from Worthington Biosciences. Aminopeptidase was purchased from Sigma-Aldrich (ammonium sulfate suspension, L5006).

Figure 1C:
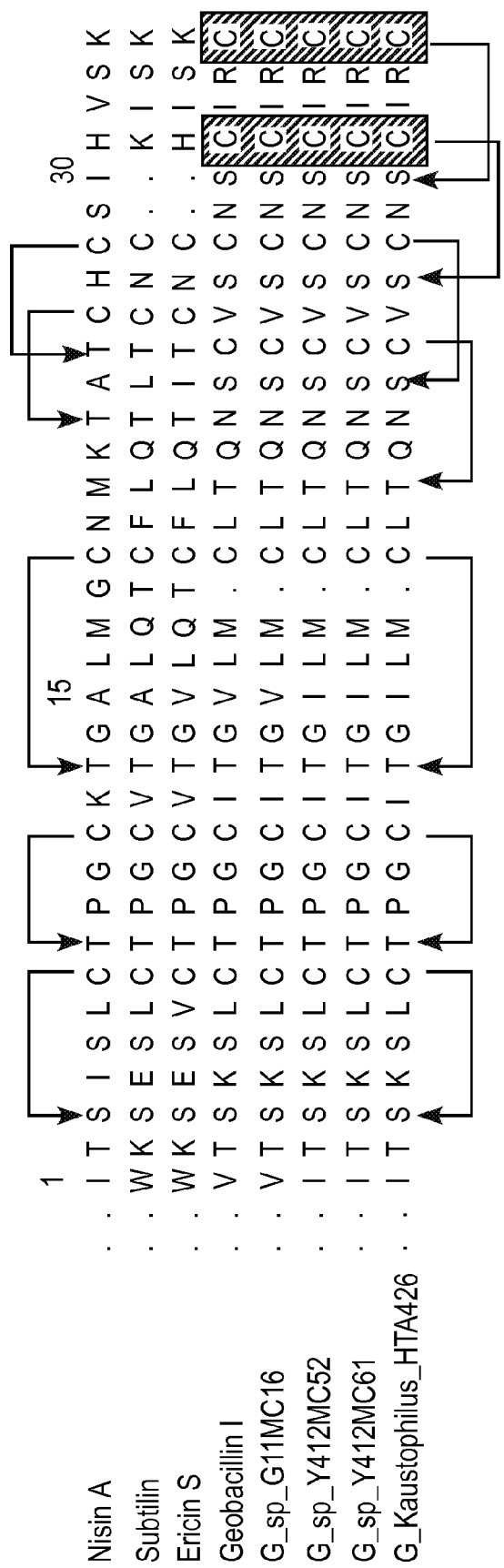
Figure 1D:
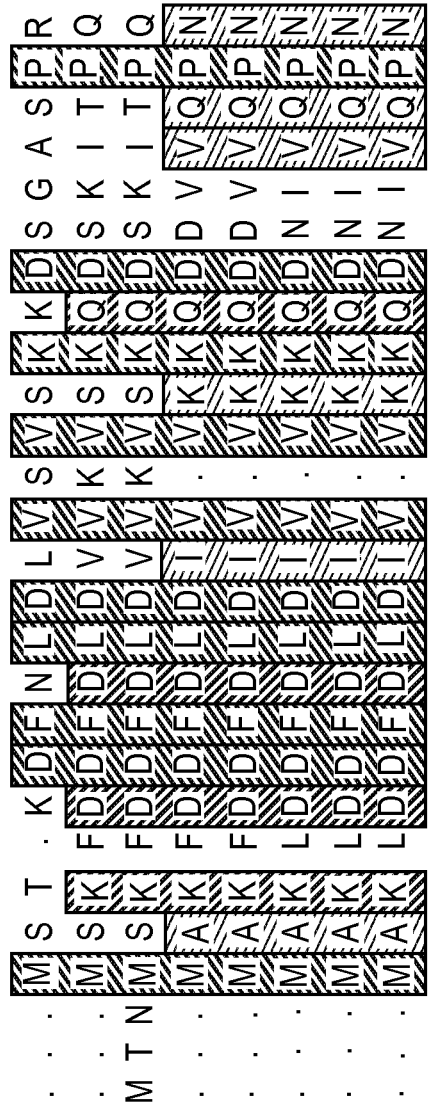

*Geobacillus thermodenitrificans* sp. are thermophilic Gram positive bacteria that have been found in diverse niches such as oil reservoirs, geothermal areas, and marine environments. They have gained recent interest as a potential source for industrially useful thermostable enzymes. *Geobacillus thermodenitrificans* NG80-2 was isolated from Dagang oil fields in China. Its genome was recently sequenced and two groups of genes were identified as lantibiotic biosynthetic gene clusters (17). The enzymes encoded in one cluster were annotated as homologs of the biosynthetic enzymes of the class I lantibiotic subtilin produced by *Bacillus subtilis* 6633, whereas the second cluster was anotated as having homology with the enzymes involved in biosynthesis of the class II lantibiotic mersacidin produced by *Bacillus* sp. HIL Y85, 54728 (17). Both clusters have also been noted in bioinformatic genome mining studies (18, 42), but the product of neither cluster is known. The clusters contain short open reading frames for the precursor peptides, which we designate geoAI for the class I cluster and geoAII for the class II cluster (FIG. 1A, B). The core peptide of the GeoAI precursor peptide has homology with nisin and subtilin, in particular in the N-terminal region. However, GeoAI has two more Cys residues than the precursor peptides for these known lantibiotics (FIG. 1C). The 23-residue leader peptide of GeoAI has high homology to the leader peptides for the lantibiotics ericin S and subtilin (FIG. 1D). On the basis of these sequence alignments, the site for proteolytic removal of the leader peptide was predicted as ProAsn↓Val (FIG. 1C,D); this prediction was confirmed by detection of the lantibiotic by colony mass spectrometry of other *Geobacillus* strains (vide infra).

Genes typically found in lantibiotic biosynthetic gene clusters are present downstream of geoAI including genes encoding a dehydratase (geoB), ABC transporter (geoT), cyclase (geoC), a two-component transcription regulator (geoR and geoK), and self-immunity proteins (geoI, geoG, geoE, and geoF) (FIG. 1A). Similar gene clusters with nearly identical precursor peptides (the only difference being a Val for Ile change) were also found in other genomes of *Geobacillus* (FIGS. 1C and D), but some of these clusters have frameshifted biosynthetic genes (18). No gene was identified that encodes for a typical class I lantibiotic protease to remove the leader peptide.

Figure 1E:
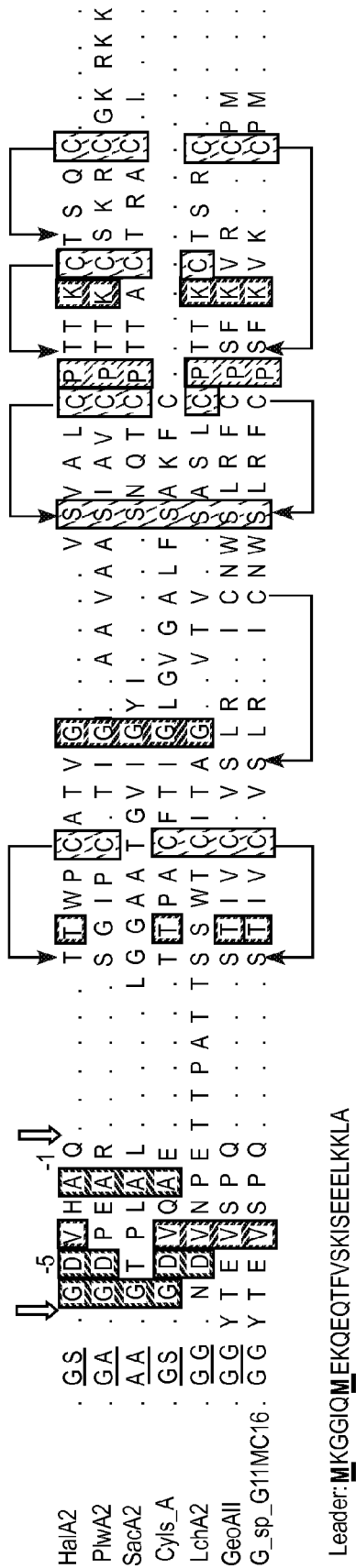

A search of the non-redundant protein database for homologs of the precursor peptide GeoAII did not find homologous precursor peptides of known lantibiotics suggesting it may be a novel class II lantibiotic. A gene encoding a precursor peptide differing in only one amino acid was found in the genome of *Geobacillus* sp. G11MC16 (FIG. 1E). Two start codons are present in frame at the N-terminus of the leader peptide preventing prediction of the initiation codon and resulting in two possible precursor peptides (FIG. 1E). GeoAII contains a typical double glycine motif for proteolytic removal of the leader peptide in class II lantibiotics (19, 20). Leader sequence removal after the double Gly site is supported by the presence of a gene product (GeoTII) that shows homology with the family of AMS (ABC transporter maturation and secretion) proteins whose peptide substrates share the double-glycine type cleavage site (20). Like other family members, GeoTII contains an N-terminal Cys protease domain for leader peptide removal. The class II lanthionine synthetase GeoM is encoded by a gene located next to geoAII and has about 35% sequence identity to known LanM enzymes such as MrsM, HalM1 and HalM2.

Example 2

Screening of *Geobacillus* Strains for Lantibiotic Production

We screened seven different *Geobacillus* strains (21) for production of the predicted geobacillins (*G. thermodenitrificans* DSM465, *G. thermodenitrificans* OHT-1, *Geobacillus* sp. M10EXG, *G. thermodenitrificans* OH2-1, *G. thermodenitrificans* OH5-2, *G. thermodenitrificans* NM16-2, and *G. kaustophilus* DSM7263). The strains were purchased from the *Bacillus* Genetic Stock Center. The strains were streaked on TBAB and mLB plates. A small amount of cells from a colony was picked from the plate with a pipette tip and was spotted on a MALDI plate. The sample was overlaid with 2 μL of a 9:1 mixture of 2,5-dihydroxybenzoic acid and 2-hydroxy-5-methoxybenzoic acid matrix prepared in 60% acetonitrile/0.1% TFA in water (80 mg/mL). A heat gun was used to dry the sample.

Figure 2:
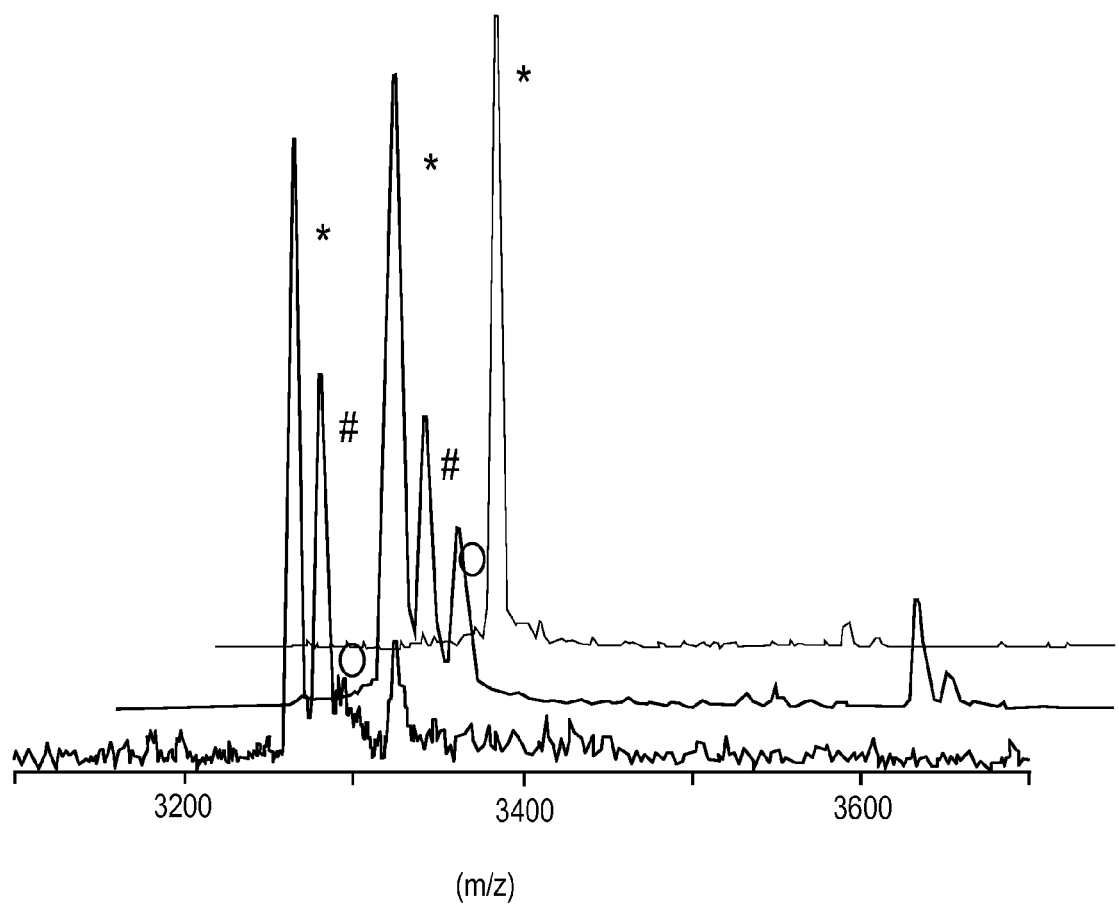
FIG. 2 shows geobacillin I production in native and heterologous producers. MALDI-MS spectra showing geobacillin I production by a native producer at the trace beginning at about 3100 m/z and by the heterologous *E. coli* host at the trace beginning at about 3150 m/z. Purified nine-fold dehydrated and cyclized core peptide is shown at the trace beginning at about 3220 m/z. Nine-fold, eight-fold, and seven-fold dehydrated peptides are denoted by *, #, and •, respectively.

Whole-cell matrix-assisted laser desorption ionization mass spectrometry (MALDI-MS) (22) was used to investigate the production of geobacillin I and geobacillin II after 12 h, 24 h and 48 h. MALDI-ToF MS was carried out on a Voyager-DE-STR (Applied Biosystems) or Bruker Ultrafex TOF/TOF. A mass corresponding to GeoAI after nine dehydrations and removal of the leader peptide at the predicted site was observed in both media for five of the strains after 24 h. Only *G. thermodenitrificans* NM16-2 and *G. kaustophilus* DSM7263 did not produce geobacillin I under the conditions used. A representative MALDI mass spectrum is shown in FIG. 2. All five organisms produced peptides of the same mass, consistent with the near-identical sequences of GeoAI observed in the currently sequenced genomes (FIG. 1C). All five observed peptides had masses consistent with a Val at position 15 rather than an Ile. These observations along with the genome data suggest very high conservation of the sequence of geobacillin I in the *Geobacillus* genus. The mass spectrum in FIG. 2 also shows peaks corresponding to eight-fold and seven-fold dehydrated peptide, reminiscent of incomplete dehydration of nisin in *Lactococcus lactis* 6F3 (23).

Whole-cell MALDI-MS analysis did not show production of geobacillin II by any of the seven *Geobacillus* strains. In silico analysis revealed the presence of its class II gene cluster only in *Geobacillus thermodenitrificans* NG80-2 and *Geobacillus* sp. G11MC16 and not in any other sequenced *Geobacillus* genome (18). Indeed, attempts to detect the geoM biosynthetic gene in the genomic DNA of the seven strains used in this study by PCR with various degenerate primers were unsuccessful. All polymerase chain reactions (PCR) were carried out on a C1000™ thermal cycler (Bio-Rad). *E. coli* DH5α was used as host for cloning and plasmid propagation, and *E. coli* BL21 (DE3) was used as a host for co-expression.

Example 3

Biosynthesis of Geobacillin I and Geobacillin II in *E. coli*

TABLE 1

Primer sequences used for plasmid constructs and mutagenesis experiments

| Primer name | Primer sequence |
|---|---|
| GeoAI_BamHI_F | CTA GAT GGA TCC GAT GGC CAA ATT TGA TGA TTT TGA TC (SEQ ID NO: 7) |
| GaoAI_HindIII_R | CTA GAA GCT TTT ATT AGC AAC GAA TAC AGC TAT TAC AGC (SEQ ID NO: 8) |
| GeoB_NdeI_F | ACA GCC GCA TAT GAA TGA TCT GGT GTT AAA AAT TG (SEQ ID NO: 9) |
| GeoB_XhoI_R | TCT AGC TCG AGTTAA TTT TTC AGC ACC AGG CCA TGG GC (SEQ ID NO: 10) |
| GeoC_NdeI_F | AAG CAG CCG CAT ATG TCT ATT AGC ATG AAA GCC CTG G (SEQ ID NO: 11) |
| GeoC_NdeI_R | CTA GCT CGA GTAAAA CTT CGC TCA G CA GAA ATG CAC AAT CC (SEQ ID NO: 12) |
| GeoAI (N-1K)_F | CAG GAT GAT GTT GTT CAG CCG AAA GTT ACC AGC AAA AGC CTG (SEQ ID NO: 13) |
| GeoAI (N-1K)_R | CGG CTG AAC AAC ATC ATC CTG TTT TTT CAC C (SEQ ID NO: 14) |
| GeoAII_BamHI_F | CTA GAT GGA TCC GAT GAA AGG TGG CAT TCA GAT GG (SEQ ID NO: 15) |
| GeoAII_HindIII_R | CTA GAA GCT TTT ACA TCG GAC AAC GAA CTT TAA AGC (SEQ ID NO: 16) |
| GeoM_NdeI_F | AAG CAG CCG CAT ATG AAC GAA ATC GTG GAA AAT AAC C (SEQ ID NO: 17) |
| GeoM_XhoI_R | CTA GCT CGA GTT AAT GGT TCA GCT GCA GAG TCA GCA CG (SEQ ID NO: 18) |

TABLE 1 -continued

Primer sequences used for plasmid constructs and mutagenesis experiments

| Primer name | Primer sequence |
|---|---|
| GeoAII (G-8K)_F | GAA AAA ACT GGC TGG CAA ATA TAC CGA AGT TTC TCC G (SEQ ID NO: 19) |
| GeoAII (G-8K)_R | GCC AGC CAG TTT TTT CAG TTC TTC TTC GC (SEQ ID NO: 20) |
| GeoAII (Q-1E)_F | GTT ATA CCG AAG TTT CTC CG GAAAGCA CCA TTG TTT GTG (SEQ ID NO: 21) |
| GeoAII (Q-1E)_R | CGG AGA AAC TTC GGT ATA TTT GCC AGC CAG (SEQ ID NO: 22) |
| GeoAII (Q-1K)_F | GTT ATA CCG AAG TTT CTC CGA AAA GCA CCA TTG TTT GTG (SEQ ID NO: 23) |
| GeoAII (Q-1K)_R | CGG AGA AAC TTC GGT ATA ACC GCC AGC CAG (SEQ ID NO: 24) |

Codon-optimized synthetic genes for GeoAI, GeoB, GeoC, GeoAII, and GeoM were synthesized by GeneArt (Invitrogen, USA). For geobacillin I production, geoAI was inserted in MCS1 of a pRSFDuet-1 vector using BamHI and HindiI restriction sites, geoB in MCS2 using NdeI and XhoI sites, and geoC in MCS2 of pACYCDuet-1 using NdeI and XhoI sites. This construct results in a hexa-histidine-tagged precursor peptide ($His_6$-GeoAI) and an untagged GeoB protein. A synthetic gene encoding the cyclase GeoC was inserted into MCS-2 of a pACYCDuet-1 vector, resulting in an untagged GeoC enzyme. Site-directed mutagenesis was performed to mutate Asn at the −1 position of the GeoAI peptide (FIG. 1D) to Lys to incorporate a trypsin cleavage site in the precursor peptide to be used for leader peptide removal. For primers see Table 1. E. coli BL21 (DE3) cells were transformed with both plasmids and after induction of protein expression, $His_6$-GeoAI was purified from the cell lysate using nickel affinity chromatography followed by reverse phase high performance liquid chromatography (RP-HPLC). (24) The modified precursor peptide was treated with trypsin and MALDI-MS analysis of the resultant peptide demonstrated a nine-fold dehydrated core peptide (FIG. 2). As seen with the native producers, peaks corresponding to eight and seven-fold dehydrated peptides were also observed.

Figure 5:
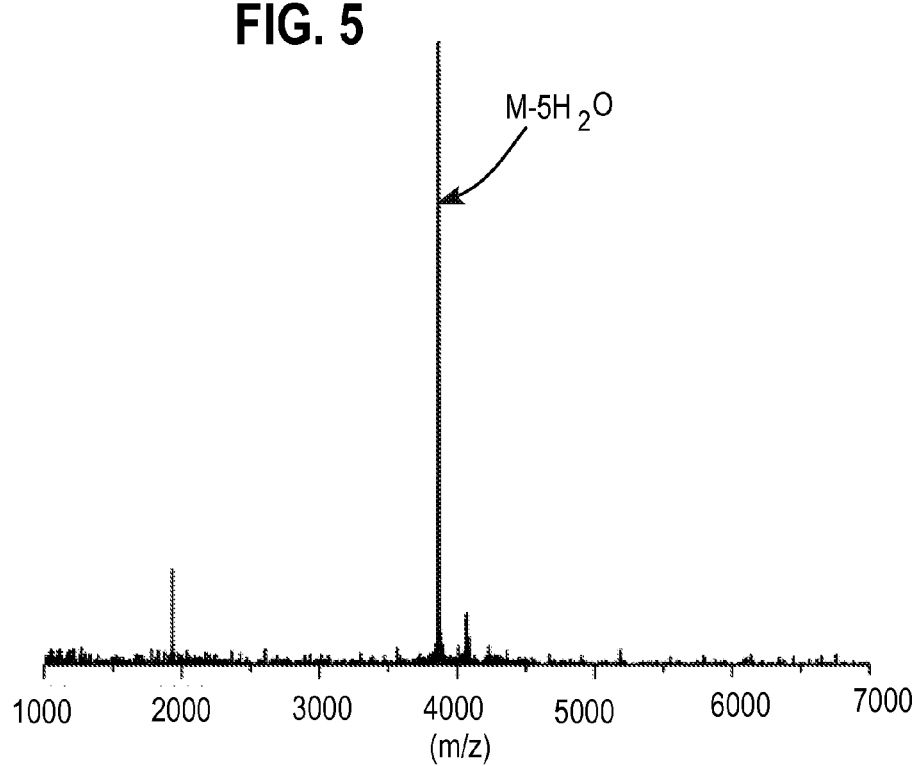
FIG. 5 shows MALDI-MS spectrum of GeoAII (G-8K/Q-1E) modified by GeoM in $E.$ $coli$ and treated with trypsin.
Figure 6:
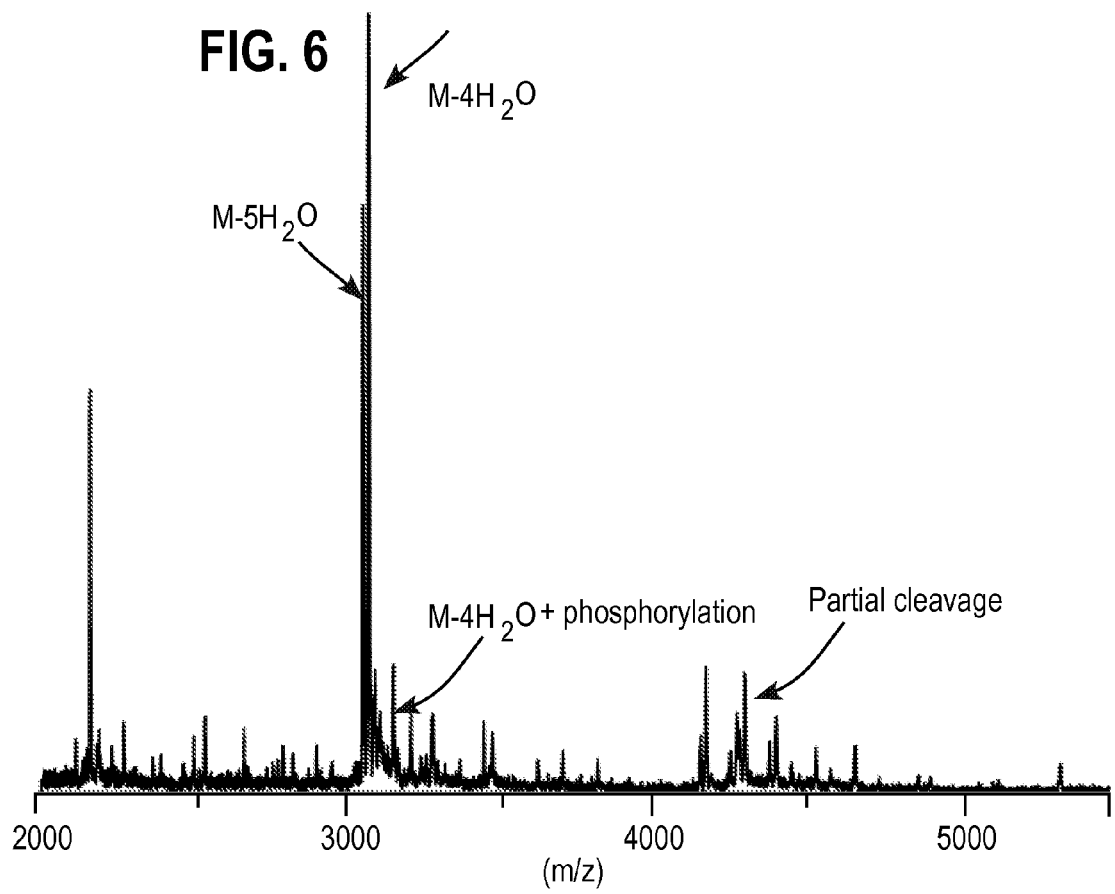
FIG. 6 shows MALDI-MS spectrum of GeoAII (Q-1K) modified by GeoM in $E.$ $coli$ and treated with trypsin.

A similar approach was taken to produce geobacillin II. Synthetic genes encoding GeoAII and GeoM were inserted into MCS-1 and MCS-2 of a pRSFDuet-1 vector, respectively. Site-directed mutagenesis was performed to mutate the second Gly in the double Gly motif of the GeoAII peptide to Lys to incorporate a trypsin cleavage site for leader peptide removal. Co-expression of GeoM with its substrate precursor peptide in E. coli at 37° C. and subsequent purification as described for geobacillin I resulted in five-fold dehydrated peptide after trypsin removal of the leader peptide (FIG. 5).

More specifically, single colony transformants containing plasmids pRSFDuet-1 (GeoAI/GeoB) and pACYCDuet-1 (GeoC) were picked and grown in LB media overnight. The culture was used to inoculate a 6 L culture in Terrific Broth media containing 50 mg/L kanamycin and 34 mg/L chloramphenicol. The culture was shaken at 200 rpm at 37° C. until the OD600 nm reached between 0.6 and 0.8. At this point, the culture was induced with 0.5 mM IPTG. The induced cells were shaken continually at 37° C. for an additional 3 h, and the cells were harvested by centrifugation (11,900×g for 10 min, Beckman JLA-10.500 rotor). The cell pellet was resuspended in 50 mL of start buffer (20 mM Tris, pH 8.0, 500 mM NaCl, 10% glycerol), and cell lysis was carried out using a MultiFlex C3 homogenizer (Avestin). The lysed cells were centrifuged at 23,700×g for 30 min at 4° C. The supernatant was loaded onto a HiTrap HP nickel affinity column (GE Healthcare) pre-equilibrated with start buffer. The column was washed with wash buffer (start buffer containing 30 mM imidazole), and the peptide was eluted from the column with elution buffer (start buffer containing 1 M imidazole). The pellet after the lysis step was homogenized using a sonicator (35% amplitude, 4.4 s pulse, 9.9 s pause for total 20 min) in start buffer to remove any soluble proteins. The suspension was centrifuged and the pellet was homogenized in 30 mL of denaturing buffer (4 M guanidine hydrochloride, 20 mM $NaH_2PO_4$, 500 mM NaCL, pH 7.5). The supernatant after centrifugation was loaded onto a HiTrap HP nickel affinity column, the column was washed with denaturing buffer containing 30 mM imidazole, and the product was eluted with 15 mL of denaturing buffer containing 1 M imidazole. Small aliquots of eluent were desalted using a ZipTip (µC18) and analyzed for the presence of geobacillin I using MALDI-MS. For large scale purification, the eluent was desalted using preparative scale RP-HPLC using a Waters Delta-pak C4 15 µm; 300 Å; 25×100 mm PrepPak Cartridge. A gradient of 2-100% of solvent B (0.086% TFA in 80% ACN/20% water) was used (Solvent A=0.086% TFA in 2% ACN/98% water). Modified GeoAI started eluting at 55% B. The fractions containing modified GeoAI were lyophilized. For geobacillin II production, GeoAII and GeoM were cloned in MCS1 and MCS2 of a pRSFDuet-1 vector, respectively. Site directed mutagenesis was performed to change the glycine at position −8 to lysine (pRSFDuet-1 GeoAII G-8K/GeoM). Two other constructs were made in which glutamine at position −1 was either mutated to lysine (pRSFDuet-1 GeoAII Q-1K/GeoM) or glutamate (pRSFDuet-1 GeoAII G-8K,Q-1E/GeoM). Expression and purification of these constructs was conducted as described for geobacillin I.

Example 4

Bioactivity of Geobacillin I and Geobacillin II

Figure 7:
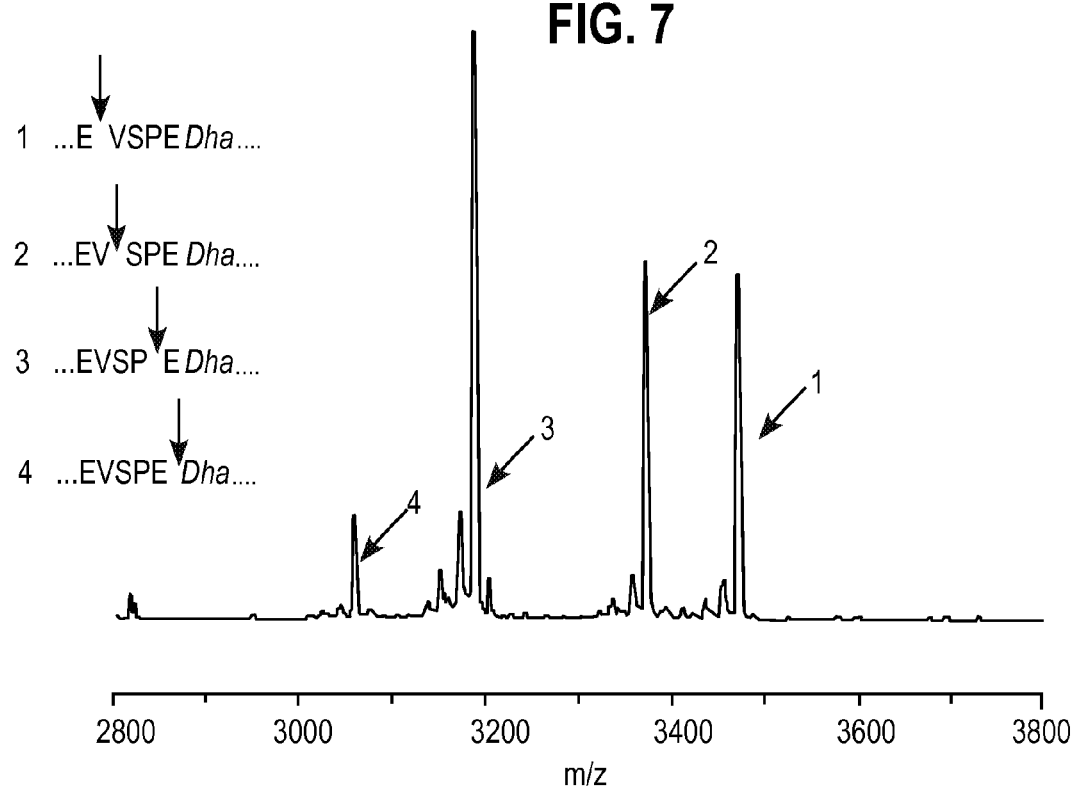
FIG. 7 shows MALDI-MS spectrum of GeoAII (Q-1E) modified by GeoM in $E.$ $coli$ and treated first with GluC and then aminopeptidase. Peptide 1 is initially formed upon GluC cleavage. The aminopeptidase then partially removed additional amino acids from the N-terminus as shown in the inset. The aminopeptidase treated sample gave the same size of the zone of growth inhibition as pure peptide 1 (see FIG. 3B) suggesting that further removal of the amino acids shown from the N-terminus does not result in more active peptides.

A solution of 500 µM posttranslationally modified GeoAI-N-1K in 50 mM HEPES buffer (pH 8.0) was treated with 0.5 µM trypsin for 2 h. The product was analyzed using MALDI-MS. The nine-fold dehydrated and cyclized core peptide was purified using RP-HPLC in order to remove incompletely dehydrated peptide and leader peptide using a Phenomenex Luna C18 column (250×10 mm, 10 micron) operating at a flow rate of 10 mL/min. The program used was 3 min of solvent A (2% MeCN/0.1% TFA) followed by a gradient of 2-100% solvent B (80% MeCN/0.1% TFA) over 50 min. For preparation of geobacillin II, GeoM-modified and HPLC-purified GeoAII-G-8K/Q-1E (100 µM) was treated with either 0.1 µM trypsin (20 min.) or 0.5 µM GluC (2 h). GeoAII- Q-1K (100 μM was also treated with 0.1 μM trypsin. The GluC-cleaved GeoAII-G-8K/Q-1E peptide (25 μL, 100 μM) was further treated with 8 μL Leu aminopeptidase for 24 h at 37° C. The resulting products were analyzed by MALDI-MS (FIG. 7) and the observed and calculated molecular weights are summarized in Table 2.

TABLE 2

Theoretical and observed molecular weights ([M + H]$^{1+}$) of modified peptides.

| Peptide | Protease used | Theoretical [M + H]$^{1+}$ | Observed [M + H]$^{1+}$ |
|---|---|---|---|
| Geobacillin I (from GeoA-N-1K) | Trypsin | 3265 | 3265 |
| Geobacillin II (from GeoA-G-8K/Q-1E) | GluC | 3470, 3057 | 3470, 3057 |
| Geobacillin II (from GeoA-G-8K/Q-1E) | GluC and aminopeptidase | 3470, 3371, 3187, 3057 | 3470, 3371, 3187, 3058 |
| Geobacillin II (from GeoA-G-8K/Q-1E) | Trypsin | 3863 | 3863 |
| Geobacillin II (from GeoA-Q-1K) | Trypsin | 3057, 3075 | 3057, 3075 |

The antimicrobial spectrum of geobacillin I and geobacillin II was investigated with a range of Gram positive bacteria. Geobacillin I was produced in *E. coli* as described above, treated with trypsin, purified by RP-HPLC (FIG. 2), and used for MIC determinations in liquid medium (31).

TABLE 3

Specific activity of geobacillin I and nisin in liquid growth inhibition assay

| Strain | Source | Geobacillin I IC$_{50}$ (μM) | Geobacillin I IC$_{90}$ (μM) | Nisin IC$_{50}$ (μM) | Nisin IC$_{90}$ (μM) |
|---|---|---|---|---|---|
| *Streptococcus dysgalatiae* subsp *dysgalactiae* | ATCC[a] 27957 | 0.69 ± 0.05 | 0.87 | 2.12 ± 0.04 | 3.87 |
| Vancomycin resistant *Enterococcus faecium* | CNRZ[b] 481 | 0.84 ± 0.05 | 1.1 | 0.39 ± 0.03 | 0.57 |
| Methicillin resistant *Staphylococcus aureus* | C5[c] | 2.23 ± 0.03 | 3.39 | 0.42 ± 0.01 | 0.77 |
| *Bacillus anthracis* Sterne 7702 | Gut et al.[d] | 0.49 ± 0.02 | 0.071 | 0.21 ± 0.014 | 0.52 |
| *Bacillus subtilis* | ATCC 6633 | 0.55 ± 0.01 | 0.81 | 0.11 ± 0.01 | 0.16 |
| *Lactococuus lactis* HP | ATCC 11602 | 0.12 ± 0.09 | 0.13 | 0.017 ± 0.005 | 0.019 |

[a] ATCC: American type Culture Collection.
[b] CNRZ: National Centre for Zootechnical Research.
[c] Clinical isolate from Carle Foundation Hospital (Urbana, IL).
[d] Reference (48).

For MIC calculations, a 48-well plate (300 μL well size) was used with shaking and a 96-well plate (200 μL well size) was used for non-shaking conditions, depending on the indicator strain. Serial dilutions of nisin and geobacillin I were prepared in sterile deionized water (SDW). The 48/96 plate wells contained 50/75 μL of diluted peptide at defined concentrations and 150/225 μL of a 1:10 dilution (approximately 1×10$^8$ CFU mL$^{-1}$) of a culture of indicator strain diluted in fresh growth medium. Growth medium blank and negative controls lacking the lantibiotics were also prepared. Plates were incubated under appropriate growth conditions (Table 4), and MIC calculations were performed by monitoring the OD$_{600}$. For agar diffusion bioactivity assays, the appropriate agar media (Table 4) was melted in a microwave, kept at 45° C. for 10 min, and mixed with 150 μL of overnight culture of indicator organisms (10$^8$-10$^9$ cfu). Then, 10 μL of a solution of 100 μM peptide was spotted on the plate. For trypsin cleaved GeoAII Q-1K, 10 μL of 300 μM peptide was spotted.

TABLE 4

Growth conditions for indicator strains.

| Strain | Media | Conditions |
|---|---|---|
| *Streptococcus dysgalatiae* subsp *dysgalactiae* | BHI | 37° C., aerobic |
| Vancomycin resistant *Enterococcus faecium* | BHI | 37° C., aerobic |
| Methicillin resistant *Staphylococcus aureus* | BHI | 37° C., aerobic |
| *Bacillus anthracis* Sterne 7702 | BHI | 37° C., aerobic |
| *Staphylococcus epidermidis* 15X | BHI | 37° C., aerobic |
| *Staphylococcus epidermidis* | BHI | 37° C., aerobic |
| *Bacillus cereus* Z4222 | LB | 30° C., aerobic |
| *Bacillus subtilis* | LB | 30° C., aerobic |
| *Lactococuus lactis* HP | GM17 | 30° C., anaerobic |
| *E. coli* DH5α | LB | 37° C., aerobic |
| *Micrococcus luteus* | LB | 37° C., aerobic |

The compound was active against a wide range of Gram positive bacteria but it was not active against Gram negative *E. coli*. Interestingly, in parallel experiments, geobacillin I demonstrated three-fold higher activity against *Streptococcus dysgalactiae* ATCC 27957 than nisin. This bacterium is one of the causative agents of bovine mastitis (16). Geobacillin I displayed similar activity as nisin against VRE and *Bacillus anthracis* Sterne 7702, and had five-fold lower activity against MRSA and *Bacillus subtilis* ATCC 6633. Its antimicrobial activity against *Lactococcus lactis* HP is about seven-fold lower than nisin. As anticipated given the larger number of conformation-restraining crosslinks and the thermophilic producing strain, geobacillin I was more stable than nisin at pH 7 and 8.5 at 37° C. and at 60° C. See FIGS. 14-18.

Figure 3A:
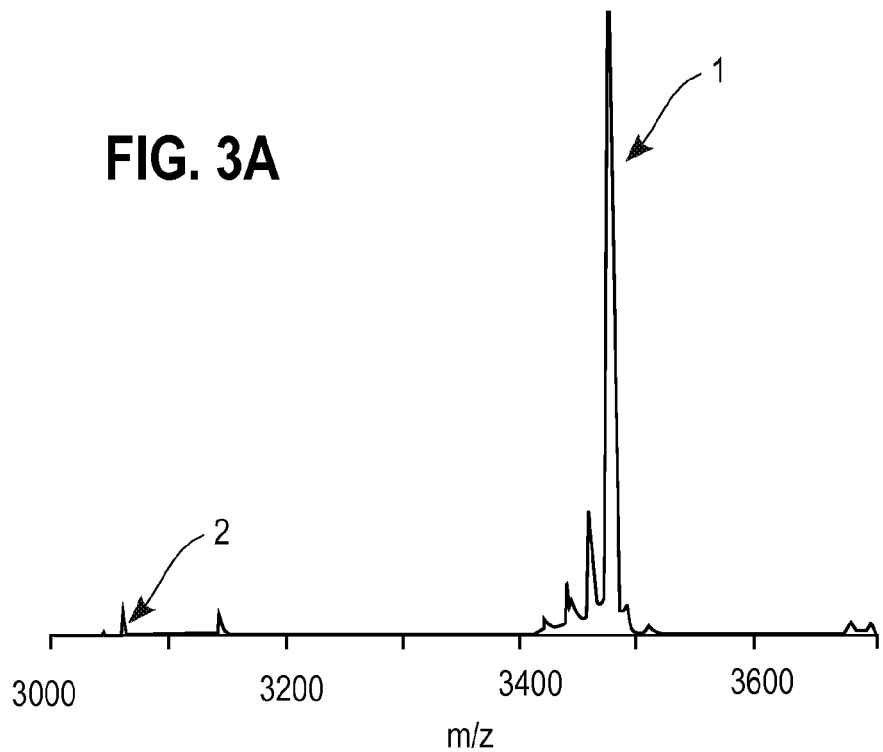
FIG. 3A-D show biosynthesis of geobacillin II and growth inhibition assays. A) MALDI-MS spectrum of GeoAII-Gln-1Glu modified by GeoM in *E. coli* and treated with GluC. Peptide 1 arises from cleavage at Glu-5, whereas peptide 2 arises from cleavage at Glu-1. B) Agar well diffusion assay with *B. subtilis* ATCC 6633. Zone 1: 10 μL of 100 μM GeoAII-Q-1E modified by GeoM and treated with GluC. This results predominantly in peptide 1 (see panel A). Zones 2 and 3: the material used for zone 1 was treated with aminopeptidase for 24 and 48 h, respectively. For MS data, see FIG. 7. Zone 4: 10 μL of 300 μM GeoAII-Q-1K modified by GeoM and treated with trypsin. This sample contains a mixture of four- and five-fold dehydrated peptide (see text and FIG. 6). Spot 5: trypsin-cleaved GeoAII-G-8K. Spot 6: negative control containing GluC and aminopeptidase. C) Observed fragmentation pattern in ESI tandem mass spectra of GeoAII modified by GeoM and treated with GluC. The b5 and y"26 ions appear to indicate that the A-ring is formed from Cys 5 and Dhb2, but two observations argue against this interpretation. First, if the ring were formed between Cys5 and Dhb2, the N-terminal Dha1 would hydrolyze to a lactate group (47), decreasing the mass by 1 Da; the masses in FIGS. 6 and 7 do not support this. Second, as shown in FIG. 1E, A-rings formed from Cys5 and a dehydro amino acid at position 1 are well conserved amongst various (antibiotics, and third, acid hydrolysis followed by derivatization and amino acid analysis by GC-MS only showed lanthionines for geobacillin AII (see FIG. 19). Thus, we attribute the b5 and y"26 ions to fragmentation in the A-ring. Similar fragmentation is also observed in the A-ring of nisin (see Fig S7 of reference (24). D) Ring topology of geobacillin II derived from the tandem MS results. Magenta arrows indicate the position and direction of (methyl)lanthionine formation.
Figure 3B:
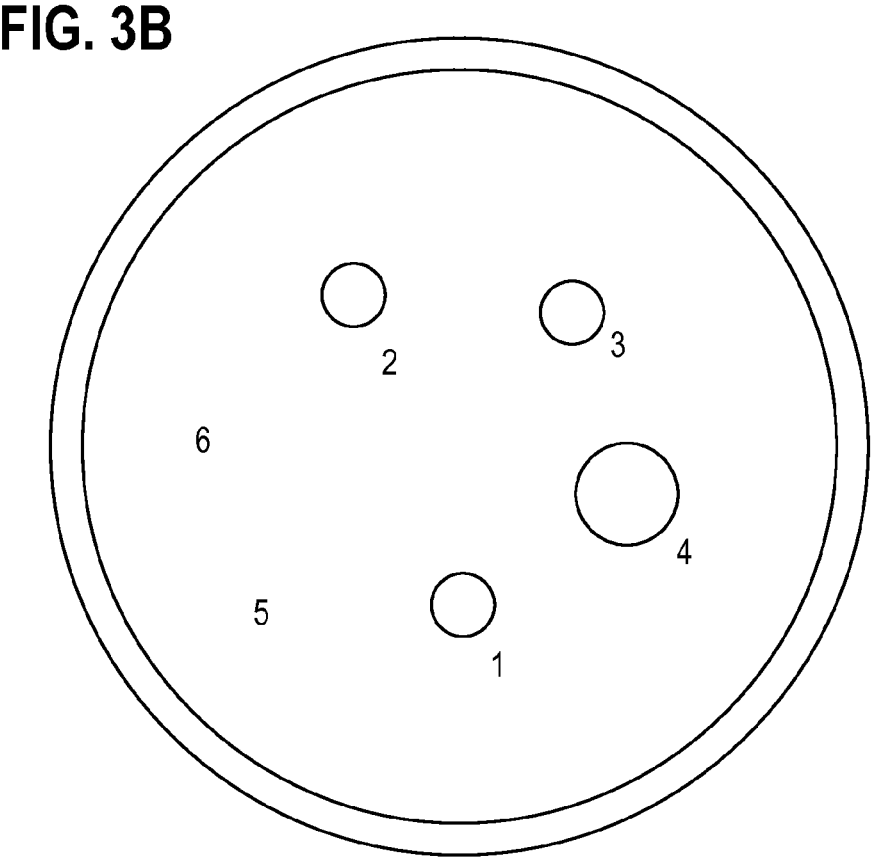

To determine the bioactivity of geobacillin II, purified five-fold dehydrated GeoAII in which the second Gly of the double-glycine motif was mutated to Lys was treated with trypsin and checked for bioactivity. No antimicrobial activity was observed against any of the strains in Table 3. Although it is not unprecedented that lanthionine-containing peptides do not demonstrate any antimicrobial activity (25-28), we wondered whether perhaps a second proteolytic cleavage event might be required. Removal of six additional N-terminal residues after leader peptide cleavage at a double glycine site has been reported previously for several class II lantibiotics (29-32). In some examples, such as cytolysin from *Enterococcus faecalis*, removal of these additional residues from the N-terminus of the modified core peptide is necessary for bioactivity (30), but in other examples (e.g., haloduracin (33)) such removal is not required. A sequence alignment of the predicted core peptide of GeoAII with the core peptides of lantibiotics that are currently known to undergo a second proteolytic step is shown in FIG. 1E. The N-terminal amino acids of GeoAII display only low level sequence homology with the sequences that are removed in the other peptides, but the presence of a Pro-Gln sequence and the observation that the GeoAI leader peptide is removed at a Pro-Asn site prompted us to investigate whether removal of additional amino acids might result in bioactivity. First, a trypsin cleavage site was introduced into wild type GeoAII by mutation of Gln-1 to Lys (this numbering assumes cleavage after ProGln, FIG. 1E). Unfortunately, this mutant was not processed well in *E. coli* (predominantly 4 dehydrations), presumably because introduction of a positively charged residue is detrimental for GeoM activity. A different mutant was constructed next (GeoAII-Gln-1Glu) and co-expressed with GeoM in *E. coli* resulting in the desired five-fold dehydrated peptide. Proteolysis with endoproteinase GluC did not result in efficient cleavage after the introduced Glu-1 (FIG. 3A), presumably because the posttranslationally modified Ser at position 1 deactivates the engineered cleavage site. Instead GluC cleaved predominantly after Glu-5 (FIG. 3A) resulting in the removal of only two residues (Tyr and Thr) at the N-terminus compared to cleavage at the double Gly site. Interestingly, this GluC-treated core peptide induced zones of growth inhibition for *Bacillus* strains in agar well diffusion assays (FIG. 3B). Thus, removal of Tyr or Thr (or both) may be required for bioactivity. Geobacillin II only showed bioactivity against *Bacillus* species and no activity against any other tested bacteria (Table 5). Attempts to increase the observed bioactivity by treatment with aminopeptidase (34) to remove additional amino acids (for MS data see FIG. 7) did not result in increased zones of growth inhibition (compare spots 1 and 2, FIG. 3B).

TABLE 5

Bioactivity spectrum of geobacillin II assessed by zones of growth inhibition in agar well diffusion assays.

| Strain | Source | Geobacillin II |
|---|---|---|
| Micrococcus luteus | ATCC 4698 | − |
| Streptococcus dysgalatiae subsp dysgalactiae | ATCC 27957 | − |
| Staphylococcus epidermidis 15X | Ekkelenkamp et. al.[a] | − |
| Staphylococcus epidermidis | ATCC12228 | − |
| Bacillus cereus Z4222 | INRA[b] Z4222 | + |
| Bacillus subtilis | ATCC 6633 | + |
| Lactococuus lactis HP | ATCC 11602 | − |
| E. coli DH5α | UIUC-CMF[c] | − |

[a]Reference (51).
[b]INRA: Institut National de la Recherche Agronomique.
[c]UIUC-CMF: University of Illinois Urbana-Champaign Cell and Media Facility.

Because authentic geobacillin II is not produced by the seven *Geobacillus* strains we evaluated, at present it is not clear where the core peptide of geobacillin II starts. We favor removal of the entire heptapeptide sequence YTEVSPQ (SEQ ID NO:66) after initial removal of the leader peptide at the double Gly site for the following reasons. Firstly, removal of this peptide would result from cleavage after Gln similar to the cleavage site for haloduracin from *Bacillus halodurans* and similar to lantibiotic proteases such as NisP involved in nisin biosynthesis (35). A LanP-type protease is not present in the gene cluster or elsewhere in the genome and therefore, like for haloduracin, the identity of the protease is not known, but the same protease may remove the leader of GeoAI at its Pro-Asn cleavage site. Secondly, cleavage after the ProGln sequence would result in an N-terminal structure very similar to that of haloduracin β, plantaricin β, and cytolysin CyIL$_S$ (FIG. 1E; FIG. 4D).

However, possible alternative geobacillin II structures are shown in FIG. 13A-B. The structures differ depending on where the proteolysis occurs on the N-terminus and whether ring A is formed by cyclization of Cys onto Dha (FIG. 13B) or Dhb (FIG. 13A).

Example 5

Chemical Stability of Nisin A and Geobacillin I

Stock solutions of nisin A and geobacillin I (30 μM) were prepared in 50 mM sodium phosphate buffer, 100 mM NaCl at pH 7.0 and 8.0. The stock solutions were divided into 200 μL aliquots in sterile eppendorf tubes and were incubated at 37° C. and 60° C. At set time points, a tube was opened and analyzed by agar diffusion growth inhibition assay (FIGS. 14-17). The agar diffusion growth inhibition assay was carried out in sterile Nunc OmniTrays. Molten agar (20 mL) was inoculated with 200 μL of overnight culture of *Bacillus subtilis* ATCC 6633 diluted to OD$_{600}$ of 1.0. An additional 30 mL molten agar combined with 300 μL cells was poured over the solidified agar. A sterile 96 well PCR plate was carefully placed on the upper molten agar layer. Following solidification, the PCR plate was removed and 20 μL of peptide solution was added to the wells. After 20 min, another 20 μL of peptide solution was added. This procedure was repeated one more time to add a combined total volume of 60 μL. The samples at 37° C. were also analyzed by HPLC but for a shorter time period. At later time points, the amount of remaining intact peptides was difficult to determine because of closely eluting breakdown products. The main breakdown product of geobacillin I appeared to be an oxidation product (M+16) but this did not appear to significantly affect the antimicrobial activity.

Agar diffusion growth inhibition assays were conducted with *B. subtilis* 6633 to determine the relative stabilities of geobacillin I and nisin A at pH 7.0 (FIG. 14) or pH 8.0 (FIG. 15) and 60° C. Aliquots of 60 µL of 30 µM solutions of compound that had been incubated for the time shown (in hours) were added to each well. The diameters of the zones of growth inhibition show that geobacillin I displays greater stability than nisin A.

Agar diffusion growth inhibition assays were also conducted with *B. subtilis* 6633 to determine the relative stabilities of geobacillin I and nisin A at pH 7.0 (FIG. 16) and pH 8.0 (FIG. 17) at 37° C. Aliquots of 60 µL of 30 µM solutions of compound that had been incubated for the time shown (in days) were added to each well. The diameters of the zones of growth inhibition show that geobacillin I displays greater stability. Nisin standards (60 µL per well) are shown on the left.

Figure 22A:
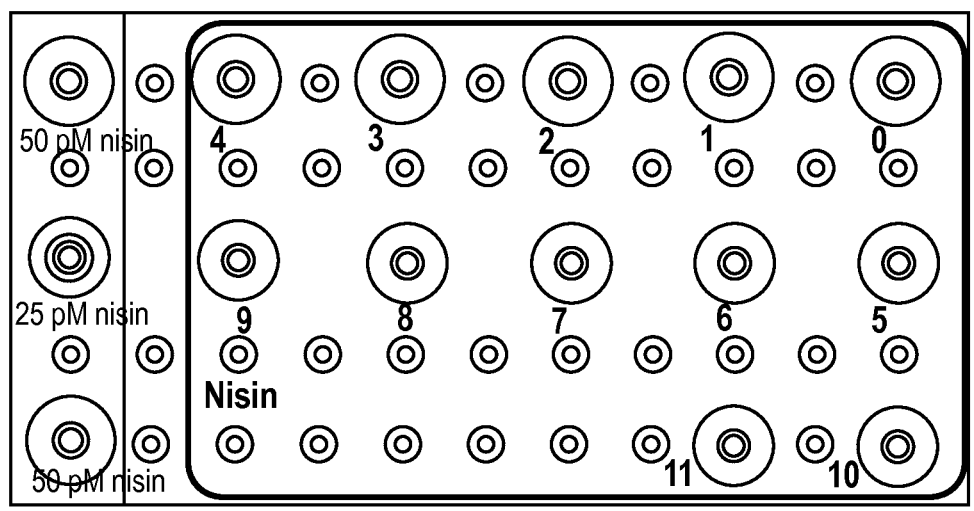
FIG. 22A-C show an agar diffusion growth inhibition assay with $B.$ $subtilis$ 6633 to determine the relative stabilities of nisin A (A) wild-type geobacillin I (B), geobacillin I mutant KFI (C) and nisin A at pH 7.0 and 37° C.
Figure 22B:
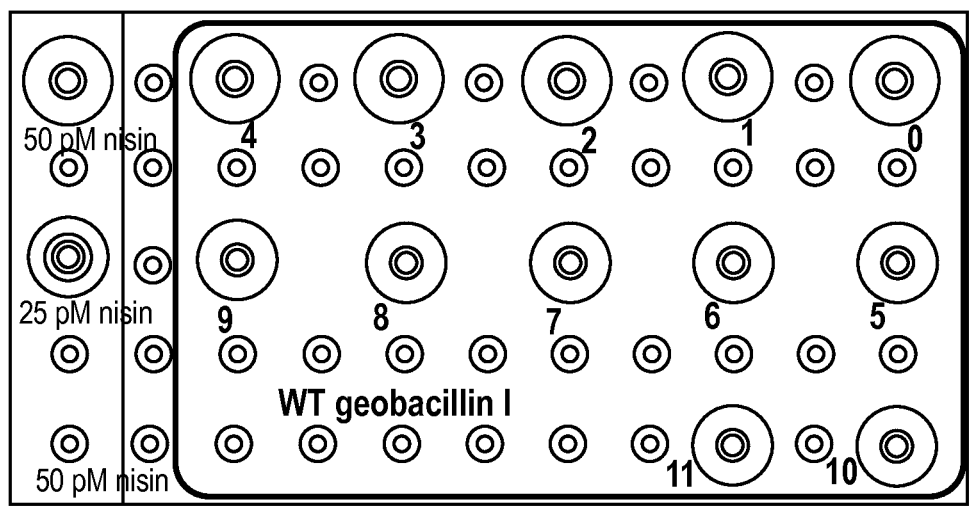
Figure 22C:
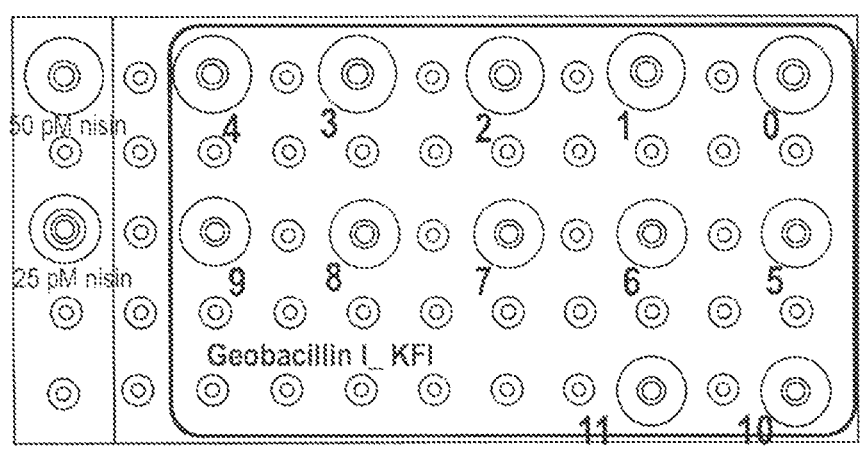

Agar diffusion growth inhibitions assays were conducted with MOPS buffer. Stock solutions of nisin A and geobacillin I (50 µM) were prepared in MOPS buffer (50 mM 3-(N-morpholino)propanesulfonic acid), 100 mM NaCl at pH 7.0. The stock solutions were divided into 200-µL aliquots in sterile eppendorf tubes and were incubated at 37° C. At set time points, a tube was opened and analyzed by agar diffusion growth inhibition assay. The agar diffusion growth inhibition assay was carried out in sterile Nunc OmniTrays. Molten agar (20 mL) was inoculated with 200 µL of overnight culture of *Bacillus subtilis* ATCC 6633 diluted to OD600 of 1.0. An additional 30 mL molten agar combined with 300 µL cells was poured over the solidified agar. A sterile 96-well PCR plate was carefully placed on the upper molten agar layer. Following solidification, the PCR plate was removed and 20 µL of peptide solution was added to the wells. After 20 min, another 20 µL of peptide solution was added. This procedure was repeated one more time with 10 µL to add a combined total volume of 50 µL. The resulting zones of growth inhibition are shown in FIG. 22 A-C. It can be seen that the zones of inhibition decrease over time for nisin but not for geobacillin I, illustrating higher stability of the latter.

Figure 18A:
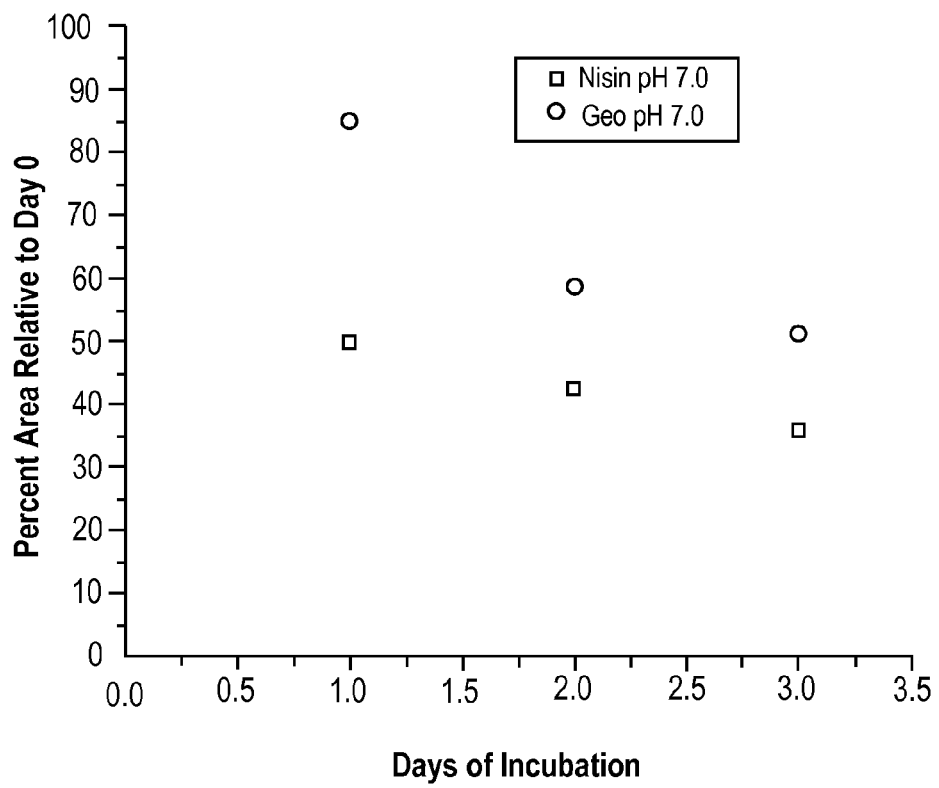
FIG. 18A-B show an assessment of the relative stabilities of nisin A and geobacillin I using HPLC analysis.
Figure 18B:
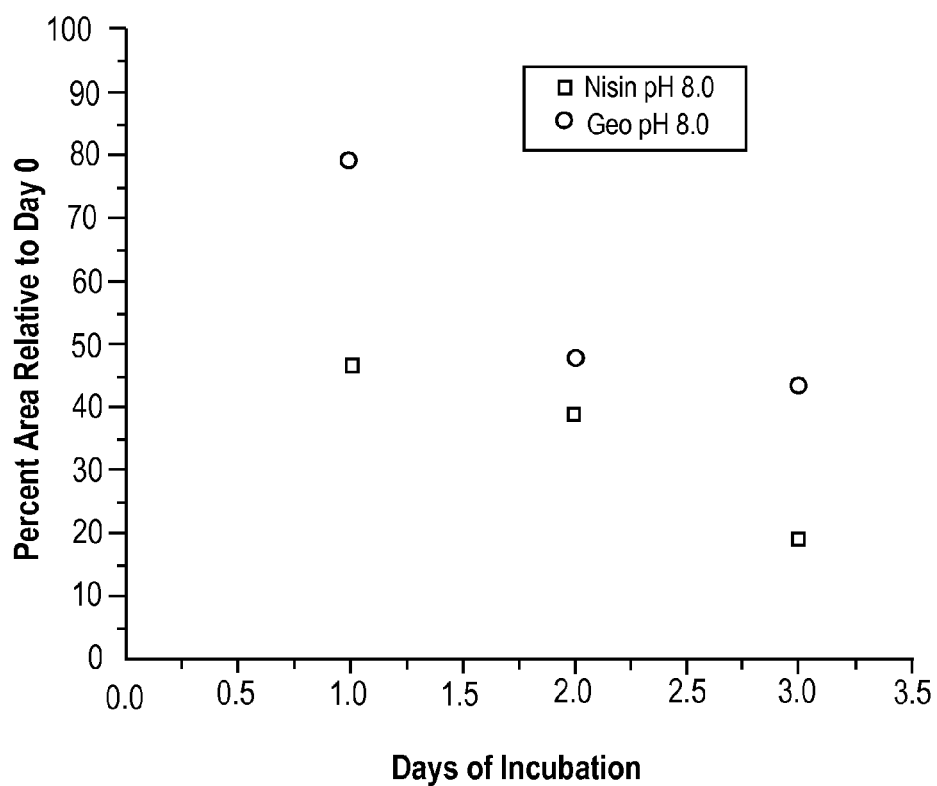

FIG. 18A-B shows an assessment of the relative stabilities of nisin A and geobacillin I using HPLC analysis.

Example 6

Structure Determination of Geobacillin I and Geobacillin II

Tandem mass spectrometric analysis has been previously used to determine the ring topology of lanthionine-containing peptides that do not contain overlapping rings (32, 36), and for some of these peptides, the topology determined by tandem MS studies has been confirmed by NMR spectroscopy (37, 38). In this work, tandem MS was used to determine the ring pattern of geobacillin II because the amounts of material generated were insufficient for NMR studies. Liquid chromatography electrospray ionization tandem mass spectrometry was carried out and processed using a Synapt ESI quadrupole ToF Mass Spectrometry System (Waters) equipped with an Acquity Ultra Performance Liquid Chromatography (UPLC) system (Waters).

Figure 3C:
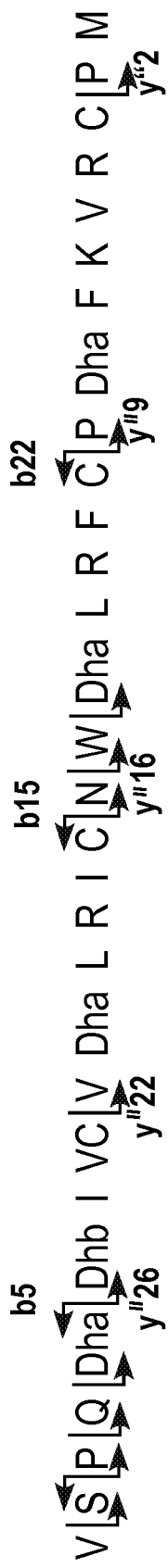
Figure 3D:
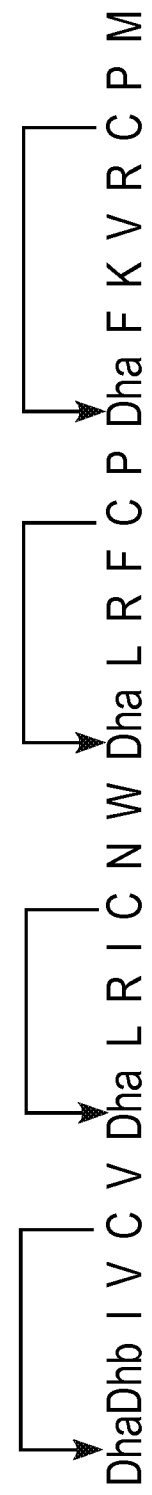
Figure 8:
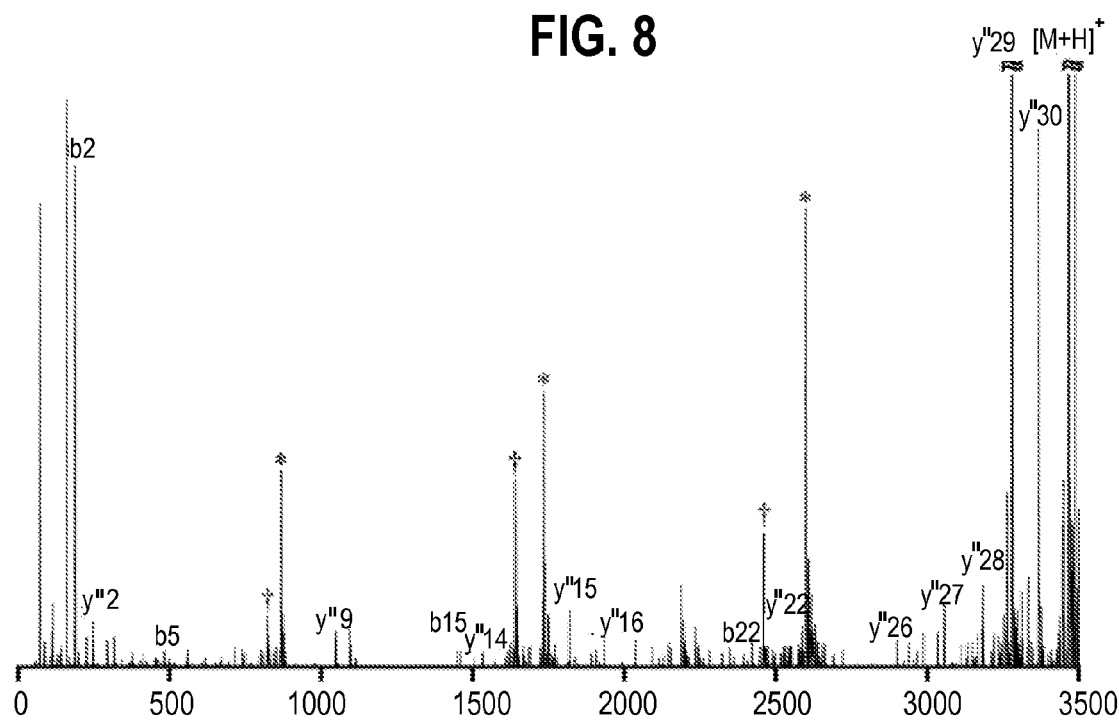
FIG. 8 shows tandem MS spectrum of GeoAII modified by GeoM in $E.$ $coli$ and treated with GluC. The b and y" ions are marked. Ions marked with asterisks and crosses are not fragment ions but arise from multiply charged ions.

The precursor peptide GeoAII was co-expressed with GeoM in *E. coli*, purified by IMAC chromatography, and treated with GluC to remove the leader peptide. The resulting five-fold dehydrated peptide was fragmented by collision induced dissociation resulting in the fragment ions indicated in FIG. 3C (see also FIG. 8). The observed ions are inconsistent with overlapping rings and agree very well with four non-overlapping rings. Based on these data, and the discussion in the previous section on the likely N-terminal amino acid, the structure shown in FIG. 3D is proposed for geobacillin II.

Figure 4A:
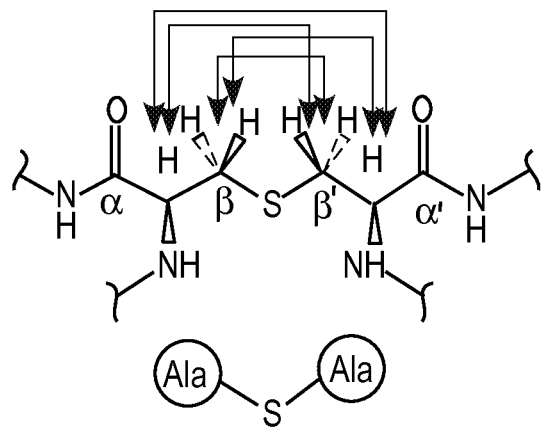
Figure 4A:
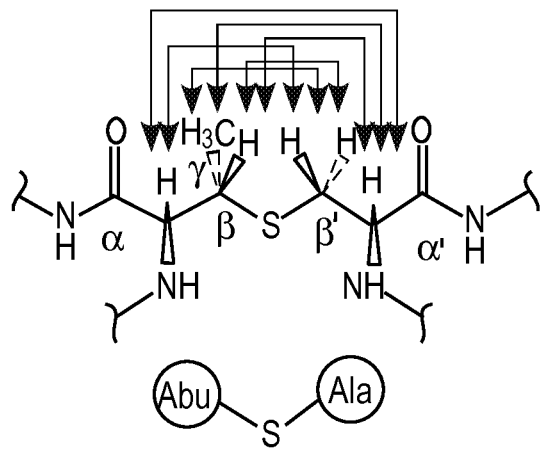
Figure 4B:
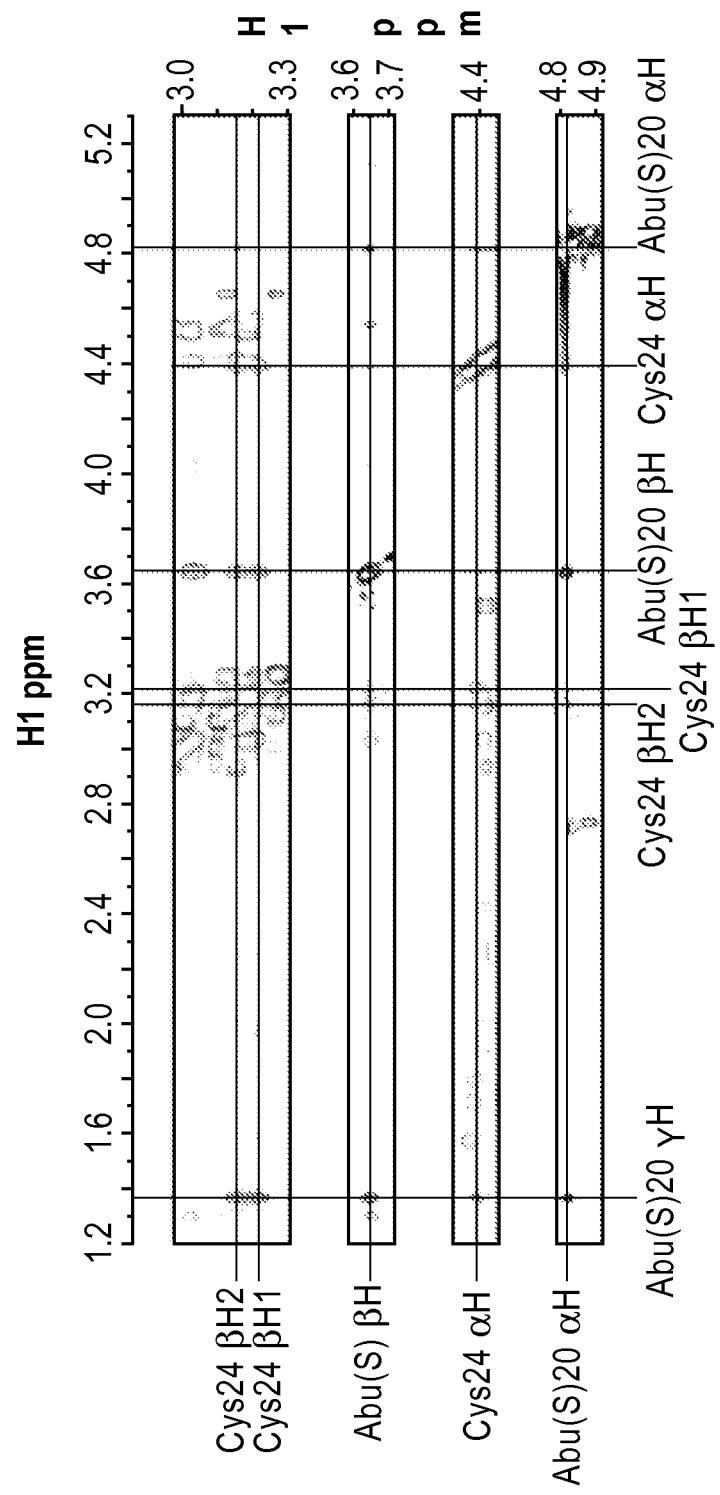
Figure 9:
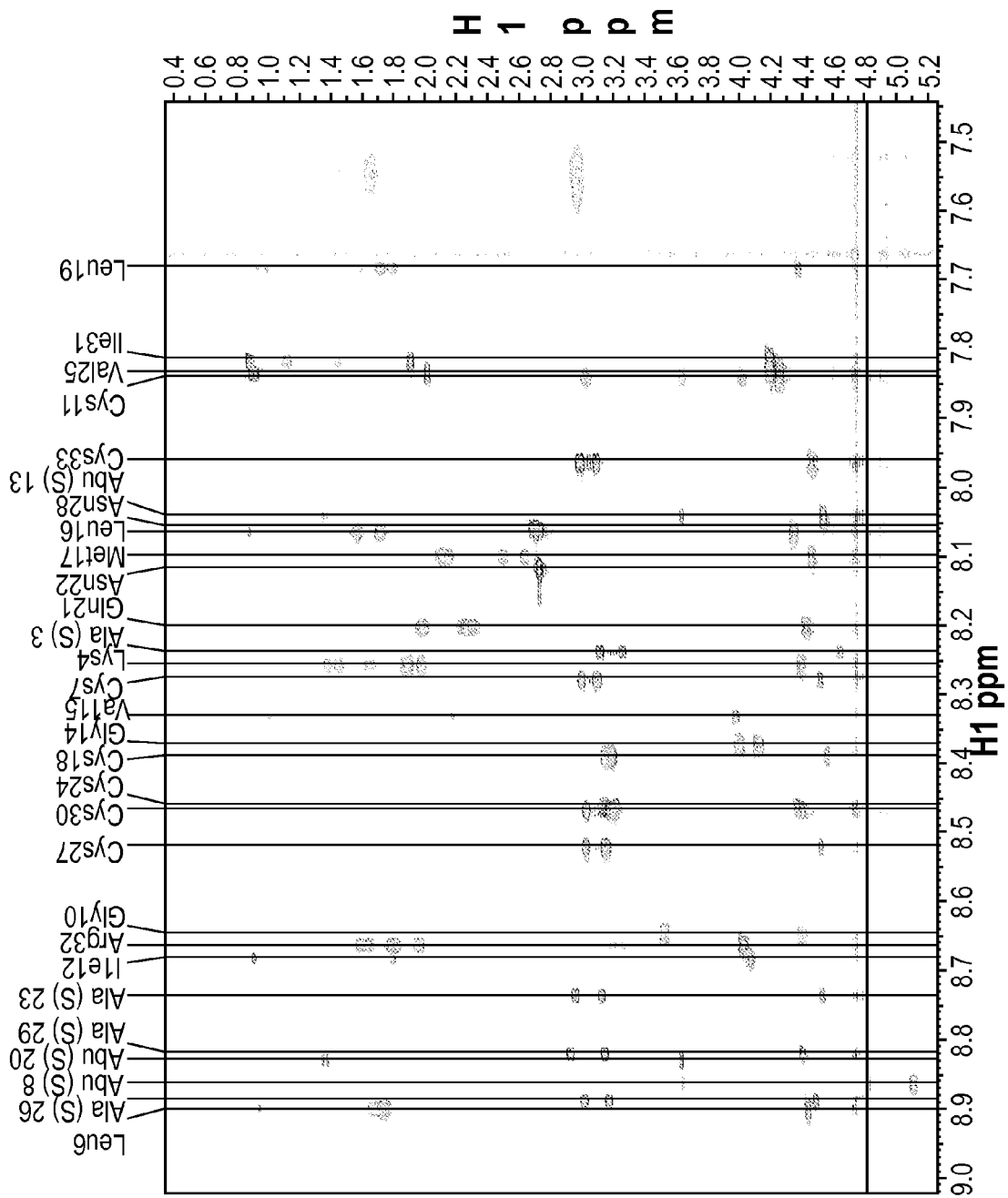
FIG. 9 shows water suppressed TOCSY spectrum identifying amino acid residues of geobacillin I. Each vertical line indicates a spin system corresponding to an amino acid. The amide protons of Dhb2 and Dha5 were not observed in this spectrum.
Figure 10:
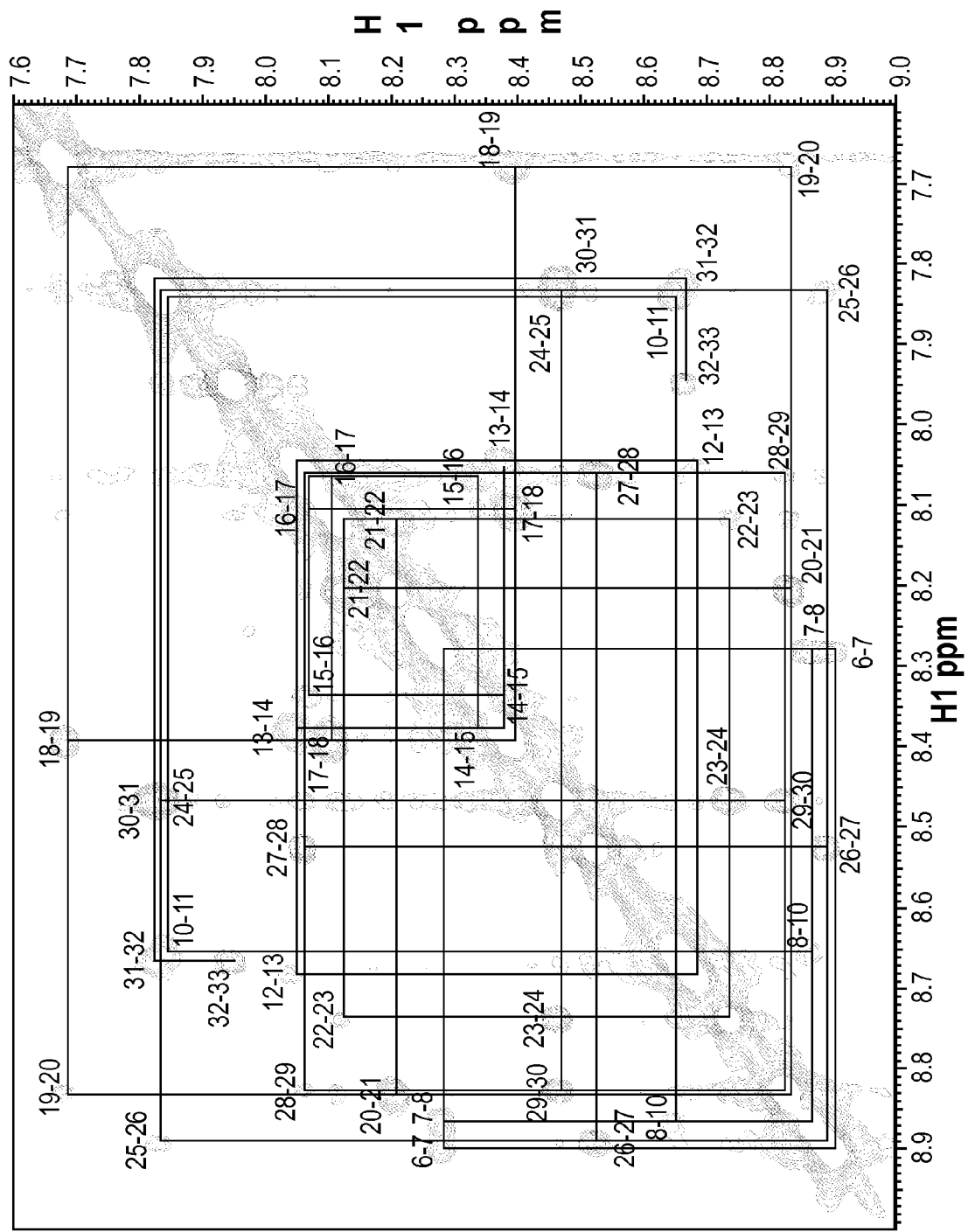
FIG. 10 shows water suppressed NOESY spectrum (mixing time=0.15 s) used for assignment of the amide resonances to specific amino acids in geobacillin I. In turn this information was used to assign the spin systems in FIG. 9 to specific amino acids.
Figure 11A:
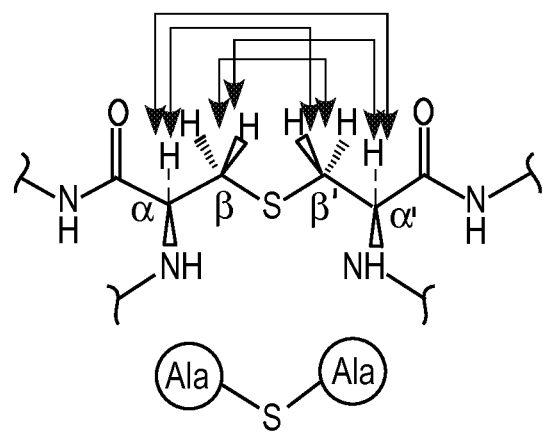
Figure 11B:
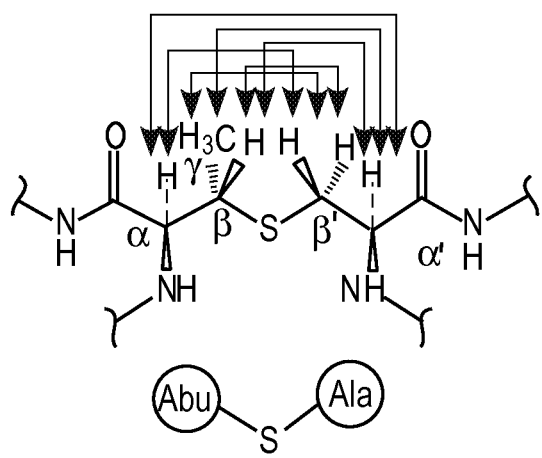

It was not possible to use tandem MS to determine the structure of geobacillin I because of overlapping rings. Therefore extensive NMR characterization was carried out on the compound produced in *E. coli*. First, nearly all resonances were assigned by TOCSY (FIG. 9) and gradient Double-Quantum-filtered COSY experiments. The assignments were further verified by determining the connectivities of $d_{NN(i,i+1)}$ (FIG. 10) as well as $d_{\alpha N-(i,i+1)}$ from a water-suppressed NOESY spectrum (mixing time=0.15 s) and taking into consideration the known linear amino acid sequence. Finally, a NOESY spectrum was acquired in $D_2O$ to determine intra-bridge NOEs, which facilitated the assignment of thioether links. A longer mixing time of 0.40 s was employed in this experiment to obtain stronger NOE signals. The observed cross peaks arising from correlations of $^1H^\alpha$—$^1H^{\alpha'}$, $^1H^\alpha$—$^1H^{\beta'}$, $^1H^\beta$—$^1H^{\beta'}$, $^1H^\beta$—$^1H^{\alpha'}$ and $^1H^\gamma$—$^1H^{\beta'}$. (' indicates proton across the thioether bridge, FIGS. 4A and 11) were used primarily to identify the ring patterns of six of the seven Lan and MeLan residues. The final Lan ring involving Cys30 and Dha26 could not be assigned based on the NMR data because of identical chemical shifts of the β-protons, but given that all other rings were assigned, one possibility exists for this last ring (the F ring). The final structure determined by NMR spectroscopy is shown in FIG. 4C.

NMR spectra were acquired at the NMR Facility (School of Chemical Sciences, University of Illinois at Urbana-Champaign) on a Varian INOVA 600 MHz spectrometer equipped with a 5 mm triple resonance ($^1H$—$^{13}C$—$^{15}N$) triaxial gradient probe. Lyophilized peptides were dissolved in 90% $H_2O$/10% $D_2O$ to a final concentration of 3 mM. 3-(Trimethylsilyl)propionic acid-$d_4$ sodium salt (DSS) was added to a final concentration of 1 mM to reference the spectrum. NMR spectra were acquired at 20° C. for 1028 detected and 400/512 indirect data points with 32 scans. TOCSY (mixing time 0.080 s), gDQCOSY and NOESY spectra were acquired with solvent suppression by transmitter presaturation. NOESY spectra with different mixing times of 0.15 s, 0.20, and 0.40 s were recorded. The peptides were lyophilized and redissolved in 100% $D_2O$ and a NOESY spectrum was acquired without exchangeable proton signals in order to assign the ring patterns. Spectra were processed with NMRPipe (49) and analyzed in Sparky (50). Resonances were first assigned to amino acids in order to determine the ring topology. The amino acid assignments were obtained primarily by TOCSY (shown in FIG. 8) and gDQCOSY. The chemical shifts of amide protons of geobacillin I in 90% $H_2O$ and 10% $D_2O$ were between 7 and 10 ppm, most of which showed good chemical shift dispersion in the TOCSY spectrum. Each vertical line in the TOCSY spectrum corresponds to one residue, which was assigned to an amino acid by taking into account their characteristic chemical shifts and expected number of resonances. The amide protons of Dhb2 and Dha5 not involved in the thioether rings were not detected under the conditions used. Assignments of each spin system to specific amino acids in the peptide sequence were based on the connectivity of $d_{NN(i,i+1)}$ (shown in FIG. 10) in a water suppressed NOESY spectrum (mixing time=0.15 s), taking into consideration the linear amino acid sequence translated from the gene sequence.

A NOESY spectrum was acquired in $D_2O$ in order to obtain clear intra-bridge NOEs by removing all correlations arising from the amide protons, which facilitated the assignment of thioether linkages. A longer mixing time of 0.40 s was employed to obtain stronger NOE signals. Cross peaks arising from $^1H^{\alpha'}$—$^1H^\beta$, $^1H^{\alpha'}$—$^1H^\alpha$, $^1H^{\beta'}$—$^1H^\beta$, $^1H^{\alpha'}$—$^1H^\gamma$ and $^1H^{\beta'}$—$^1H^{\gamma'}$ intrabridge correlations of protons that originated from either Ser/Thr or from Cys residues (indicated with ', see FIG. 11A-B) were used primarily to identify the ring patterns of Lan and MeLan residues. The 33 residue geobacillin I had seven methyl-lanthionine rings making the assignment quite challenging. The methyllanthionine rings B, C and D were easier to assign than lanthionine rings because of the relatively larger chemical shifts of their β protons (often higher than 3.5) and the presence of γ methyl protons in the high field region, for which signal overlap of the $^1H^\beta$—$^1H^\gamma$ and $^1H^\alpha$—$^1H^{\gamma'}$ correlations was less prominent. The lanthionine rings 1, 5 and 7 were assigned based on the $^1H^\alpha$—$^1H^\beta$ and $^1H^\beta$—$^1H^\beta$ cross peaks arising from NOEs of protons on opposites sides of the thioether bridge. Because the signal overlap in the 3.0-3.2 ppm region was significant, not all assignments of the $^1H^\beta$—$^1H^\beta$ cross peaks were diagnostic. In those cases, $^1H^\alpha$—$^1H^{\beta'}$ correlations were useful in cases where the α proton showed good separation from the other α protons, e.g. the α proton of Ala(S)3. In cases when the α protons gave ambiguous assignment (e.g. in the case of rings E and G), $^1H^N$—$^1H^\beta$ correlations acquired in a water suppressed NOESY spectrum in 90% $H_2O$/10% $D_2O$ were also taken into consideration to take advantage of the readily distinguishable amide proton chemical shifts. Collectively, this approach allowed assignment of all resonances to individual residues (and therefore the topology of the rings) except for Ala(S)26 and Cys30. The degeneracy of the $^1H^\beta$ chemical shifts of Ala(S) 26 and Cys30 made it impossible to identify ring 6 on the basis of the NMR data. However, the $^1H^\beta$ chemical shifts of Ala(S)26 clearly indicated that it was involved in a ring. Given that the thioether connectivities of all the other Cys residues had been assigned to an Ala(S)/Abu(S), we concluded that Cys30 must form a ring with Dha26.

Structure Determination of Geobacillin II Using Tandem Mass Spectrometry

GeoAII modified by GeoM and treated with GluC was subjected to ESI-MSMS analysis using collision induced dissociation. For tandem MS, 10 µL of the peptide was injected into a BEH C8 column (1.7 µm, 1.0×100 mm), and separated by UPLC using a gradient of 3% mobile phase A (0.1% formic acid in water) to 97% mobile phase B (0.1% formic acid in methanol) over 12 min. The instrument settings used included capillary voltage and cane voltage of 3500 V and 40 V, respectively, 120° C. as source temperature; 300° C. as desolvation temperature, cone gas flow of 150 L/h, and desolvation gas flow of 600 L/h. A transfer collision energy of 4 V was used for both MS and tandem MS, while the trap collision energy was set to 6 V for MS and a fixed energy of 25 V was used for tandem MS.

Chiral Gas Chromatography/Mass Spectrometry (GC/MS) Analysis

Figure 19C:
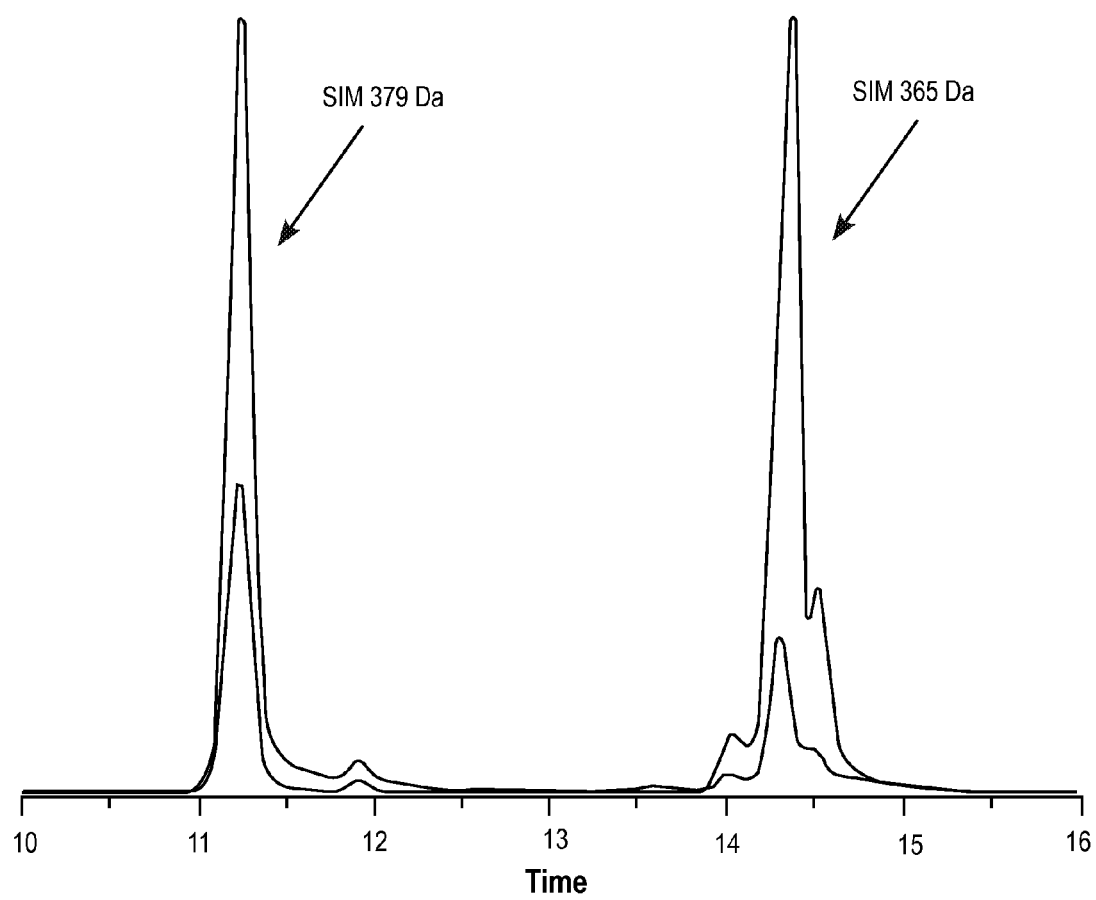

The stereochemical purity of (methyl)lanthionine was determined by acid hydrolysis of geobacillin I and chemical derivatization of the resulting amino acids as previously described (28, 52). The derivatized material was then analyzed by GC/MS. Wild type GeoAI fully modified by GeoB and GeoC in *E. coli* and with its leader attached (1.2 mg) was dissolved in 6 mL of 6 M HCl. The mixture was heated at 110° C. in a sealed tube for 24 h. The reaction was cooled and dried under nitrogen overnight. Methanol (5 mL) was chilled in an ice-water bath, and acetyl chloride (1.5 mL) was added dropwise. This solution was added to the hydrolyzed geobacillin I and heated at 110° C. for 1 h. The sample was cooled and dried under a stream of nitrogen. $CH_2Cl_2$ (3 mL) and pentafluoropropionic anhydride (1 mL) was added and the material was heated at 110° C. for 40 min. The reaction was allowed to cool and dried under a stream of nitrogen. The hydrolyzed and derivatized geobacillin I was taken up in methanol. Nisin A purified from commercial nisaplin was also derivatized using the procedure described above. The derivatized amino acids from geobacillin I, nisin A, as well as synthetic (methyl)lanthionine standards (53) were analyzed by GC/MS using an Agilent HP 5973 mass spectrometer and a Varial CP-Chirasil-L-Val 25 m×0.25 mm×0.15 µM silica column. The samples were introduced to the instrument via a pulsed splitless injection at an inlet temperature of 200° C. and flow rate of 2 ml/min helium gas. The temperature gradient used was 160° C. for 5 min, then 160° C. to 200° C. at 3° C./min. The MS was operated in simultaneous scan/single-ion monitoring (SIM) mode, monitoring at fragment masses of 365 for lanthionine and 379 for methyllanthionine (53). The total ion chromatogram for geobacillin I is shown in FIG. 19A. The derivatized lanthionine and methyllanthionine present in hydrolyzed geobacillin I and nisin A samples are shown in FIGS. 19B and 19C, respectively. FIG. 19B shows GC/MS trace (SIM 379 Da, 365 Da) of derivatized (methyl) lanthionine obtained from geobacillin I (peak with shoulders at 365 Da) overlayed with a GC/MS trace of a synthetic (2S,3S,6R)-methyl-lanthionine standard (largest peak at 379 Da) and a (2S,6R)-lanthionine standard (largest peak at 365 Da, no peak at 379 Da). The intensities were normalized to 1.0 for the largest peak. The small shoulders on the derivatized lanthionine peak have been reported previously and arise from partial epimetization during the acid hydrolysis (52). FIG. 19C shows GC/MS traces (SIM 379 Da, 365 Da) for derivatized (methyl)lanthionine obtained from hydrolyzed geobacillin I (largest peak at 365 Da, smallest peak at 379 Da) compared with derivatized (methyl)lanthionine obtained from nisin A (largest peak at 379 Da; smallest peak at 365 Da). The stereochemistry of the derivatized (methyl) lanthionines is the same for both compounds and the relative ratio of Lan to MeLan of the two compounds is close to the predictions from the structures in FIGS. 4C and 4D (1 Lan, 4 MeLan in nisin A and 4 Lan, 3 MeLan in geobacillin I. The intensities were normalized to 1.0 for the largest peak.

The Lan and MeLan derivatives eluted at identical retention times with (methyl)lanthionine standards confirming that (methyl)lanthionines in nisin and geobacillin I have the same configuration, (2S,3S,6R)-methyllanthionine and (2S,6R)-lanthionine.

Using similar methodology it was determined that geobacillin II contains no methyllanthionines and only lanthionines, consistent with the structure shown in FIG. 4D (see FIG. 19D+19E). Geobacillin II ring A has LL stereochemistry (2R,6R), while the Ring A of certain mutants have a mixture of 2R,6R and 2S,6R stereochemistry.

Figure 20:
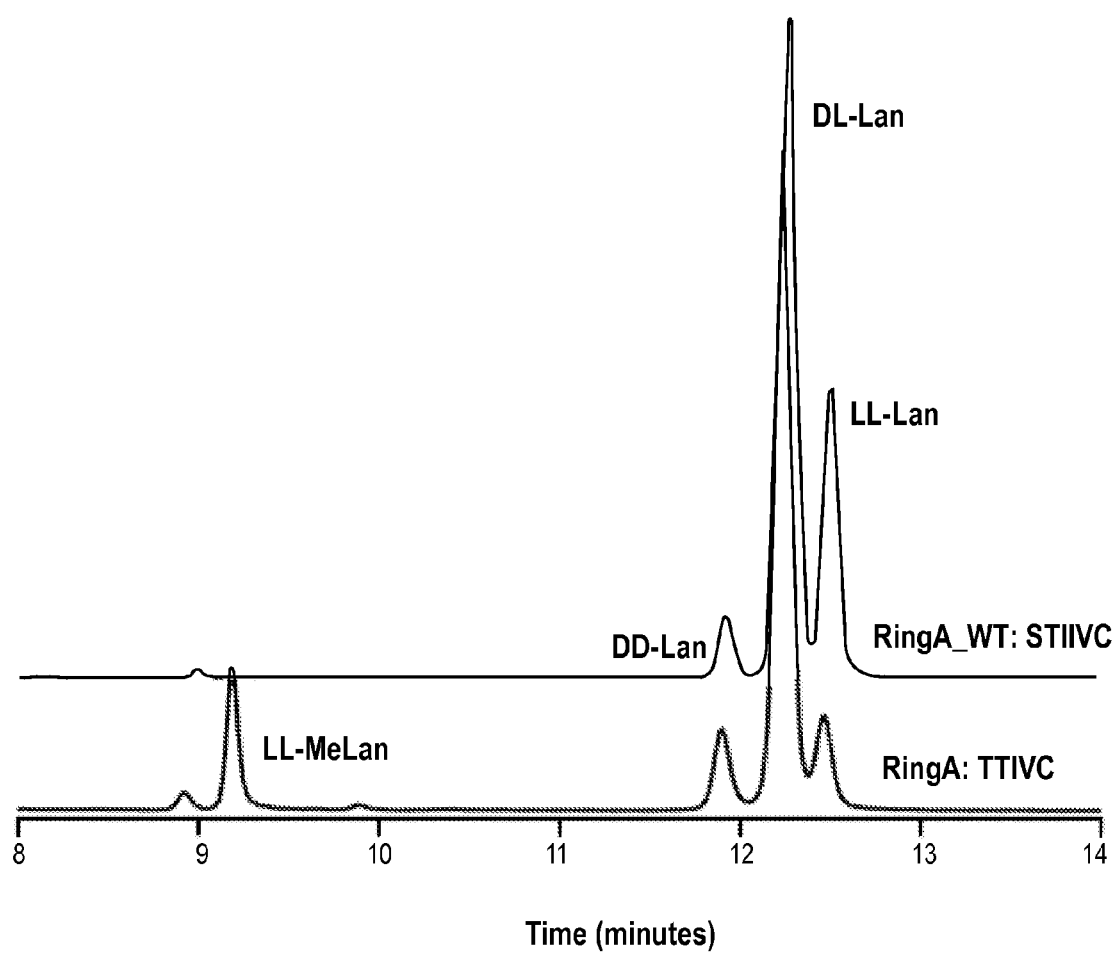
FIG. 20 shows GC/MS trace of derivatized (methyl)lanthionine obtained from geobacillin II (top trace) and geobacillin II-S1T (bottom trace). The intensities were normalized to 1.0 for the largest peak. The small shoulders on the derivatized lanthionine peak arise from partial epimerization during the acid hydrolysis. The appearance of the LL-MeLan peak in the bottom trace and the simultaneous decrease in the intensity of the LL-Lan peak shows that it is the A-ring that had the LL stereochemistry (i.e. when the Lan of the A-ring was mutated to a MeLan by the S1T mutation, it is now the MeLan that has the LL stereochemistry and the original LL-Lan has disappeared).

FIG. 20 shows GC/MS trace of derivatized (methyl) lanthionine obtained from geobacillin II (top trace) and mutant geobacillin II-S1T (bottom trace). The appearance of the LL-MeLan peak in the mutant trace and the simultaneous decrease in the intensity of the LL-Lan peak shows that it is the A-ring that had the LL stereochemistry (i.e., when the Lan of the A-ring was mutated to a MeLan by the S1T mutation, it is now the MeLan that has the LL stereochemistry and the original LL-Lan has disappeared).

Figure 21:
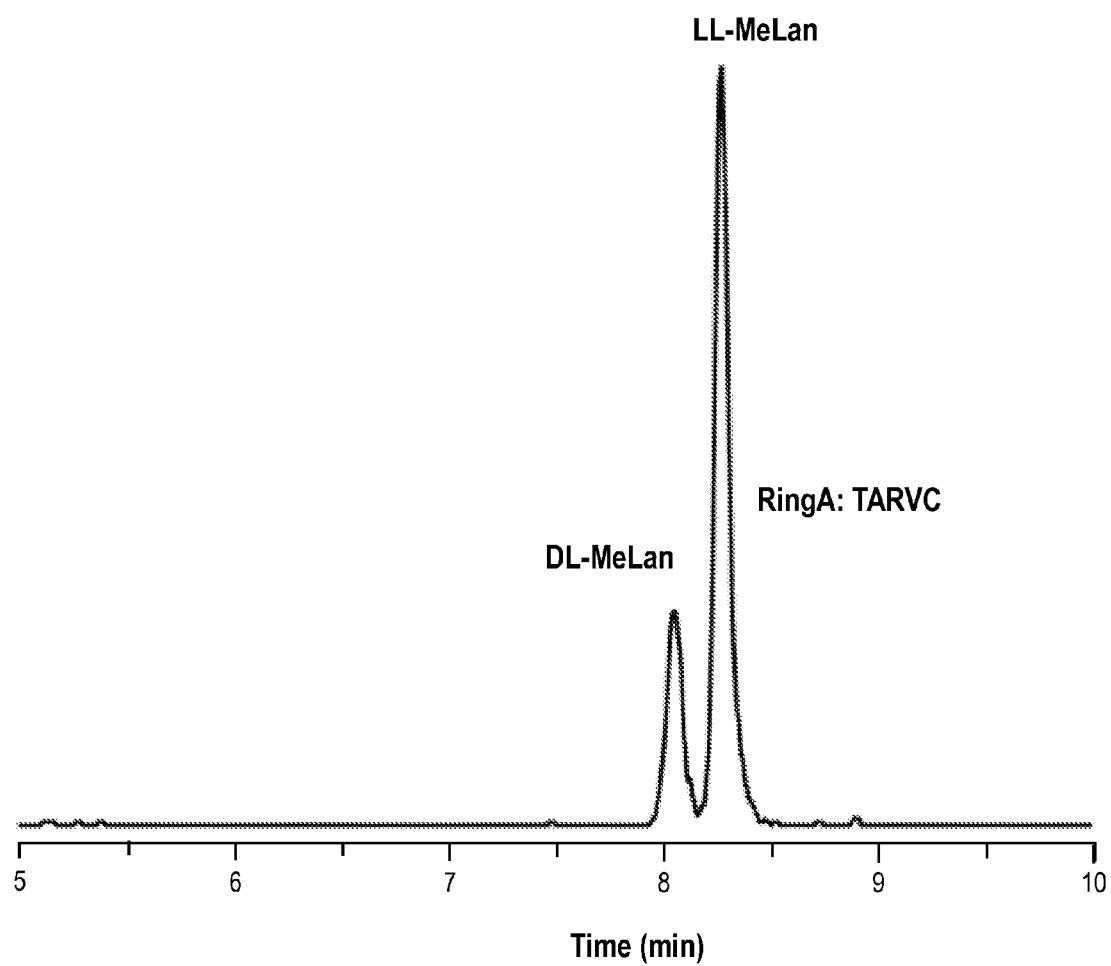
FIG. 21 shows a GC/MS trace of derivatized methyllanthionine obtained from geobacillin II (S1T, T2A, I3R i.e., the S1T mutant has a Ring A amino acid composition of Abu Ala Arg Val Ala (TARVC prior to post-translational modifications) as compared with wild type composition of Ala Dhb Ile Val Ala (prior to post-translational modifications the sequence is STIVC). In this S1T mutant the A-ring is a mixture of LL and DL-stereochemistry.

FIG. 21 shows a GC/MS trace of derivatized methyl-lanthionine obtained from geobacillin II (S1T, T2A, I3R i.e. Ring A amino acid composition is Abu Ala Arg Val Ala (amino acids 1-5) (SEQ ID NO:67) (TARVC (SEQ ID NO:68) prior to post-translational modifications) as compared to wild type composition of Ala Dhb Ile Val Ala (amino acids 1-5) (SEQ ID NO:69) (prior to post-translational modifications the sequence is STIVC (SEQ ID NO:70)). In this mutant the A-ring is a mixture of LL and DL-stereochemistry (mixture of 2R,6R and 2S,6R).

Example 7

Figure 23:
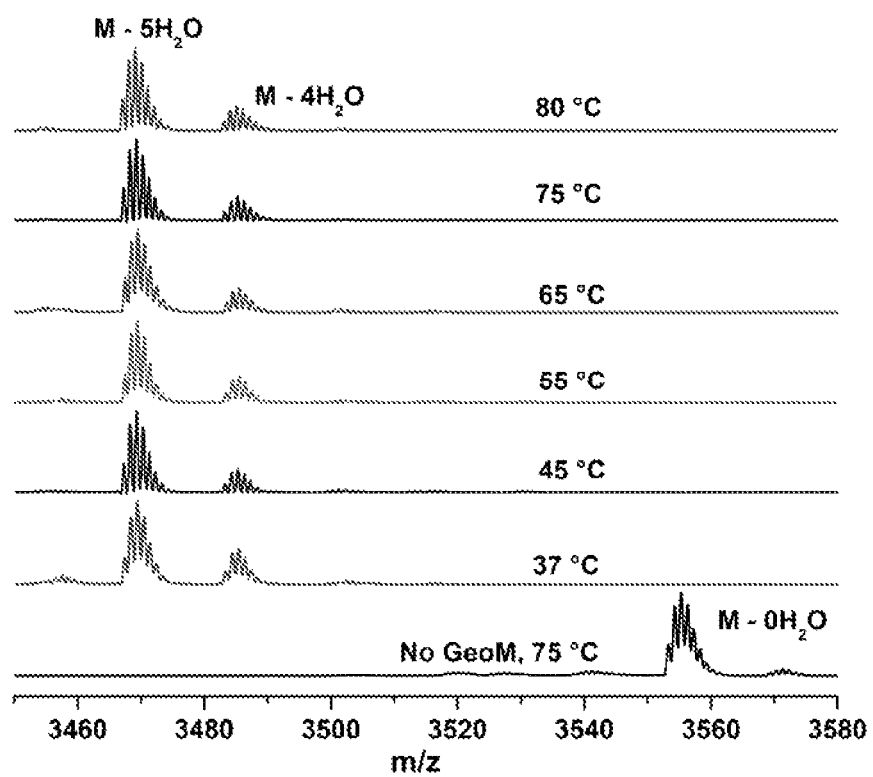
FIG. 23 shows MALDI mass spectrum demonstrating in vitro reconstitution of dehydration activity of GeoM at various temperatures. $His_6$-GeoAII was incubated with $His_6$-GeoM, ATP, $Mg^{2+}$, TCEP in HEPES buffer, pH 7.5.

The synthetic genes for precursor peptide GeoAII and the modification enzyme GeoM were obtained by digestion of the vectors in which they were purchased with the restriction enzymes NdeI/XhoI, and NdeI/HindIII respectively. The amplifications were run on 1% agarose gel and the products were purified using a QIAquick Gel Extraction Kit (QIAGEN). The purified DNA inserts were ligated into the digested pET15b and pET28 vector respectively at 24° C. for 3 hours using T4 DNA ligase. The ligation reaction mixture was diluted 10 times with water prior to the transformation. *E. coli* DH5α cells were transformed with the ligation product using heat shock. Three colonies were picked and grown overnight in LB medium containing appropriate antibiotics based on the plasmid used. The plasmid DNA was isolated using a QIAprep Spin Miniprep Kit (QIAGEN) and the desired sequences of the resulting plasmids (pET15-$His_6$-GeoAII and pET28-$His_6$-GeoM) were confirmed by DNA sequencing using the appropriate primers at the Biotechnology Center of the University of Illinois at Urbana-Champaign. For expression of the precursor peptide GeoAII, chemically competent BL21(DE3) cells were transformed with pET15-$His_6$-GeoAII. An overnight culture from a single colony transformant was used as inoculum for 6 L of LB medium containing 100 μg/L ampicillin, and the culture was grown at 37° C. until the $OD_{600\ nm}$ reached about 0.6. The culture was then induced with 0.5 mM IPTG and the induced cells were grown for an additional 2.5 h. The cells were harvested by centrifugation (11,900×g for 10 min, Beckman JLA-10.500 rotor). The cell pellet was resuspended in 45 mL of start buffer (20 mM Tris, pH 8.0, 500 mM NaCl, 10% glycerol, and lysed with a MultiFlex C3 homogenizer (Avestin). The sample was centrifuged at 23,700×g for 30 min at 4° C. The pellet from this step was homogenized using a sonicator (35% amplitude, 4.4 s pulse, 9.9 s pause for a total of 20 min) in 30 mL of denaturing buffer (6 M guanidine hydrochloride, 20 mM $NaH_2PO_4$, 500 mM NaCL, pH 7.5). The insoluble portion was removed by centrifugation and the supernatant was loaded onto a 5 mL HiTrap HP nickel affinity column. The column was washed with denaturing buffer containing 30 mM imidazole and eluted with 15 mL of denaturing buffer containing 1 M imidazole. Desalting of the eluent was performed using preparative scale RP-HPLC using a Waters Delta-pak C4 PrepPak Cartridge (15 μm; 300 Å; 25×100 mm). A gradient of 2-100% of solvent B (0.086% TFA in 80% acetonitrile/20% water) was used. The fractions containing $His_6$-GeoAII were lyophilized and analyzed by MALDI-TOF MS. For expression of modification enzyme $His_6$-GeoM, chemically competent BL21(DE3) cells were transformed with pET28-$His_6$-GeoM. GeoM is an ATP-dependent enzyme that acts in lanthionine ring formation. Single colony transformants were grown in a 37° C. shaker for 12-15 h in 30 mL of LB medium supplemented with 50 μg/mL kanamycin. These cultures were used to inoculate 4 L of LB media and grown at 37° C. until the $OD_{600}$ was ~0.7. IPTG was added to a final concentration of 0.2 mM and the cultures were grown at 18° C. for an additional 12 h. Cells were harvested by centrifugation at 5000×g for 25 min at 4° C. The cell paste was resuspended in 20 mM Tris-HCl, 500 mM NaCl, 10% glycerol pH-8.0. The cells were lysed using a C3 Homogenizer (Avestin Inc.). The lysed cells were pelleted by centrifugation at 3500×g for 25 min. The purification by nickel column chromatography was accomplished using a 5 mL HiTrap chelating HP nickel affinity column (GE Healthcare) on an AKTA FPLC system (Amersham Pharmacy Biosystems). The supernatant from the centrifugation step was applied to the column using a 50 mL superloop. The protein was detected by absorbance at 280 nm. The column was washed with buffer A containing 1 M NaCl, 20 mM Tris-HCl, pH 8.0, and 30 mM imidazole to remove any non-specifically bound proteins until a flat baseline was observed. A gradient of 0-100% B over 30 min was used to elute the bound proteins where buffer B contained 1 M NaCl, 20 mM Tris-HCl, pH 8.0, and 200 mM imidazole. The most concentrated fraction (4 mL) containing GeoM as determined by SDS-PAGE was loaded onto an S-200 gel filtration column (Amersham Biosciences) equilibrated and eluted with 20 mM HEPES pH 7.5, 100 mM NaCl. The eluted protein was stored at −80° C. until use. The activity assay contained 20 μM $His_6$-GeoAII, 2 μM $His_6$-GeoM, 50 mM HEPES pH 7.5, 1 mM TCEP, 10 mM $MgCl_2$, and 5 mM ATP. The activity assays were incubated at 37° C., 45° C., 55° C., 65° C., 75° C., and 80° C. for 2 h. After 2 h, 1 μM $His_6$-GeoM and 2.5 mM ATP was added and activity assays were incubated for additional 1 h. The product was desalted using a μC18 ziptip and analyzed by MALDI-MS analysis. The results are shown in FIG. 23. GeoM retained biological activity at 37° C., 45° C., 55° C., 65° C., 75° C., and 80° C.

Example 8

Figure 12:
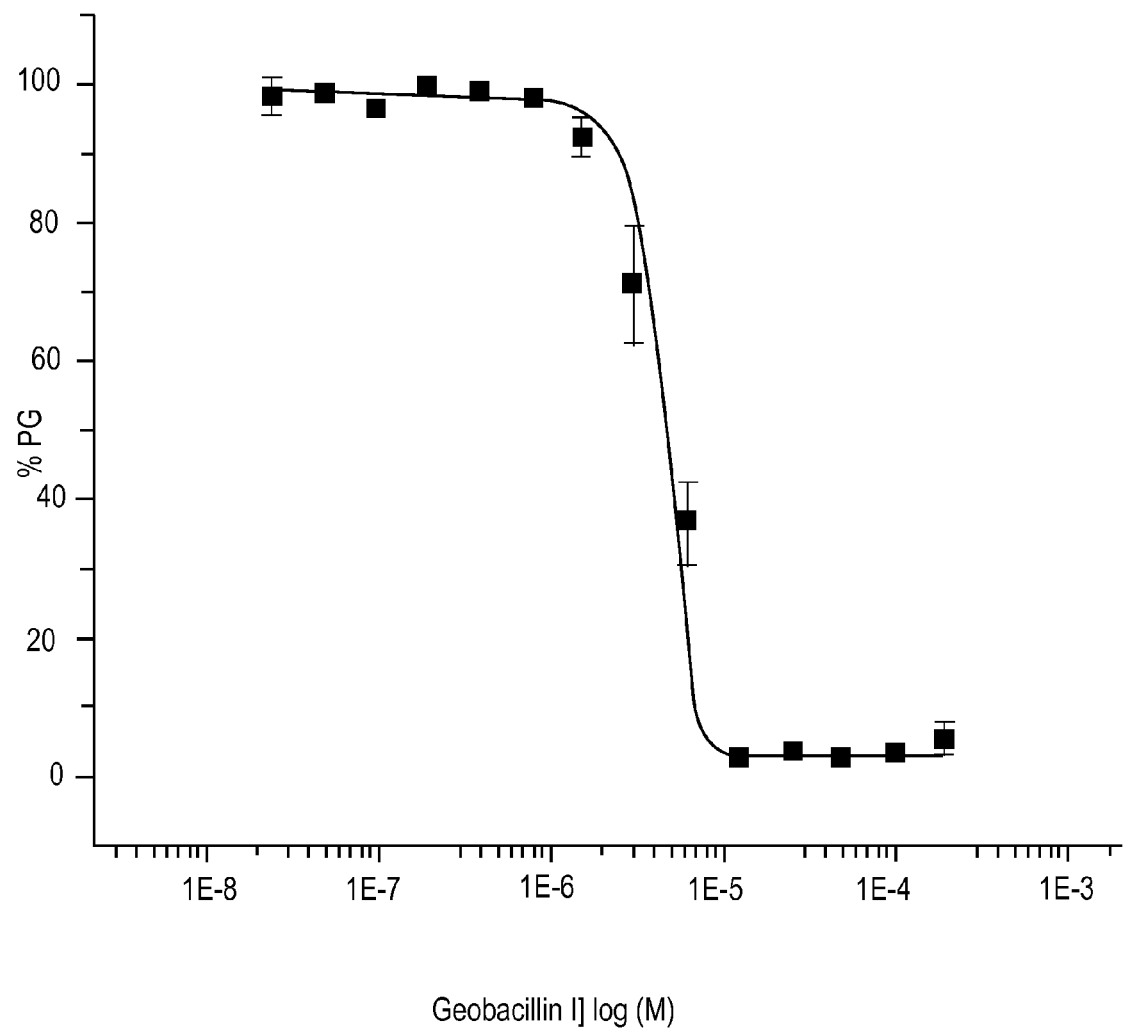
FIG. 12 shows the dose-dependent inhibition of PBP1b-catalyzed formation of peptidoglycan (PG) by geobacillin I.

Geobacillin I has the same mode of action as nisin. That is, it inhibits peptidoglycan formation by binding to lipid II in a dose dependent manner. FIG. 12 shows that the transglycosylase reaction that forms the peptidoglycan is inhibited by geobacillin I.

DISCUSSION

The availability of a rapidly increasing number of bacterial genomes is starting to shift the search for new gene-encoded peptide natural products from activity-based discovery platforms to gene-based discovery approaches (39-41). In the lantibiotic group of compounds, genome mining has resulted in the discovery of several new family members (27, 42, 43), including the first lantibiotic from an alkaliphilic organism (31, 44). In addition, a large number of biosynthetic gene clusters has been identified that remain to be explored experimentally (18, 45). Our attention was drawn to genomes of thermophiles since only one lantibiotic from a thermophilic organism has been reported (46). The lantibiotics produced by such organisms could find potential applications as they may be more stable than lantibiotics produced by mesophilic bacteria. Particularly interesting was the discovery of nisin precursor genes in the genomes of *Geobacillus* because their sequence suggested that the posttranslationally modified products would contain additional rings. Indeed, the masses of the compounds produced by five *Geobacillus* strains and the corresponding lantibiotic heterologously produced in *E. coli* showed nine dehydrations and the NMR structure determined for the latter compound demonstrated seven thioether crosslinks, including conservation of the A and B-rings found in nisin that are important for lipid II binding (4-6). In all, 16 out of the 33 residues in the core peptide of GeoAI are posttranslationally modified, and the final product geobacillin I was shown to have high antimicrobial activity against several pathogens.

This study demonstrates that lantibiotics may be produced in nature at temperatures as high as 50-80° C., the temperature of the deep sub-surface Dagang oilfield where *G. thermodeni-*

*trificans* NG80-2 was isolated. The successful production of geobacillin I and II in *E. coli* was therefore somewhat surprising because many enzymes from thermophilic organisms are usually non-functional at 37° C. However, GeoB, GeoC, and GeoM carried out dehydrations and cyclizations with apparently high efficiency at this temperature. The demonstration that removal of additional amino acids past the double Gly protease cleavage site of geobacillin II resulted in bioactivity along with the sequence homology with other lantibiotics that undergo a second step of proteolytic processing support the lantibiotic structure shown in FIG. 3D.

REFERENCES

1. Willey, J. M. & van der Donk, W. A. (2007) Lantibiotics: peptides of diverse structure and function. *Annu Rev Microbiol*, 61: 477-501.
2. Oman, T. J. & van der Donk, W. A. (2010) Follow the leader: the use of leader peptides to guide natural product biosynthesis. *Nat Chem Biol*, 6: 9-18.
3. Delves-Broughton, J., Blackburn, P., Evans, R. J., & Hugenholtz, J. (1996) Applications of the bacteriocin, nisin. *Antonie Van Leeuwenhoek*, 69: 193-202.
4. Brötz, H., et al. (1998) Role of lipid-bound peptidoglycan precursors in the formation of pores by nisin, epidermin and other lantibiotics. *Mol Microbiol*, 30: 317-327.
5. Breukink, E., et al. (1999) Use of the cell wall precursor lipid II by a pore-forming peptide antibiotic. *Science*, 286: 2361-2364.
6. Hasper, H. E., et al. (2006) A new mechanism of antibiotic action. *Science*, 313: 1636-1637.
7. Breukink, E., et al. (2003) Lipid II is an intrinsic component of the pore induced by nisin in bacterial membranes. *J Biol Chem*, 278: 19898-19903.
8. Wiedemann, I., Benz, R., & Sahl, H. G. (2004) Lipid II-mediated pore formation by the peptide antibiotic nisin: a black lipid membrane study. *J Bacteriol*, 186: 3259-3261.
9. Breukink, E. & de Kruijff, B. (2006) Lipid II as a target for antibiotics. *Nat Rev Drug Discov*, 5: 321-332.
10. Schneider, T. & Sahl, H. G. (2010) Lipid II and other bactoprenol-bound cell wall precursors as drug targets. *Curr Opin Investig Drugs*, 11: 157-164.
11. Chan, W. C., Bycroft, B. W., Lian, L. Y., & Roberts, G. C. K. (1989) Isolation and characterization of two degradation products derived from the peptide antibiotic nisin. *FEBS Lett*, 252: 29-36.
12. Rollema, H. S., Kuipers, O. P., Both, P., de Vos, W. M., & Siezen, R. J. (1995) Improvement of solubility and stability of the antimicrobial peptide nisin by protein engineering. *Appl Environ Microbiol*, 61: 2873-2878.
13. Rollema, H. S., Metzger, J. W., Both, P., Kuipers, O. P., & Siezen, R. J. (1996) Structure and biological activity of chemically modified nisin A species. *Eur J Biochem*, 241: 716-722.
14. Lian, L. Y., et al. (1992) Solution structures of nisin A and its two major degradation products determined by n.m.r. *Biochem J*, 283: 413-420.
15. Cruz, L., Garden, R. W., Kaiser, H. J., & Sweedler, J. V. (1996) Studies of the degradation products of nisin, a peptide antibiotic, using capillary electrophoresis with off-line mass spectrometry. *J Chromatogr A*, 735: 375-385.
16. Olde Riekerink, R. G., Barkema, H. W., & Stryhn, H. (2007) The effect of season on somatic cell count and the incidence of clinical mastitis. *J Dairy Sci*, 90: 1704-1715.
17. Feng, L., et al. (2007) Genome and proteome of long-chain alkane degrading *Geobacillus thermodenitrificans* NG80-2 isolated from a deep-subsurface oil reservoir. *Proc Natl Acad Sci USA*, 104: 5602-5607.
18. Marsh, A. J., O'Sullivan, O., Ross, R. P., Cotter, P. D., & Hill, C. (2010) In silico analysis highlights the frequency and diversity of type 1 lantibiotic gene clusters in genome sequenced bacteria. *BMC Genomics*, 11: 679.
19. Nes, I. F. & Tagg, J. R. (1996) Novel lantibiotics and their pre-peptides. *Antonie Van Leeuwenhoek*, 69: 89-97.
20. Håvarstein, L. S., Diep, D. B., & Nes, I. F. (1995) A family of bacteriocin ABC transporters carry out proteolytic processing of their substrates concomitant with export. *Mol Microbiol*, 16: 229-240.
21. Zeigler, D. R. (2005) Application of a recN sequence similarity analysis to the identification of species within the bacterial genus *Geobacillus*. *Int J Syst Evol Microbiol*, 55: 1171-1179.
22. Stein, T. (2008) Whole-cell matrix-assisted laser desorption/ionization mass spectrometry for rapid identification of bacteriocin/lantibiotic-producing bacteria. *Rapid Commun Mass Spectrom*, 22: 1146-1152.
23. Engelke, G., Gutowski-Eckel, Z., Hammelmann, M., & Entian, K.-D. (1992) Biosynthesis of the lantibiotic nisin: genomic organization and membrane localization of the NisB protein. *Appl Environ Microbiol*, 58: 3730-3743.
24. Shi, Y., Yang, X., Garg, N., & van der Donk, W. A. (2011) Production of lantipeptides in *Escherichia coli*. *J Am Chem Soc*, 133: 2338-2341.
25. Kodani, S., et al. (2004) The SapB morphogen is a lantibiotic-like peptide derived from the product of the developmental gene ramS in *Streptomyces coelicolor*. *Proc Natl Acad Sci USA*, 101: 11448-11453.
26. Kodani, S., Lodato, M. A., Durrant, M. C., Picart, F., & Willey, J. M. (2005) SapT, a lanthionine-containing peptide involved in aerial hyphae formation in the streptomycetes. *Mol Microbiol*, 58: 1368-1380.
27. Goto, Y., et al. (2010) Discovery of unique lanthionine synthetases reveals new mechanistic and evolutionary insights. *PLoS Biol*, 8: e1000339.
28. Li, B., et al. (2010) Catalytic promiscuity in the biosynthesis of cyclic peptide secondary metabolites in planktonic marine cyanobacteria. *Proc Natl Acad Sci USA*, 107: 10430-10435.
29. Holo, H., Jeknic, Z., Daeschel, M., Stevanovic, S., & Nes, I. F. (2001) Plantaricin W from *Lactobacillus plantarum* belongs to a new family of two-peptide lantibiotics. *Microbiology*, 147: 643-651.
30. Cox, C. R., Coburn, P. S., & Gilmore, M. S. (2005) Enterococcal cytolysin: a novel two component peptide system that serves as a bacterial defense against eukaryotic and prokaryotic cells. *Curr Protein Pept Sci*, 6: 77-84.
31. McClerren, A. L., et al. (2006) Discovery and in vitro biosynthesis of haloduracin, a two-component lantibiotic. *Proc Natl Acad Sci USA*, 103: 17243-17248.
32. Caetano, T., Krawczyk, J. M., Mosker, E., Süssmuth, R. D., & Mendo, S. (2011) Heterologous expression, biosynthesis, and mutagenesis of type II lantibiotics from *Bacillus licheniformis* in *Escherichia coli*. *Chem Biol*, 18: 90-100.
33. Cooper, L. E., McClerren, A. L., Chary, A., & van der Donk, W. A. (2008) Structure-activity relationship studies of the two-component lantibiotic haloduracin. *Chem Biol*, 15: 1035-1045.
34. Majchrzykiewicz, J. A., et al. (2010) Production of a class II two-component lantibiotic of *Streptococcus pneumoniae* using the class I nisin synthetic machinery and leader sequence. *Antimicrob Agents Chemother*, 54: 1498-1505.
35. van der Meer, J. R., et al. (1993) Characterization of the *Lactococcus lactis* nisin A operon genes nisP, encoding a subtilisin-like serine protease involved in precursor processing, and nisR, encoding a regulatory protein involved in nisin biosynthesis. *J Bacteriol*, 175: 2578-2588.
36. Li, B., et al. (2010) Catalytic promiscuity in the biosynthesis of cyclic peptide secondary metabolites in planktonic marine cyanobacteria. *Proc Natl Acad Sci USA*, 107: 10430-10435.
37. Tang, W. & van der Donk, W. A. (2011) Structural characterization of four prochlorosins, a novel class of lantipeptides produced by planktonic marine cyanobacteria. submitted.
38. Shenkarev, Z. O., et al. (2010) Isolation, structure elucidation, and synergistic antibacterial activity of a novel two-component lantibiotic lichenicidin from *Bacillus licheniformis* VK21. *Biochemistry*, 49: 6462-6472.
39. Challis, G. L. (2008) Genome mining for novel natural product discovery. *J Med Chem*, 51: 2618-2628.
40. Velásquez, J. E. & van der Donk, W. A. (2011) Genome mining for ribosomally synthesized natural products. *Curr Opin Chem Biol*, 15: 11-21.
41. Kersten, R. D., et al. (2011) A mass spectrometry-guided genome mining approach for natural product peptidogenomics. *Nat Chem Biol*, doi:10.1038/nchembio.1684.
42. Begley, M., Cotter, P. D., Hill, C., & Ross, R. P. (2009) Rational genome mining for LanM proteins leads to the identification of a novel two peptide lantibiotic, lichenicidin. *Appl Environ Microbiol*, 75: 5451-5460.
43. Dischinger, J., Josten, M., Szekat, C., Sahl, H. G., & Bierbaum, G. (2009) Production of the novel two-peptide lantibiotic lichenicidin by *Bacillus licheniformis* DSM 13. *PLoS One*, 4: e6788.
44. Lawton, E. M., Cotter, P. D., Hill, C., & Ross, R. P. (2007) Identification of a novel two-peptide lantibiotic, Haloduracin, produced by the alkaliphile *Bacillus halodurans* C-125. *FEMS Microbiol Lett*, 267: 64-71.
45. Wang, H., Fewer, D. P., & Sivonen, K. (2011) Genome mining demonstrates the widespread occurrence of gene clusters encoding bacteriocins in cyanobacteria. *PLoS One*, 6: e22384.
46. Kabuki, T., Uenishi, H., Seto, Y., Yoshioka, T., & Nakajima, H. (2009) A unique lantibiotic, thermophilin 1277, containing a disulfide bridge and two thioether bridges. *J Appl Microbiol*, 106: 853-862.
47. Velásquez, J. E., Zhang, X., & van der Donk, W. A. (2011) Biosynthesis of the Antimicrobial Peptide Epilancin 15X and its Unusual N-terminal Lactate Moiety. *Chem Biol*, 18: 857-867.
48. Gut, I. M., Prouty, A. M., Ballard, J. D., van der Donk, W. A., & Blanke, S. R. (2008) Inhibition of *Bacillus anthracis* spore outgrowth by nisin. *Antimicrob Agents Chemother*, 52: 4281-4288.
49. Delaglio, F., et al. (1995) NMRPipe—a multidimensional spectral processing system based on unix pipes. *J. Biomolecular NMR*, 6: 277-293.
50. Goddard, T. D. & Kneller, D. G. (2005) Sparky. Sparky, University of California, San Francisco.
51. Ekkelenkamp, M. B., et al. (2005) Isolation and structural characterization of epilancin 15X, a novel lantibiotic from a clinical strain of *Staphylococcus epidermidis*. *FEBS Lett*, 579: 1917-1922.
52. Ross, A. C., et al. (2010) Synthesis of the lantibiotic lactocin S using peptide cyclizations on solid phase. *J Am Chem Soc*, 132: 462-463.
53. Liu, W., et al. (2011) Solid supported chemical syntheses of both components of the lantibiotic lacticin 3147. *J Am Chem Soc*, 133: 14216-14219.

We claim:

1. An isolated geobacillin comprising the structure of:

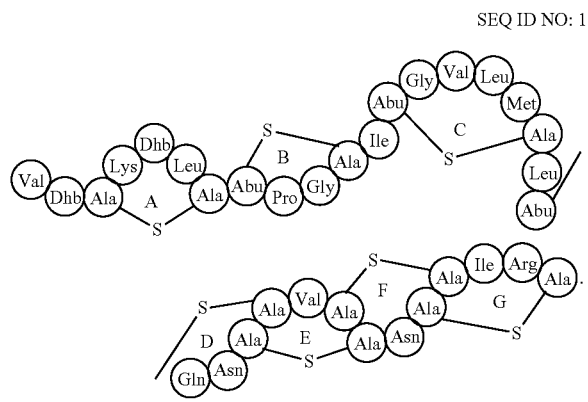

SEQ ID NO: 1

2. The isolated geobacillin of claim 1, wherein the structure has the following amino acid substitutions: Dha5Phe, or Leu6Ile, or both Dha5Phe and Leu6Ile.

3. The isolated geobacillin of claim 1, wherein the A ring has LL (2R,6R) stereochemistry or has a mixture of LL stereochemistry and DL-stereochemistry (2R,6R and 2S,6R).

4. An antimicrobial composition comprising one or more isolated geobacillins of claim 1 and a pharmaceutically acceptable carrier, pharmaceutically acceptable diluent, phosphate buffer, MOPS buffer, other diluent, or excipient.

5. The antimicrobial composition of claim 4, wherein the composition retains 80% or more biological activity at temperatures between about 55° C. to 80° C.

6. The antimicrobial composition of claim 4, wherein the composition further comprises at least one antifungal agent, one additional antimicrobial agent, or a membrane disrupting agent.

7. The antimicrobial composition of claim 6, wherein the one additional antimicrobial agent has Gram negative bacteriostatic or bacteriocidal activity and the membrane disrupting agent renders Gram negative bacteria susceptible to the one or more geobacillins.

8. The antimicrobial composition of claim 4, wherein the one or more isolated geobacillins are present in the composition at about 0.001, 0.01, 0.1, 1, 5, 10, 20, 30, 40, 50, 75, 100, or 150 mg/kg.

9. A method of reducing reproduction of bacteria or reducing numbers of bacteria present in or on a subject, comprising administering to the subject a therapeutically effective amount of the antimicrobial composition of claim 4.

10. The method of claim 9, wherein the subject is a human.

11. The method of claim 9, wherein the antimicrobial composition is administered orally, topically, nasally, buccally, sublingually, transmucosally, rectally, transdermally, by inhalation, by injection or intrathecally.

12. The method of claim 11, wherein the injection is intravenous, intrapulmonary, intramuscular, intradermal, intraperitoneal, intrathecal, or subcutaneous injection.

13. A preservative comprising an effective amount of one or more geobacillins of claim 1 in a physiological solution at a pH of between 3 and 8.

14. A food or beverage composition comprising an amount of one or more geobacillins of claim 1 sufficient to reduce the reproduction of bacteria or numbers of bacteria in the composition.

15. A method of reducing reproduction of bacteria or reducing numbers of bacteria present in or on a composition or object, comprising contacting the antimicrobial composition of claim 4 with the composition or object for a period effective to reduce reproduction of bacteria or reduce numbers of bacteria in or on the composition or object.

16. The method of claim 15, wherein the composition is a food or beverage.

17. A method of reducing a biofilm or biofouling condition comprising contacting the antimicrobial composition of claim 4 with the biofilm or biofouling condition for a period effective to reduce reproduction of bacteria or reduce numbers of bacteria in or on the biofilm or biofouling condition.

18. A kit comprising one or more geobacillins of claim 1 and one or more applicators.

19. A method for producing an isolated geobacillin of claim 1, comprising:
 (a) inserting an enzyme cleavage site within 10 nucleotides of the −1 position of a nucleic acid molecule encoding GeoA1 to make a mutated GeoA1 nucleic acid molecule;
 (b) inserting the mutated GeoA1 nucleic acid molecule and nucleic acid molecules that encode GeoB, GeoC, GeoAII, and GeoM into one or more cloning vectors;
 (c) transforming a culture of bacterial cells with the one or more cloning vectors;
 (d) lysing the bacterial cells and collecting the cell lysate;
 (e) treating the cell lysate with an enzyme that will cause cleavage at the enzyme cleavage site;
 (f) and isolating the geobacillin from the cell lysate to produce an isolated geobacillin of claim 1.

20. The method of claim 19, wherein the nucleic acid molecules encoding GeoA1, GeoB, GeoC, GeoAII, and GeoM are codon optimized for expression in the bacterial cells.

21. The method of claim 20, wherein the bacterial cells are *Escherichia coli*.

* * * * *

SEQUENCE LISTING

```
<160> NUMBER OF SEQ ID NOS: 70

<210> SEQ ID NO 1
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Dhb amino acid
<220> FEATURE:
<221> NAME/KEY: DISULFID
<222> LOCATION: (3)..(7)
<220> FEATURE:
<221> NAME/KEY: MISC_FEATURE
<222> LOCATION: (5)..(5)
<223> OTHER INFORMATION: Xaa is Dha amino acid
<220> FEATURE:
<221> NAME/KEY: DISULFID
<222> LOCATION: (8)..(11)
<220> FEATURE:
<221> NAME/KEY: MOD_RES
<222> LOCATION: (8)..(8)
<223> OTHER INFORMATION: Abu
<220> FEATURE:
<221> NAME/KEY: DISULFID
<222> LOCATION: (13)..(18)
<220> FEATURE:
<221> NAME/KEY: MOD_RES
<222> LOCATION: (13)..(13)
<223> OTHER INFORMATION: Abu
<220> FEATURE:
<221> NAME/KEY: DISULFID
<222> LOCATION: (20)..(24)
```

```
<220> FEATURE:
<221> NAME/KEY: MOD_RES
<222> LOCATION: (20)..(20)
<223> OTHER INFORMATION: Abu
<220> FEATURE:
<221> NAME/KEY: DISULFID
<222> LOCATION: (23)..(27)
<220> FEATURE:
<221> NAME/KEY: DISULFID
<222> LOCATION: (26)..(30)
<220> FEATURE:
<221> NAME/KEY: DISULFID
<222> LOCATION: (29)..(33)

<400> SEQUENCE: 1

Val Xaa Ala Lys Xaa Leu Ala Xaa Pro Gly Ala Ile Xaa Gly Val Leu
1               5                   10                  15

Met Ala Leu Xaa Gln Asn Ala Ala Val Ala Ala Asn Ala Ala Ile Arg
            20                  25                  30

Ala

<210> SEQ ID NO 2
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Dhb amino acid
<220> FEATURE:
<221> NAME/KEY: DISULFID
<222> LOCATION: (3)..(7)
<220> FEATURE:
<221> NAME/KEY: MISC_FEATURE
<222> LOCATION: (5)..(5)
<223> OTHER INFORMATION: Xaa is Dha amino acid
<220> FEATURE:
<221> NAME/KEY: MOD_RES
<222> LOCATION: (8)..(8)
<223> OTHER INFORMATION: Abu
<220> FEATURE:
<221> NAME/KEY: DISULFID
<222> LOCATION: (8)..(11)
<220> FEATURE:
<221> NAME/KEY: MOD_RES
<222> LOCATION: (13)..(13)
<223> OTHER INFORMATION: Abu
<220> FEATURE:
<221> NAME/KEY: DISULFID
<222> LOCATION: (13)..(19)
<220> FEATURE:
<221> NAME/KEY: MOD_RES
<222> LOCATION: (23)..(23)
<223> OTHER INFORMATION: Abu
<220> FEATURE:
<221> NAME/KEY: DISULFID
<222> LOCATION: (23)..(26)
<220> FEATURE:
<221> NAME/KEY: MOD_RES
<222> LOCATION: (25)..(25)
<223> OTHER INFORMATION: Abu
<220> FEATURE:
<221> NAME/KEY: DISULFID
<222> LOCATION: (25)..(28)
<220> FEATURE:
<221> NAME/KEY: MISC_FEATURE
<222> LOCATION: (33)..(33)
<223> OTHER INFORMATION: Xaa is Dha amino acid

<400> SEQUENCE: 2

Ile Xaa Ala Ile Xaa Leu Ala Xaa Pro Gly Ala Lys Xaa Gly Ala Leu
1               5                   10                  15
```

```
Met Gly Ala Asn Met Lys Xaa Ala Xaa Ala His Ala Ser Ile His Val
            20                  25                  30

Xaa Lys
```

```
<210> SEQ ID NO 3
<211> LENGTH: 56
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Optinally L
<220> FEATURE:
<221> NAME/KEY: MISC_FEATURE
<222> LOCATION: (19)..(19)
<223> OTHER INFORMATION: Optinally I
<220> FEATURE:
<221> NAME/KEY: MISC_FEATURE
<222> LOCATION: (23)..(23)
<223> OTHER INFORMATION: Optinally N

<400> SEQUENCE: 3
```

```
Met Ala Lys Phe Asp Asp Phe Asp Leu Asp Ile Val Val Lys Lys Gln
1               5                   10                  15

Asp Asp Val Val Gln Pro Lys Val Thr Ser Lys Ser Leu Cys Thr Pro
            20                  25                  30

Gly Cys Ile Thr Gly Val Leu Met Cys Leu Thr Gln Asn Ser Cys Val
        35                  40                  45

Ser Cys Asn Ser Cys Ile Arg Cys
    50                  55
```

```
<210> SEQ ID NO 4
<211> LENGTH: 69
<212> TYPE: PRT
<213> ORGANISM: Artificial Sequence
<220> FEATURE:
<223> OTHER INFORMATION: Synthetic

<400> SEQUENCE: 4
```

```
Gly Ser Ser His His His His His His Ser Gln Asp Pro Met Ala Lys
1               5                   10                  15

Phe Asp Asp Phe Asp Leu Asp Ile Val Val Lys Lys Gln Asp Asp Val
            20                  25                  30

Val Gln Pro Lys Val Thr Ser Lys Ser Leu Cys Thr Pro Gly Cys Ile
        35                  40                  45

Thr Gly Val Leu Met Cys Leu Thr Gln Asn Ser Cys Val Ser Cys Asn
    50                  55                  60

Ser Cys Ile Arg Cys
65
```

```
<210> SEQ ID NO 5
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (36)..(36)
<223> OTHER INFORMATION: optionally K

<400> SEQUENCE: 5
```

Met Lys Gly Gly Ile Gln Met Glu Lys Gln Glu Gln Thr Phe Val Ser
1               5                   10                  15

Lys Ile Ser Glu Glu Leu Lys Lys Leu Ala Gly Gly Tyr Thr Glu
            20                  25                  30

Val Ser Pro Gln Ser Thr Ile Val Cys Val Ser Leu Arg Ile Cys Asn
        35                  40                  45

Trp Ser Leu Arg Phe Cys Pro Ser Phe Lys Val Arg Cys Pro Met
    50                  55                  60

<210> SEQ ID NO 6
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (36)..(36)
<223> OTHER INFORMATION: optionally K

<400> SEQUENCE: 6

Met Lys Gly Gly Ile Gln Met Glu Lys Gln Glu Gln Thr Phe Val Ser
1               5                   10                  15

Lys Ile Ser Glu Glu Leu Lys Lys Leu Ala Gly Gly Tyr Thr Glu
            20                  25                  30

Val Ser Pro Gln
        35

<210> SEQ ID NO 7
<211> LENGTH: 38
<212> TYPE: DNA
<213> ORGANISM: Artificial Sequence
<220> FEATURE:
<223> OTHER INFORMATION: Synthetic

<400> SEQUENCE: 7
ctagatggat ccgatggcca aatttgatga ttttgatc                              38

<210> SEQ ID NO 8
<211> LENGTH: 39
<212> TYPE: DNA
<213> ORGANISM: Artificial Sequence
<220> FEATURE:
<223> OTHER INFORMATION: Synthetic

<400> SEQUENCE: 8
ctagaagctt ttattagcaa cgaatacagc tattacagc                             39

<210> SEQ ID NO 9
<211> LENGTH: 38
<212> TYPE: DNA
<213> ORGANISM: Artificial Sequence
<220> FEATURE:
<223> OTHER INFORMATION: Synthetic

<400> SEQUENCE: 9
acagccgcat atgaatgatc tggtgtttaa aaatattg                              38

<210> SEQ ID NO 10
<211> LENGTH: 38
<212> TYPE: DNA
<213> ORGANISM: Artificial Sequence
<220> FEATURE:
<223> OTHER INFORMATION: Synthetic

<400> SEQUENCE: 10
tctagctcga gttaattttt cagcaccagg ccatgggc                              38

<210> SEQ ID NO 11
<211> LENGTH: 37
<212> TYPE: DNA
<213> ORGANISM: Artificial Sequence
<220> FEATURE:
<223> OTHER INFORMATION: Synthetic

<400> SEQUENCE: 11
aagcagccgc atatgtctat tagcatgaaa gccctgg                               37

<210> SEQ ID NO 12
<211> LENGTH: 41
<212> TYPE: DNA
<213> ORGANISM: Artificial Sequence
<220> FEATURE:
<223> OTHER INFORMATION: Synthetic

<400> SEQUENCE: 12
ctagctcgag taaaacttcg ctcagcagaa atgcacaatc c                          41

<210> SEQ ID NO 13
<211> LENGTH: 42
<212> TYPE: DNA
<213> ORGANISM: Artificial Sequence
<220> FEATURE:
<223> OTHER INFORMATION: Synthetic

<400> SEQUENCE: 13
caggatgatg ttgttcagcc gaaagttacc agcaaaagcc tg                         42

<210> SEQ ID NO 14
<211> LENGTH: 30
<212> TYPE: DNA
<213> ORGANISM: Artificial Sequence
<220> FEATURE:
<223> OTHER INFORMATION: Synthetic

<400> SEQUENCE: 14
cggctgaaca acatcatcct gttttttcac                                      30

<210> SEQ ID NO 15
<211> LENGTH: 35
<212> TYPE: DNA
<213> ORGANISM: Artificial Sequence
<220> FEATURE:
<223> OTHER INFORMATION: Synthetic

<400> SEQUENCE: 15
ctagatggat ccgatgaaag gtggcattca gatgg                                35

<210> SEQ ID NO 16
<211> LENGTH: 36
<212> TYPE: DNA
<213> ORGANISM: Artificial Sequence
<220> FEATURE:
<223> OTHER INFORMATION: Synthetic

<400> SEQUENCE: 16
ctagaagctt ttacatcgga caacgaactt taaagc                               36

<210> SEQ ID NO 17
<211> LENGTH: 37

-continued

<210> SEQ ID NO 17
<211> LENGTH: 37 [inferred]
<212> TYPE: DNA
<213> ORGANISM: Artificial Sequence
<220> FEATURE:
<223> OTHER INFORMATION: Synthetic

<400> SEQUENCE: 17
aagcagccgc atatgaacga aatcgtggaa aataacc                          37

<210> SEQ ID NO 18
<211> LENGTH: 38
<212> TYPE: DNA
<213> ORGANISM: Artificial Sequence
<220> FEATURE:
<223> OTHER INFORMATION: Synthetic

<400> SEQUENCE: 18
ctagctcgag ttaatggttc agctgcagag tcagcacg                         38

<210> SEQ ID NO 19
<211> LENGTH: 37
<212> TYPE: DNA
<213> ORGANISM: Artificial Sequence
<220> FEATURE:
<223> OTHER INFORMATION: Synthetic

<400> SEQUENCE: 19
gaaaaaactg gctggcaaat ataccgaagt ttctccg                          37

<210> SEQ ID NO 20
<211> LENGTH: 29
<212> TYPE: DNA
<213> ORGANISM: Artificial Sequence
<220> FEATURE:
<223> OTHER INFORMATION: Synthetic

<400> SEQUENCE: 20
gccagccagt tttttcagtt cttcttcgc                                   29

<210> SEQ ID NO 21
<211> LENGTH: 39
<212> TYPE: DNA
<213> ORGANISM: Artificial Sequence
<220> FEATURE:
<223> OTHER INFORMATION: Synthetic

<400> SEQUENCE: 21
gttataccga agtttctccg gaaagcacca ttgtttgtg                        39

<210> SEQ ID NO 22
<211> LENGTH: 30
<212> TYPE: DNA
<213> ORGANISM: Artificial Sequence
<220> FEATURE:
<223> OTHER INFORMATION: Synthetic

<400> SEQUENCE: 22
cggagaaact tcggtatatt tgccagccag                                  30

<210> SEQ ID NO 23
<211> LENGTH: 39
<212> TYPE: DNA
<213> ORGANISM: Artificial Sequence
<220> FEATURE:
<223> OTHER INFORMATION: Synthetic

<400> SEQUENCE: 23
gttataccga agtttctccg aaaagcacca ttgtttgtg          39

<210> SEQ ID NO 24
<211> LENGTH: 30
<212> TYPE: DNA
<213> ORGANISM: Artificial Sequence
<220> FEATURE:
<223> OTHER INFORMATION: Synthetic

<400> SEQUENCE: 24
cggagaaact tcggtataac cgccagccag          30

<210> SEQ ID NO 25
<211> LENGTH: 34
<212> TYPE: PRT
<213> ORGANISM: Artificial Sequence
<220> FEATURE:
<223> OTHER INFORMATION: Synthetic

<400> SEQUENCE: 25

Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30

Ser Lys

<210> SEQ ID NO 26
<211> LENGTH: 32
<212> TYPE: PRT
<213> ORGANISM: Artificial Sequence
<220> FEATURE:
<223> OTHER INFORMATION: Synthetic

<400> SEQUENCE: 26

Trp Lys Ser Glu Ser Leu Cys Thr Pro Gly Cys Val Thr Gly Ala Leu
1               5                   10                  15

Gln Thr Cys Phe Leu Gln Thr Leu Thr Cys Asn Cys Lys Ile Ser Lys
            20                  25                  30

<210> SEQ ID NO 27
<211> LENGTH: 32
<212> TYPE: PRT
<213> ORGANISM: Artificial Sequence
<220> FEATURE:
<223> OTHER INFORMATION: Synthetic

<400> SEQUENCE: 27

Trp Lys Ser Glu Ser Val Cys Thr Pro Gly Cys Val Thr Gly Val Leu
1               5                   10                  15

Gln Thr Cys Phe Leu Gln Thr Ile Thr Cys Asn Cys His Ile Ser Lys
            20                  25                  30

<210> SEQ ID NO 28
<211> LENGTH: 33
<212> TYPE: PRT
<213> ORGANISM: Artificial Sequence
<220> FEATURE:
<223> OTHER INFORMATION: Synthetic

<400> SEQUENCE: 28

Val Thr Ser Lys Ser Leu Cys Thr Pro Gly Cys Ile Thr Gly Val Leu
1               5                   10                  15

Met Cys Leu Thr Gln Asn Ser Cys Val Ser Cys Asn Ser Cys Ile Arg
            20                  25                  30

Cys

<210> SEQ ID NO 29
<211> LENGTH: 33
<212> TYPE: PRT
<213> ORGANISM: Artificial Sequence
<220> FEATURE:
<223> OTHER INFORMATION: Synthetic

<400> SEQUENCE: 29

Ile Thr Ser Lys Ser Leu Cys Thr Pro Gly Cys Ile Thr Gly Ile Leu
1               5                   10                  15

Met Cys Leu Thr Gln Asn Ser Cys Val Ser Cys Asn Ser Cys Ile Arg
            20                  25                  30

Cys

<210> SEQ ID NO 30
<211> LENGTH: 23
<212> TYPE: PRT
<213> ORGANISM: Artificial Sequence
<220> FEATURE:
<223> OTHER INFORMATION: Synthetic

<400> SEQUENCE: 30

Met Ser Thr Lys Asp Phe Asn Leu Asp Leu Val Ser Val Ser Lys Lys
1               5                   10                  15

Asp Ser Gly Ala Ser Pro Arg
            20

<210> SEQ ID NO 31
<211> LENGTH: 24
<212> TYPE: PRT
<213> ORGANISM: Artificial Sequence
<220> FEATURE:
<223> OTHER INFORMATION: Synthetic

<400> SEQUENCE: 31

Met Ser Lys Phe Asp Asp Phe Asp Leu Asp Val Val Lys Val Ser Lys
1               5                   10                  15

Gln Asp Ser Lys Ile Thr Pro Gln
            20

<210> SEQ ID NO 32
<211> LENGTH: 27
<212> TYPE: PRT
<213> ORGANISM: Artificial Sequence
<220> FEATURE:
<223> OTHER INFORMATION: Synthetic

<400> SEQUENCE: 32

Met Thr Asn Met Ser Lys Phe Asp Asp Phe Asp Leu Asp Val Val Lys
1               5                   10                  15

Val Ser Lys Gln Asp Ser Lys Ile Thr Pro Gln
            20                  25

<210> SEQ ID NO 33
<211> LENGTH: 23
<212> TYPE: PRT
<213> ORGANISM: Artificial Sequence
<220> FEATURE:
<223> OTHER INFORMATION: Synthetic

<400> SEQUENCE: 33

Met Ala Lys Phe Asp Asp Phe Asp Leu Asp Ile Val Val Lys Lys Gln
1               5                   10                  15

Asp Asp Val Val Gln Pro Asn
            20

<210> SEQ ID NO 34
<211> LENGTH: 23
<212> TYPE: PRT
<213> ORGANISM: Artificial Sequence
<220> FEATURE:
<223> OTHER INFORMATION: Synthetic

<400> SEQUENCE: 34

Met Ala Lys Leu Asp Asp Phe Asp Leu Asp Ile Val Val Lys Lys Gln
1               5                   10                  15

Asp Asn Ile Val Gln Pro Asn
            20

<210> SEQ ID NO 35
<211> LENGTH: 32
<212> TYPE: PRT
<213> ORGANISM: Artificial Sequence
<220> FEATURE:
<223> OTHER INFORMATION: Synthetic

<400> SEQUENCE: 35

Gly Ser Gly Asp Val His Ala Gln Thr Thr Trp Pro Cys Ala Thr Val
1               5                   10                  15

Gly Val Ser Val Ala Leu Cys Pro Thr Thr Lys Cys Thr Ser Gln Cys
            20                  25                  30

<210> SEQ ID NO 36
<211> LENGTH: 40
<212> TYPE: PRT
<213> ORGANISM: Artificial Sequence
<220> FEATURE:
<223> OTHER INFORMATION: Synthetic

<400> SEQUENCE: 36

Gly Ala Gly Asp Pro Glu Ala Arg Ser Gly Ile Pro Cys Thr Ile Gly
1               5                   10                  15

Ala Ala Val Ala Ala Ser Ile Ala Val Cys Pro Thr Thr Lys Cys Ser
            20                  25                  30

Lys Arg Cys Gly Lys Arg Lys Lys
            35                  40

<210> SEQ ID NO 37
<211> LENGTH: 34
<212> TYPE: PRT
<213> ORGANISM: Artificial Sequence
<220> FEATURE:
<223> OTHER INFORMATION: Synthetic

<400> SEQUENCE: 37

Ala Ala Gly Thr Pro Leu Ala Leu Leu Gly Gly Ala Thr Gly Val
1               5                   10                  15

Ile Gly Tyr Ile Ser Asn Gln Thr Cys Pro Thr Thr Ala Cys Thr Arg
            20                  25                  30

Ala Cys

<210> SEQ ID NO 38
<211> LENGTH: 29
<212> TYPE: PRT

<213> ORGANISM: Artificial Sequence
<220> FEATURE:
<223> OTHER INFORMATION: Synthetic

<400> SEQUENCE: 38

Gly Ser Gly Asp Val Gln Ala Glu Thr Thr Pro Ala Cys Phe Thr Ile
1               5                   10                  15

Gly Leu Gly Val Gly Ala Leu Phe Ser Ala Lys Phe Cys
            20                  25

<210> SEQ ID NO 39
<211> LENGTH: 40
<212> TYPE: PRT
<213> ORGANISM: Artificial Sequence
<220> FEATURE:
<223> OTHER INFORMATION: Synthetic

<400> SEQUENCE: 39

Gly Gly Asn Asp Val Asn Pro Glu Thr Thr Pro Ala Thr Thr Ser Ser
1               5                   10                  15

Trp Thr Cys Ile Thr Ala Gly Val Thr Val Ser Ala Ser Leu Cys Pro
            20                  25                  30

Thr Thr Lys Cys Thr Ser Arg Cys
        35                  40

<210> SEQ ID NO 40
<211> LENGTH: 36
<212> TYPE: PRT
<213> ORGANISM: Artificial Sequence
<220> FEATURE:
<223> OTHER INFORMATION: Synthetic

<400> SEQUENCE: 40

Gly Gly Tyr Thr Glu Val Ser Pro Gln Ser Thr Ile Val Cys Val Ser
1               5                   10                  15

Leu Arg Ile Cys Asn Trp Ser Leu Arg Phe Cys Pro Ser Phe Lys Val
            20                  25                  30

Arg Cys Pro Met
        35

<210> SEQ ID NO 41
<211> LENGTH: 36
<212> TYPE: PRT
<213> ORGANISM: Artificial Sequence
<220> FEATURE:
<223> OTHER INFORMATION: Synthetic

<400> SEQUENCE: 41

Gly Gly Tyr Thr Glu Val Ser Pro Gln Ser Thr Ile Val Cys Val Ser
1               5                   10                  15

Leu Arg Ile Cys Asn Trp Ser Leu Arg Phe Cys Pro Ser Phe Lys Val
            20                  25                  30

Lys Cys Pro Met
        35

<210> SEQ ID NO 42
<211> LENGTH: 27
<212> TYPE: PRT
<213> ORGANISM: Artificial Sequence
<220> FEATURE:
<223> OTHER INFORMATION: Synthetic

<400> SEQUENCE: 42

```
Met Lys Gly Gly Ile Gln Met Glu Lys Gln Glu Gln Thr Phe Val Ser
1               5                   10                  15

Lys Ile Ser Glu Glu Glu Leu Lys Lys Leu Ala
            20                  25
```

<210> SEQ ID NO 43
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is Dha amino acid
<220> FEATURE:
<221> NAME/KEY: MISC_FEATURE
<222> LOCATION: (6)..(6)
<223> OTHER INFORMATION: Xaa is Dhb amino acid
<220> FEATURE:
<221> NAME/KEY: MISC_FEATURE
<222> LOCATION: (11)..(11)
<223> OTHER INFORMATION: Xaa is Dha amino acid
<220> FEATURE:
<221> NAME/KEY: MISC_FEATURE
<222> LOCATION: (18)..(18)
<223> OTHER INFORMATION: Xaa is Dha amino acid
<220> FEATURE:
<221> NAME/KEY: MISC_FEATURE
<222> LOCATION: (24)..(24)
<223> OTHER INFORMATION: Xaa is Dha amino acid

<400> SEQUENCE: 43

```
Val Ser Pro Gln Xaa Xaa Ile Val Cys Val Xaa Leu Arg Ile Cys Asn
1               5                   10                  15

Trp Xaa Leu Arg Phe Cys Pro Xaa Phe Lys Val Arg Cys Pro Met
            20                  25                  30
```

<210> SEQ ID NO 44
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Dha amino acid
<220> FEATURE:
<221> NAME/KEY: MISC_FEATURE
<222> LOCATION: (2)..(2)
<223> OTHER INFORMATION: Xaa is Dhb amino acid
<220> FEATURE:
<221> NAME/KEY: MISC_FEATURE
<222> LOCATION: (7)..(7)
<223> OTHER INFORMATION: Xaa is Dha amino acid
<220> FEATURE:
<221> NAME/KEY: MISC_FEATURE
<222> LOCATION: (14)..(14)
<223> OTHER INFORMATION: Xaa is Dha amino acid
<220> FEATURE:
<221> NAME/KEY: MISC_FEATURE
<222> LOCATION: (20)..(20)
<223> OTHER INFORMATION: Xaa is Dha amino acid

<400> SEQUENCE: 44

```
Xaa Xaa Ile Val Cys Val Xaa Leu Arg Ile Cys Asn Trp Xaa Leu Arg
1               5                   10                  15

Phe Cys Pro Xaa Phe Lys Val Arg Cys Pro Met
            20                  25
```

```
<210> SEQ ID NO 45
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (8)..(12)
<220> FEATURE:
<221> NAME/KEY: MISC_FEATURE
<222> LOCATION: (9)..(9)
<223> OTHER INFORMATION: Xaa is Dhb amino acid
<220> FEATURE:
<221> NAME/KEY: DISULFID
<222> LOCATION: (14)..(18)
<220> FEATURE:
<221> NAME/KEY: DISULFID
<222> LOCATION: (21)..(25)
<220> FEATURE:
<221> NAME/KEY: DISULFID
<222> LOCATION: (27)..(32)

<400> SEQUENCE: 45

Tyr Thr Glu Val Ser Pro Gln Ala Xaa Ile Val Ala Val Ala Leu Arg
1               5                   10                  15
Ile Ala Asn Trp Ala Leu Arg Phe Ala Pro Ala Phe Lys Val Arg Ala
            20                  25                  30
Pro Met

<210> SEQ ID NO 46
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (7)..(11)
<220> FEATURE:
<221> NAME/KEY: MISC_FEATURE
<222> LOCATION: (8)..(8)
<223> OTHER INFORMATION: Xaa is Dhb amino acid
<220> FEATURE:
<221> NAME/KEY: DISULFID
<222> LOCATION: (13)..(17)
<220> FEATURE:
<221> NAME/KEY: DISULFID
<222> LOCATION: (20)..(24)
<220> FEATURE:
<221> NAME/KEY: DISULFID
<222> LOCATION: (26)..(31)

<400> SEQUENCE: 46

Thr Glu Val Ser Pro Gln Ala Xaa Ile Val Ala Val Ala Leu Arg Ile
1               5                   10                  15
Ala Asn Trp Ala Leu Arg Phe Ala Pro Ala Phe Lys Val Arg Ala Pro
            20                  25                  30
Met

<210> SEQ ID NO 47
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (6)..(10)
<220> FEATURE:
<221> NAME/KEY: MISC_FEATURE
```

```
<222> LOCATION: (7)..(7)
<223> OTHER INFORMATION: Xaa is Dhb amino acid
<220> FEATURE:
<221> NAME/KEY: DISULFID
<222> LOCATION: (12)..(16)
<220> FEATURE:
<221> NAME/KEY: DISULFID
<222> LOCATION: (19)..(23)
<220> FEATURE:
<221> NAME/KEY: DISULFID
<222> LOCATION: (25)..(30)

<400> SEQUENCE: 47

Glu Val Ser Pro Gln Ala Xaa Ile Val Ala Val Ala Leu Arg Ile Ala
1               5                   10                  15

Asn Trp Ala Leu Arg Phe Ala Pro Ala Phe Lys Val Arg Ala Pro Met
            20                  25                  30

<210> SEQ ID NO 48
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (5)..(9)
<220> FEATURE:
<221> NAME/KEY: MISC_FEATURE
<222> LOCATION: (6)..(6)
<223> OTHER INFORMATION: Xaa is Dhb amino acid
<220> FEATURE:
<221> NAME/KEY: DISULFID
<222> LOCATION: (11)..(15)
<220> FEATURE:
<221> NAME/KEY: DISULFID
<222> LOCATION: (18)..(22)
<220> FEATURE:
<221> NAME/KEY: DISULFID
<222> LOCATION: (24)..(29)

<400> SEQUENCE: 48

Val Ser Pro Gln Ala Xaa Ile Val Ala Val Ala Leu Arg Ile Ala Asn
1               5                   10                  15

Trp Ala Leu Arg Phe Ala Pro Ala Phe Lys Val Arg Ala Pro Met
            20                  25                  30

<210> SEQ ID NO 49
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (4)..(8)
<220> FEATURE:
<221> NAME/KEY: MISC_FEATURE
<222> LOCATION: (5)..(5)
<223> OTHER INFORMATION: Xaa is Dhb amino acid
<220> FEATURE:
<221> NAME/KEY: DISULFID
<222> LOCATION: (10)..(14)
<220> FEATURE:
<221> NAME/KEY: DISULFID
<222> LOCATION: (17)..(21)
<220> FEATURE:
<221> NAME/KEY: DISULFID
<222> LOCATION: (23)..(28)

<400> SEQUENCE: 49

Ser Pro Gln Ala Xaa Ile Val Ala Val Ala Leu Arg Ile Ala Asn Trp
```

```
1               5                  10                 15
Ala Leu Arg Phe Ala Pro Ala Phe Lys Val Arg Ala Pro Met
                20                  25                 30

<210> SEQ ID NO 50
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (3)..(7)
<220> FEATURE:
<221> NAME/KEY: MISC_FEATURE
<222> LOCATION: (4)..(4)
<223> OTHER INFORMATION: Xaa is Dhb amino acid
<220> FEATURE:
<221> NAME/KEY: DISULFID
<222> LOCATION: (9)..(13)
<220> FEATURE:
<221> NAME/KEY: DISULFID
<222> LOCATION: (16)..(20)
<220> FEATURE:
<221> NAME/KEY: DISULFID
<222> LOCATION: (22)..(27)

<400> SEQUENCE: 50

Pro Gln Ala Xaa Ile Val Ala Val Ala Leu Arg Ile Ala Asn Trp Ala
1               5                  10                 15

Leu Arg Phe Ala Pro Ala Phe Lys Val Arg Ala Pro Met
                20                  25

<210> SEQ ID NO 51
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (2)..(6)
<220> FEATURE:
<221> NAME/KEY: MISC_FEATURE
<222> LOCATION: (3)..(3)
<223> OTHER INFORMATION: Xaa is Dhb amino acid
<220> FEATURE:
<221> NAME/KEY: DISULFID
<222> LOCATION: (8)..(12)
<220> FEATURE:
<221> NAME/KEY: DISULFID
<222> LOCATION: (15)..(19)
<220> FEATURE:
<221> NAME/KEY: DISULFID
<222> LOCATION: (21)..(26)

<400> SEQUENCE: 51

Gln Ala Xaa Ile Val Ala Val Ala Leu Arg Ile Ala Asn Trp Ala Leu
1               5                  10                 15

Arg Phe Ala Pro Ala Phe Lys Val Arg Ala Pro Met
                20                  25

<210> SEQ ID NO 52
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(5)
```

```
<220> FEATURE:
<221> NAME/KEY: MISC_FEATURE
<222> LOCATION: (2)..(2)
<223> OTHER INFORMATION: Xaa is Dhb amino acid
<220> FEATURE:
<221> NAME/KEY: DISULFID
<222> LOCATION: (7)..(11)
<220> FEATURE:
<221> NAME/KEY: DISULFID
<222> LOCATION: (14)..(18)
<220> FEATURE:
<221> NAME/KEY: DISULFID
<222> LOCATION: (20)..(25)

<400> SEQUENCE: 52

Ala Xaa Ile Val Ala Val Ala Leu Arg Ile Ala Asn Trp Ala Leu Arg
1               5                   10                  15

Phe Ala Pro Ala Phe Lys Val Arg Ala Pro Met
            20                  25

<210> SEQ ID NO 53
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is Dha amino acid
<220> FEATURE:
<221> NAME/KEY: MOD_RES
<222> LOCATION: (9)..(9)
<223> OTHER INFORMATION: Abu
<220> FEATURE:
<221> NAME/KEY: DISULFID
<222> LOCATION: (9)..(12)
<220> FEATURE:
<221> NAME/KEY: DISULFID
<222> LOCATION: (14)..(18)
<220> FEATURE:
<221> NAME/KEY: DISULFID
<222> LOCATION: (21)..(25)
<220> FEATURE:
<221> NAME/KEY: DISULFID
<222> LOCATION: (27)..(32)

<400> SEQUENCE: 53

Tyr Thr Glu Val Ser Pro Gln Xaa Xaa Ile Val Ala Val Ala Leu Arg
1               5                   10                  15

Ile Ala Asn Trp Ala Leu Arg Phe Ala Pro Ala Phe Lys Val Arg Ala
            20                  25                  30

Pro Met

<210> SEQ ID NO 54
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Xaa is Dha amino acid
<220> FEATURE:
<221> NAME/KEY: MOD_RES
<222> LOCATION: (8)..(8)
<223> OTHER INFORMATION: Abu
<220> FEATURE:
<221> NAME/KEY: DISULFID
<222> LOCATION: (8)..(11)
<220> FEATURE:
```

<221> NAME/KEY: DISULFID
<222> LOCATION: (13)..(17)
<220> FEATURE:
<221> NAME/KEY: DISULFID
<222> LOCATION: (20)..(24)
<220> FEATURE:
<221> NAME/KEY: DISULFID
<222> LOCATION: (26)..(31)

<400> SEQUENCE: 54

Thr Glu Val Ser Pro Gln Xaa Xaa Ile Val Ala Val Ala Leu Arg Ile
1               5                   10                  15

Ala Asn Trp Ala Leu Arg Phe Ala Pro Ala Phe Lys Val Arg Ala Pro
            20                  25                  30

Met

<210> SEQ ID NO 55
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa is Dha amino acid
<220> FEATURE:
<221> NAME/KEY: MOD_RES
<222> LOCATION: (7)..(7)
<223> OTHER INFORMATION: Abu
<220> FEATURE:
<221> NAME/KEY: DISULFID
<222> LOCATION: (7)..(10)
<220> FEATURE:
<221> NAME/KEY: DISULFID
<222> LOCATION: (12)..(16)
<220> FEATURE:
<221> NAME/KEY: DISULFID
<222> LOCATION: (19)..(23)
<220> FEATURE:
<221> NAME/KEY: DISULFID
<222> LOCATION: (25)..(30)

<400> SEQUENCE: 55

Glu Val Ser Pro Gln Xaa Xaa Ile Val Ala Val Ala Leu Arg Ile Ala
1               5                   10                  15

Asn Trp Ala Leu Arg Phe Ala Pro Ala Phe Lys Val Arg Ala Pro Met
            20                  25                  30

<210> SEQ ID NO 56
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is Dha amino acid
<220> FEATURE:
<221> NAME/KEY: MOD_RES
<222> LOCATION: (6)..(6)
<223> OTHER INFORMATION: Abu
<220> FEATURE:
<221> NAME/KEY: DISULFID
<222> LOCATION: (6)..(9)
<220> FEATURE:
<221> NAME/KEY: DISULFID
<222> LOCATION: (11)..(15)
<220> FEATURE:
<221> NAME/KEY: DISULFID
<222> LOCATION: (18)..(22)

```
<220> FEATURE:
<221> NAME/KEY: DISULFID
<222> LOCATION: (24)..(29)

<400> SEQUENCE: 56

Val Ser Pro Gln Xaa Xaa Ile Val Ala Val Ala Leu Arg Ile Ala Asn
1               5                   10                  15

Trp Ala Leu Arg Phe Ala Pro Ala Phe Lys Val Arg Ala Pro Met
            20                  25                  30

<210> SEQ ID NO 57
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Dha amino acid
<220> FEATURE:
<221> NAME/KEY: MOD_RES
<222> LOCATION: (5)..(5)
<223> OTHER INFORMATION: Abu
<220> FEATURE:
<221> NAME/KEY: DISULFID
<222> LOCATION: (5)..(8)
<220> FEATURE:
<221> NAME/KEY: DISULFID
<222> LOCATION: (10)..(14)
<220> FEATURE:
<221> NAME/KEY: DISULFID
<222> LOCATION: (17)..(21)
<220> FEATURE:
<221> NAME/KEY: DISULFID
<222> LOCATION: (23)..(28)

<400> SEQUENCE: 57

Ser Pro Gln Xaa Xaa Ile Val Ala Val Ala Leu Arg Ile Ala Asn Trp
1               5                   10                  15

Ala Leu Arg Phe Ala Pro Ala Phe Lys Val Arg Ala Pro Met
            20                  25                  30

<210> SEQ ID NO 58
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Dha amino acid
<220> FEATURE:
<221> NAME/KEY: MOD_RES
<222> LOCATION: (4)..(4)
<223> OTHER INFORMATION: Abu
<220> FEATURE:
<221> NAME/KEY: DISULFID
<222> LOCATION: (4)..(7)
<220> FEATURE:
<221> NAME/KEY: DISULFID
<222> LOCATION: (9)..(13)
<220> FEATURE:
<221> NAME/KEY: DISULFID
<222> LOCATION: (16)..(20)
<220> FEATURE:
<221> NAME/KEY: DISULFID
<222> LOCATION: (22)..(27)

<400> SEQUENCE: 58

Pro Gln Xaa Xaa Ile Val Ala Val Ala Leu Arg Ile Ala Asn Trp Ala
```

```
                1               5                  10                    15
Leu Arg Phe Ala Pro Ala Phe Lys Val Arg Ala Pro Met
                20                  25

<210> SEQ ID NO 59
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Dha amino acid
<220> FEATURE:
<221> NAME/KEY: MOD_RES
<222> LOCATION: (3)..(3)
<223> OTHER INFORMATION: Abu
<220> FEATURE:
<221> NAME/KEY: DISULFID
<222> LOCATION: (3)..(6)
<220> FEATURE:
<221> NAME/KEY: DISULFID
<222> LOCATION: (8)..(12)
<220> FEATURE:
<221> NAME/KEY: DISULFID
<222> LOCATION: (15)..(19)
<220> FEATURE:
<221> NAME/KEY: DISULFID
<222> LOCATION: (21)..(26)

<400> SEQUENCE: 59

Gln Xaa Xaa Ile Val Ala Val Ala Leu Arg Ile Ala Asn Trp Ala Leu
1               5                  10                  15
Arg Phe Ala Pro Ala Phe Lys Val Arg Ala Pro Met
                20                  25

<210> SEQ ID NO 60
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Abu
<220> FEATURE:
<221> NAME/KEY: MISC_FEATURE
<222> LOCATION: (1)..(1)
<223> OTHER INFORMATION: N-terminal propanedione
<220> FEATURE:
<221> NAME/KEY: DISULFID
<222> LOCATION: (1)..(4)
<220> FEATURE:
<221> NAME/KEY: DISULFID
<222> LOCATION: (6)..(10)
<220> FEATURE:
<221> NAME/KEY: DISULFID
<222> LOCATION: (13)..(17)
<220> FEATURE:
<221> NAME/KEY: DISULFID
<222> LOCATION: (19)..(24)

<400> SEQUENCE: 60

Xaa Ile Val Ala Val Ala Leu Arg Ile Ala Asn Trp Ala Leu Arg Phe
1               5                  10                  15
Ala Pro Ala Phe Lys Val Arg Ala Pro Met
                20                  25

<210> SEQ ID NO 61
```

```
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Abu
<220> FEATURE:
<221> NAME/KEY: DISULFID
<222> LOCATION: (1)..(4)
<220> FEATURE:
<221> NAME/KEY: DISULFID
<222> LOCATION: (6)..(10)
<220> FEATURE:
<221> NAME/KEY: DISULFID
<222> LOCATION: (13)..(17)
<220> FEATURE:
<221> NAME/KEY: DISULFID
<222> LOCATION: (19)..(24)

<400> SEQUENCE: 61

Xaa Ile Val Ala Val Ala Leu Arg Ile Ala Asn Trp Ala Leu Arg Phe
 1               5                  10                  15

Ala Pro Ala Phe Lys Val Arg Ala Pro Met
             20                  25

<210> SEQ ID NO 62
<211> LENGTH: 33
<212> TYPE: PRT
<213> ORGANISM: Artificial Sequence
<220> FEATURE:
<223> OTHER INFORMATION: Synthetic

<400> SEQUENCE: 62

Val Thr Ser Lys Ser Leu Cys Thr Pro Gly Cys Ile Thr Gly Val Leu
 1               5                  10                  15

Met Cys Leu Thr Gln Asn Ser Cys Val Ser Cys Asn Ser Cys Ile Arg
             20                  25                  30

Cys

<210> SEQ ID NO 63
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: optionally L
<220> FEATURE:
<221> NAME/KEY: MISC_FEATURE
<222> LOCATION: (19)..(19)
<223> OTHER INFORMATION: optionally I
<220> FEATURE:
<221> NAME/KEY: MISC_FEATURE
<222> LOCATION: (23)..(23)
<223> OTHER INFORMATION: optionally N

<400> SEQUENCE: 63

Met Ala Lys Phe Asp Asp Phe Asp Leu Asp Ile Val Val Lys Lys Gln
 1               5                  10                  15

Asp Asp Val Val Gln Pro Lys
             20

<210> SEQ ID NO 64
<211> LENGTH: 76
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (49)..(49)
<223> OTHER INFORMATION: optionally K

<400> SEQUENCE: 64

Gly Ser Ser His His His His His Ser Gln Asp Pro Met Lys Gly
1               5                   10                  15

Gly Ile Gln Met Glu Lys Gln Glu Gln Thr Phe Val Ser Lys Ile Ser
            20                  25                  30

Glu Glu Glu Leu Lys Lys Leu Ala Gly Gly Tyr Thr Glu Val Ser Pro
        35                  40                  45

Gln Ser Thr Ile Val Cys Val Ser Leu Arg Ile Cys Asn Trp Ser Leu
    50                  55                  60

Arg Phe Cys Pro Ser Phe Lys Val Arg Cys Pro Met
65                  70                  75

<210> SEQ ID NO 65
<211> LENGTH: 27
<212> TYPE: PRT
<213> ORGANISM: Artificial Sequence
<220> FEATURE:
<223> OTHER INFORMATION: Synthetic

<400> SEQUENCE: 65

Ser Thr Ile Val Cys Val Ser Leu Arg Ile Cys Asn Trp Ser Leu Arg
1               5                   10                  15

Phe Cys Pro Ser Phe Lys Val Arg Cys Pro Met
            20                  25

<210> SEQ ID NO 66
<211> LENGTH: 7
<212> TYPE: PRT
<213> ORGANISM: Artificial Sequence
<220> FEATURE:
<223> OTHER INFORMATION: Synthetic

<400> SEQUENCE: 66

Tyr Thr Glu Val Ser Pro Gln
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Abu

<400> SEQUENCE: 67

Xaa Ala Arg Val Ala
1               5

<210> SEQ ID NO 68
<211> LENGTH: 5
<212> TYPE: PRT
<213> ORGANISM: Artificial Sequence
<220> FEATURE:
<223> OTHER INFORMATION: Synthetic
```

```
<400> SEQUENCE: 68

Thr Ala Arg Val Cys
1               5

<210> SEQ ID NO 69
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Dhb

<400> SEQUENCE: 69

Ala Xaa Ile Val Ala
1               5

<210> SEQ ID NO 70
<211> LENGTH: 5
<212> TYPE: PRT
<213> ORGANISM: Artificial Sequence
<220> FEATURE:
<223> OTHER INFORMATION: Synthetic

<400> SEQUENCE: 70

Ser Thr Ile Val Cys
1               5
```